(12) United States Patent
Krupnick et al.

(10) Patent No.: US 12,226,453 B2
(45) Date of Patent: Feb. 18, 2025

(54) EOSINOPHILS ALLEVIATE LUNG ALLOGRAFT REJECTION THROUGH THEIR MODULATION OF CD8+ T CELLS

(71) Applicant: University of Virginia Patent Foundation, Charlottesville, VA (US)

(72) Inventors: Alexander Sasha Krupnick, Charlottesville, VA (US); Yizhan Guo, Charlottesville, VA (US); Oscar Okwudiri Onyema, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 880 days.

(21) Appl. No.: 16/804,882

(22) Filed: Feb. 28, 2020

(65) Prior Publication Data

US 2020/0276269 A1 Sep. 3, 2020

Related U.S. Application Data

(60) Provisional application No. 62/811,580, filed on Feb. 28, 2019.

(51) Int. Cl.
*A61K 38/19* (2006.01)
*A61K 38/20* (2006.01)
*A61P 37/06* (2006.01)

(52) U.S. Cl.
CPC ........ *A61K 38/195* (2013.01); *A61K 38/2033* (2013.01); *A61P 37/06* (2018.01)

(58) Field of Classification Search
None
See application file for complete search history.

(56) References Cited

U.S. PATENT DOCUMENTS

| 8,247,175 B2 | 8/2012 | Keshavjee et al. |
| 8,637,232 B2 | 1/2014 | Lama |
| 10,000,809 B2 | 6/2018 | Keshavjee et al. |
| 2017/0114411 A1 | 4/2017 | Mitchell et al. |

OTHER PUBLICATIONS

Onyema et al Eosinophils promote inducible NOS-mediated lung allograft acceptance JCI Insight (2017) 2(24):e96455 (Year: 2017).*
Larose et al. Regulation of Eosinophil and Group 2 Innate Lymphoid Cell Trafficking in Asthma. Frontiers in Medicine (2017) 4(136) (Year: 2017).*
Shi et al (Effect of Inhaled Interluekin-5 on Number and Activity of Eosinophils in Circulation from Asthmatics Clinical Immunology (1999) 91(2):163-169) (Year: 1999).*
Fukuyama et al Effect of Eotaxin and Platelet-activating Factor on Airway Inflammation and Hyperresponsiveness in Guinea Pigs in Vivo. Am J Respir Crit Care Med (2000) 161:1844-1849 (Year: 2000).*
Scheffert et al Immunosuppression in lung transplantation. Journal of Thoracic Disease (2014) 6(8):1039-1053 (Year: 2014).*
Onyema et al. Eosinophils alleviate lung allograft rejection through their modulation of CD8+ T Cells. Journal of Immunology. 200 (Supplement 1); Published: May 1, 2018 (Year: 2018).*
Abdala-Valencia et al., "Shaping eosinophil identity in the tissue contexts of development, homeostasis, and disease." J. Leukoc. Biol., vol. 104(1), pp. 95-108 (2018).
Altschul et al., "Basic local search alignment tool." J. Mol. Biol., vol. 215(3), pp. 403-410 (1990).
Altschul et al., "Gapped Blast and PSI-Blast: a new generation of protein database search programs." Nucleic Acids Res., vol. 25(17), pp. 3389-3402 (1997).
Altshcul et al., "Protein database searches for multiple alignments," Proc. Natl. Acad. Sci. USA, vol. 87(14), pp. 5509-5513 (1990).
Arbon et al., "Eosinophil count, allergies, and rejection in pediatric heart transplant recipients." J. Heart Lung Transplant., vol. 34(8), pp. 1103-1111 (2015).
Arnold et al., "Eosinophils suppress Th1 responses and restrict bacterially induced gastrointestinal inflammation." J. Exp. Med., vol. 215(8), pp. 2055-2072 (2018).
Ashouri et al., "Endogenous Nur77 Is a Specific Indicator of Antigen Receptor Signaling in Human T and B Cells." J. Immunol., vol. 198(2), pp. 657-668 (2017).
Balsara et al., "A single-center experience of 1500 lung transplant patients." J. Thorac. Cadiovasc. Surg., vol. 156 (2), pp. 894-905 (2018).
Bolger et al., "Trimmomatic: A flexible trimmer for Illumina Sequence Data." Bioinformatics, vol. 30, pp. 2114-2120 (2014).
Budden et al., "Emerging pathogenic links between microbiota and the gut-lung axis." Nat. Rev. Microbiol., vol. 15(1), pp. 55-63 (2017).
Carr et al., "Eosinophilic bioactivities in severe asthma." World Allergy Organ J., vol. 9, Article No. 21 (2016).
Chen et al., "Increased T cell glucose uptake reflects acute rejection in lung grafts." Am. J. Transplant., vol. 13(10), pp. 2540-2549 (2013).
Chong et al., "Human CD8(+) T cells drive Th1 responses through the differentiation of TNF/iNOS-producing dendritic cells." Eur. J. Immunol., vol. 41(6), pp. 1639-1651 (2011).

(Continued)

*Primary Examiner* — Juliet C Switzer
*Assistant Examiner* — Katherine Ann Holtzman
(74) *Attorney, Agent, or Firm* — Jenkins, Taylor & Hunt, P.A.

(57) ABSTRACT

Provided are methods for enhancing immunosuppression in the lung of a subject, In some embodiments, the methods include administering to the subject a composition comprising at least one eosinophil recruiting agent, wherein the administering is in an amount and via a route of administration sufficient to induce recruitment of eosinophils to the lung of the subject to thereby enhance immunosuppression in the lung of the subject. Also provided are methods for enhancing tolerance to lung transplants, enhancing recruitment of eosinophils to the lungs, modulating T cell-mediated immune responses in the lungs, and reducing TCR signal transduction in the lungs.

15 Claims, 45 Drawing Sheets
(31 of 45 Drawing Sheet(s) Filed in Color)
Specification includes a Sequence Listing.

(56) References Cited

OTHER PUBLICATIONS

Conde et al., "DC-SIGN(+) Macrophages Control the Induction of Transplantation Tolerance." Immunity, vol. 42(6), pp. 1143-1158 (2015).
Deuse et al., "Mechanisms behind local immunosuppression using inhaled tacrolimus in preclinical models of lung transplantation." Am. J. Respir. Cell. Mol. Biol., vol. 43(4), pp. 403-412 (2010).
Devereux et al., "A comprehensive set of sequence analysis programs for the VAX." Nucleic Acids Res., vol. 12(1 Pt 1), pp. 387-395 (1984).
Drake et al., "Human and Mouse Eosinophils Have Antiviral Activity against Parainfluenza Virus." Am. J. Respir. Cell Mol. Biol., vol. 55(3), pp. 387-394 (2016).
Fonseca et al., "TNF-alpha mediates the induction of nitric oxide synthase in macrophages but not in neutrophils in experimental cutaneous leishmaniasis." Eur. J. Immunol., vol. 33(8), pp. 387-394 (2016).
Fulkerson et al., "Targeting eosinophils in allergy, inflammation and beyond." Nat. Rev. Drug Discov., vol. 12(2), pp. 117-129 (2013).
Galli et al., "The development of allergic inflammation." Nature, vol. 454, pp. 445-454 (2008).
Garcia et al., "Monocytic suppressive cells mediate cardiovascular transplantation tolerance in mice." J. Clin. I., vol. 120(7), pp. 2486-2496 (2010).
Gelman et al., "CD4+ T lymphocytes are not necessary for the acute rejection of vascularized mouse lung transplants." J. Immunol., vol. 180(7), pp. 4754-4762 (2008).
Gelman et al., "Cutting edge: Acute lung allograft rejection is independent of secondary lymphoid organs." J. Immunol., vol. 182(7), pp. 3969-3973 (2009).
Goldman et al., "A role for eosinophils in transplant rejection." Trends Immunol., vol. 22(5), pp. 247-251 (2001).
Goldman et al., "High macrophage PD-L1 expression not responsible for T cell suppression." Cell. Immunol., vol. 324, pp. 50-58 (2018).
Griseri et al., "Granulocyte Macrophage Colony-Stimulating Factor-Activated Eosinophils Promote Interleukin-23 Driven Chronic Colitis." Immunity, vol. 43(1), pp. 187-199 (2015).
Groves et al., "Inhaled cyclosporine and pulmonary function in lung transplant recipients." J. Aerosol. Med. Pulm. Drug Deliv., vol. 23(1), pp. 31-39 (2010).
Hagan et al., "Eosinophilia and resistance to Schistosoma haematobium in man." Parasite Immunol., vol. 7(6), pp. 625-632 (1985).
Helft et al., "GM-CSF Mouse Bone Marrow Cultures Comprise a Heterogeneous Population of CD11c(+)MHCII(+) Macrophages and Dendritic Cells." Immunity, vol. 42(6), 1197-1211 (2015).
Henikoff et al., "Amino acid substitution matrices from protein blocks." Proc. Natl. Acad. Sci. USA, vol. 89, pp. 10915-10919 (1992).
Iijima et al., "Nitric oxide and protein nitration are eosinophil dependent in allergen-challenged mice." Am. J. Respir. Crit. Care Med., vol. 163(5), pp. 1233-1240 (2001).
Jacobsen et al., "Allergic pulmonary inflammation in mice is dependent on eosinophil-induced recruitment of effector T cells." J. Exp. Med., vol. 205(3), vol. 699-710 (2008).
Jacobsen et al., "Differential activation of airway eosinophils induces IL-13-mediated allergic Th2 pulmonary responses in mice." Allergy, vol. 70(9), pp. 1148-1159 (2015).
Jacobsen et al., "Eosinophil activities modulate the immune/inflammatory character of allergic respiratory responses in mice." Allergy, vol. 69(3), pp. 315-327 (2014).
Jacobsen et al., "Eosinophils regulate dendritic cells and Th2 pulmonary immune responses following allergen provocation." J. Immunol., vol. 187(11), pp. 6059-6068 (2011).
Jacobsen et al., "Eosinophils: singularly destructive effector cells or purveyors of immunoregulation?" J. Allergy Clin. Immunol., vol. 119(6), pp. 1313-1320 (2007).
Jacobsen et al., "Lung Pathologies in a Chronic Inflammation Mouse Model Are Independent of Eosinophil Degranulation." Am. J. Resp. Crit. Care Med., vol. 195(10), pp. 1321-1332 (2017).
Jacobsen et al., "Re-defining the unique roles for eosinophils in allergic respiratory inflammation." Clin. Exp. Allergy, vol. 44(9), pp. 1119-1136 (2014).
Jacobsen et al., "The expanding role(s) of eosinophils in health and disease." Blood, vol. 120(19), pp. 3882-3890 (2012).
Karlin et al., "Applications and statistics for multiple high-scoring segments in molecular sequences." Proc. Natl. Acad. Sci. USA, vol. 90, pp. 5873-5877 (1993).
Kato et al., "Polarization of naïve CD4+ T cells toward the Th1 subset by CTLA-4 costimulation." J. Immunol., vol. 164(7), pp. 3554-3562 (2000).
Kishimoto et al., "Th1 cytokines, programmed cell death, and alloreactive T cell clone size in transplant tolerance." J. Clin. Invest., col. 109(11), pp. 1471-1479 (2002).
Knoop et al., "Immunosuppressive therapy after human lung transplantation." Eur. Respir. J., vol. 23(1), pp. 159-171 (2004).
Kreisel et al., "Emergency granulopoiesis promotes neutrophil-dendritic cell encounters that prevent mouse lung allograft acceptance." Blood, vol. 118(23), pp. 6172-6182 (2011).
Krupnick et al., "Central memory CD8+ T lymphocytes mediate lung allograft acceptance." J. Clin. Invest., vol. 124(3), pp. 1130-1143 (2014).
Krupnick et al., "Orthotopic mouse lung transplantation as experimental methodology to study transplant and tumor biology." Nat. Protoc., vol. 4(1), pp. 86-93 (2009).
Kulkarni et al., "Bronchiolitis obliterans syndrome-free survival after lung transplantation: An International Society for Heart and Lung Transplantation Thoracic Transplant Registry analysis." J. Heart Lung Transplant., vol. 38(1), pp. 5-16 (2018).
Larsen et al., "Long-term acceptance of skin and cardiac allografts after blocking CD40 and CD28 pathways." Nature, vol. 381, pp. 434-438 (1996).
Lee et al., "Eosinophils in health and disease: the LIAR hypothesis." Clin. Exp. Allergy, vol. 40(4), pp. 563-575 (2010).
Lee et al., "Expression of IL-5 in thymocytes/T cells leads to the development of a massive eosinophilia, extramedullary eosinophilopoiesis, and unique histopathologies." J. Immunol., vol. 158(3), pp. 1332-1344 (1997).
Lee et al., "Human versus mouse eosinophils: 'that which we call an eosinophil, by any other name would stain as red.'" J. Allergy Clin. Immunol., vol. 130(3), pp. 572-584 (2012).
Li et al., "Lung transplant acceptance is facilitated by early events in the graft and is associated with lymphoid neogenesis." Mucosal Immunol., vol. 5(5), pp. 544-554 (2012).
Li et al., "Tolerogenic dendritic cells and their applications in transplantation." Cell. Mol. Immunol., vol. 12(1), pp. 24-30 (2015).
Lilly et al., "Eosinophil deficiency compromises lung defense against Aspergillus fumigatus." Infect Immun., vol. 82(3), pp. 1315-1325 (2014).
Liu et al., "Generation of Th1 and Th2 chemokines by human eosinophils: evidence for a critical role of TNF-alpha." J. Immunol., vol. 179(7), pp. 4840-4848 (2007).
Lotfi et al., "Eosinophils induce DC maturation, regulating immunity." J. Leukoc. Biol., vol. 83(3), pp. 456-460 (2008).
MacPherson et al., "Eosinophils are a major source of nitric oxide-derived oxidants in severe asthma: characterization of pathways available to eosinophils for generating reactive nitrogen species." J. Immunol., vol. 166(9), pp. 5763-5772 (2001).
Markey et al., "Cross-dressing by donor dendritic cells after allogeneic bone marrow transplantation contributes to formation of the immunological synapse and maximizes responses to indirectly presented antigen." J. Immunol., vol. 192(11), pp. 5426-5433 (2014).
Martinez et al., "Evidence for a nonclassical pathway of graft rejection involving interleukin 5 and eosinophils." Transplantation, vol. 55(4), pp. 909-918 (1993).
Masterson et al., "Eosinophil-mediated signaling attenuates inflammatory responses in experimental colitis." Gut, Voil. 64(8), pp. 1236-1247 (2015).
Mesnil et al., "Lung-resident eosinophils represent a distinct regulatory eosinophil subset." J. Clin. Invest., vol. 126(9), pp. 3279-3295 (2016).

(56) References Cited

OTHER PUBLICATIONS

Miller et al., "Distinct Graft-Specific TCR Avidity Profiles during Acute Rejection and Tolerance." Cell. Rep., vol. 24(8), pp. 2112-2126 (2018).
Moran et al., "T cell receptor signal strength in Treg and iNKT cell development demonstrated by a novel fluorescent reporter mouse." J. Exp. Med., vol. 208(6), pp. 1279-1289 (2011).
Morikawa et al., "Augmentation of nitric oxide production by gamma interferon in a mouse vascular endothelial cell line and its modulation by tumor necrosis factor alpha and lipopolysaccharide." Infect. Immunol., vol. 68(11), pp. 6209-6214 (2000).
Murphy, "Nitric oxide and cell death." Biochim. Biophys. Acta., vol. 1411(2-3), vol. 401-414 (1999).
Nagaraj et al., "Altered recognition of antigen is a mechanism of CD8+ T cell tolerance in cancer." Nat. Med., vol. 13(7), pp. 828-835 (2007).
Nagaraj et al., "Mechanism of T cell tolerance induced by myeloid-derived suppressor cells." J. Immunol., vol. 184(6), pp. 3106-3116 (2010).
Nagral et al., "Eosinophils in acute cellular rejection in liver allografts." Liver Transpl. Surg., vol. 4(5), pp. 355-362 (1998).
Nair et al., "Mepolizumab for prednisone-dependent asthma with sputum eosinophilia." New Engl. J. Med., vol. 360(10), pp. 985-993 (2009).
Needleman et al., "A general method applicable to the search for similarities in the amino acid sequence of two proteins." J. Mol. Biol., vol. 48, pp. 443-453 (1970).
Okazaki et al., "A mouse model of orthotopic vascularized aerated lung transplantation." Am. J. Transplant., vol. 7(6), pp. 1672-1679 (2007).
Onyema et al., "Eosinophils downregulate lung alloimmunity by decreasing TCR signal transduction." JCI Insight, vol. 4(11), Article ID e128241 (2019).
Onyema et al., "Eosinophils promote inducible NOS-mediated lung allograft acceptance." JCI Insight, vol. 2(24), Article ID e96455 (2017).
Paoliello-Paschoalato et al., "Interleukin 4 induces the expression of inducible nitric oxide synthase in eosinophils." Cytokine, vol. 30(3), pp. 116-124 (2005).
Pardoll, "The blockade of immune checkpoints in cancer immunotherapy." Nat. Rev. Cancer, vol. 12(4), pp. 252-264 (2012).
Patsoukis et al., "Selective effects of PD-1 on Akt and Ras pathways regulate molecular components of the cell cycle and inhibit T cell proliferation." Sci Signal., vol. 5(230), Article ID ra46 (2012).
Pearson et al., "Improved tools for biological sequence comparison." Proc. Natl. Acad. Sci. USA, vol. 85(8), pp. 2444-2448 (1988).
Percopo et al., "SiglecF+Gr1hi eosinophils are a distinct subpopulation within the lungs of allergen-challenged mice." J. Leukoc. Biol., vol. 101, pp. 321-328 (2017).
Pillay et al., "A subset of neutrophils in human systemic inflammation inhibits T cell responses through Mac-1." J. Clin. Invest., vol. 122(1), pp. 327-336 (2012).
Rankin et al., "Eotaxin and eosinophil recruitment: implications for human disease." Mol. Med. Today, vol. 6(1), pp. 20-27 (2000).
Rosenberg et al., "Eosinophils: changing perspectives in health and disease." Nat. Rev. Immunol., vol. 13(1), pp. 9-22 (2013).
Roufosse et al., "Long-term safety of mepolizumab for the treatment of hypereosinophilic syndromes." J. Allergy Clin. Immunol., vol. 131(2), pp. 461-467 (2013).
Sayegh et al., "CD28-B7 blockade after alloantigenic challenge in vivo inhibits Th1 cytokines but spares Th2." J. Exp. Med., vol. 181(5), 1869-1874 (1995).
Schenk et al., "Donor-reactive CD8 memory T cells infiltrate cardiac allografts within 24-h posttransplant in naïve recipients." Am. J. Transplant., vol. 8(8), pp. 1652-1661 (2008).
Schouppe et al., "Modulation of CD8(+) T-cell activation events by monocytic and granulocytic myeloid-derived suppressor cells." vol. 218(11), pp. 1385-1391 (2013).
Schrum et al., "High-sensitivity detection and quantitative analysis of native protein-protein interactions and multiprotein complexes by flow cytometry." Sci. SKTE, vol. 2007(389) (28 pages) (2007).
Sharpe, "Mechanisms of costimulation." Immunol. Rev., vol. 229(1), pp. 5-11 (2011).
Shen et al., "Determinants of eosinophil survival and apoptotic cell death." Apoptosis, vol. 20(2), pp. 224-234 (2015).
Smith et al., "Comparative biosequence metrics." J. Mol. Evol., vol. 18(1), pp. 38-46 (1981).
Szabolcs et al., "Acute cardiac allograft rejection in nitric oxide synthase-2(-/-) and nitric oxide synthase-2(+/+) mice: effects of cellular chimeras on myocardial inflammation and cardiomyocyte damage and apoptosis." Circulation, vol. 103(20), pp. 2514-2520 (2001).
Takahashi et al., "PD-1 expression on CD8(+) cT cells regulates their differentiation within lung allografts and is critical for tolerance induction." Am. J. Transplant., vol. 18(1), pp. 216-225 (2018).
Tanaka et al., "PDL1 is required for peripheral transplantation tolerance and protection from chronic allograft rejection." J. Immunol., vol. 179(8), pp. 5204-5210 (2007).
Veres et al., "Allergen-Induced CD4+ T Cell Cytokine Production within Airway Mucosal Dendritic Cell-T Cell Clusters Drives the Local Recruitment of Myeloid Effector Cells." J. Immunol., vol. 198(2), pp. 895-907 (2017).
Vos et al., "Inhibition of inducible nitric oxide synthase improves graft function and reduces tubulointerstitial injury in renal allograft rejection." Eur. J. Pharmacol., vol. 391(1-2), pp. 31-38 (2000).
Wabnitz et al., "L-plastin phosphorylation: a novel target for the immunosuppressive drug dexamethasone in primary human T cells." Eur. J. Immunol., vol. 41 (11), pp. 3157-3169 (2011).
Watson et al., "Cytokines contribute to airway dysfunction in antigen-challenged guinea pigs: inhibition of airway hyperreactivity, pulmonary eosinophil accumulation, and tumor necrosis factor generation by pretreatment with an interleukin-1 receptor antagonist." Am. J. Respir. Cell. Mol. Biol., vol. 4, pp. 365-369 (1993).
Wegmann, "Targeting eosinophil biology in asthma therapy." Am. J. Respir. Cell. Mol. Biol., vol. 45(4), pp. 667-674 (2011).
Witt et al., "Lung transplant immunosuppression—time for a new approach?" Expert Rev. Clin. Immunol., vol. 10(11), pp. 1419-1421 (2014).
Yang et al., "Depletion of eosinophil infiltration by anti-IL-5 monoclonal antibody (TRFK-5) accelerates open skin wound epithelial closure." Am. J. Pathol., vol. 151(3), pp. 813-819 (1997).
Guo et al. (2022) "Ischemia reperfusion injury facilitates lung allograft acceptance through IL-33-mediated activation of donor-derived IL-5 producing group 2 innate lymphoid cells," Am J Transplant, vol. 22, pp. 1963-1975.
Mould et al. (1997) "Relationship between Interleukin-5 and Eotaxin in Regulating Blood and Tissue Eosinophilia in Mice," J Clin Invest., vol. 99, No. 5, pp. 1064-1071.
Mould et al. (2000) "The Effect of IL-5 and Eotaxin Expression in the Lung on Eosinophil Trafficking and Degranulation and the Induction of Bronchial Hyperreactivity," J Immunol, vol. 164, No. 4, pp. 2142-2150.
Yamaguchi et al. (1988) "Purified Interleukin 5 Supports the Terminal Differentiation and Proliferation of Murine Eosinophilic Precursors," J. Exp. Med., vol. 167, pp. 43-56.

* cited by examiner

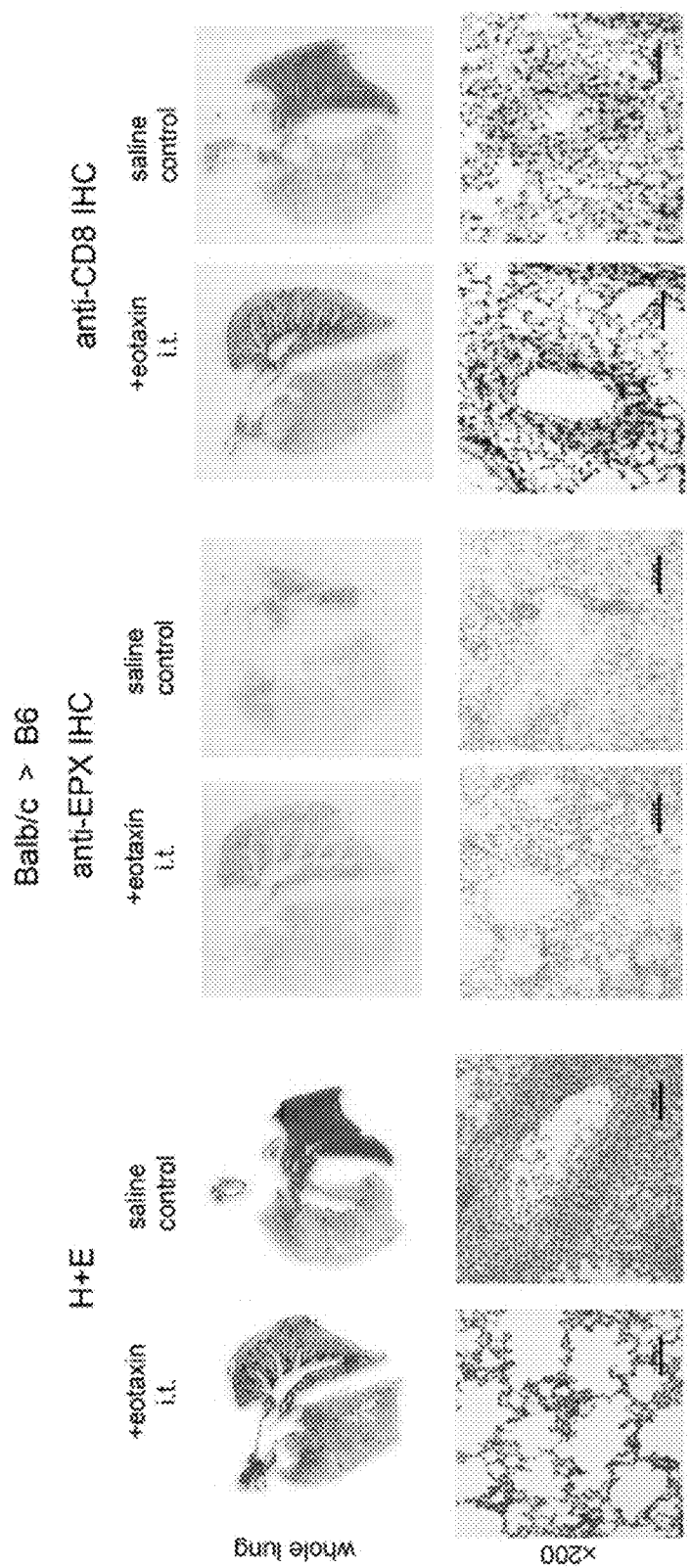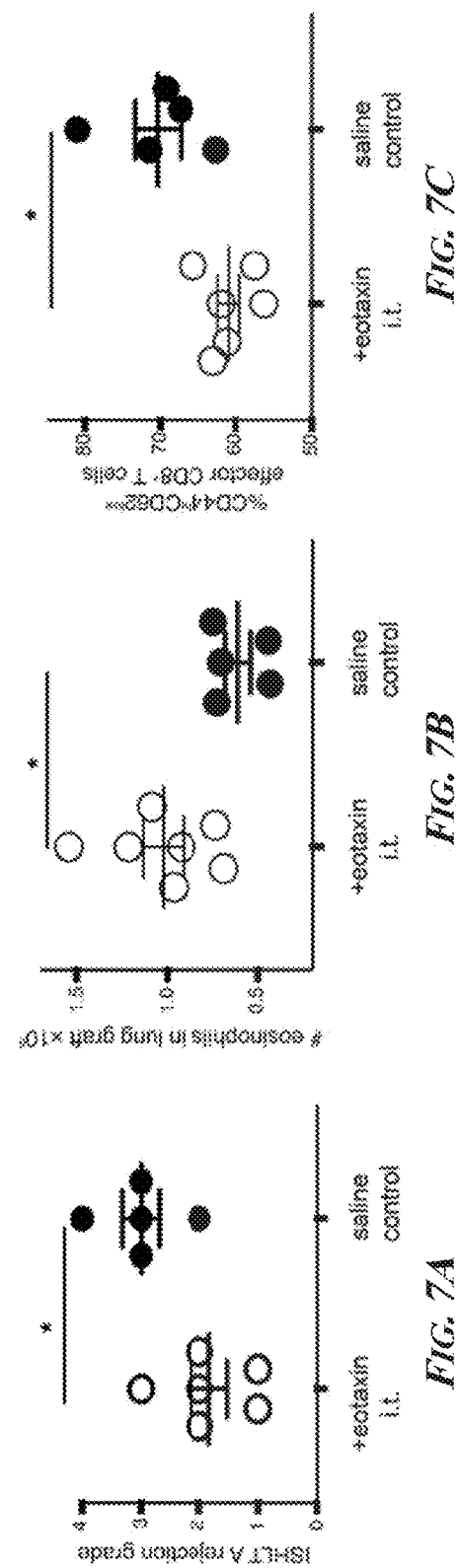
FIG. 7A  FIG. 7B  FIG. 7C

EOSINOPHILS ALLEVIATE LUNG ALLOGRAFT REJECTION THROUGH THEIR MODULATION OF CD8+ T CELLS

CROSS REFERENCE TO RELATED APPLICATION

The presently disclosed subject matter claims the benefit of U.S. Provisional Patent Application Ser. No. 62/811,580, filed Feb. 28, 2019, the disclosure of which is incorporated herein by reference in its entirety.

GOVERNMENT INTEREST

This invention was made with government support under grants AI116501 and AI145108 awarded by the National Institutes of Health. The government has certain rights in the invention.

TECHNICAL FIELD

The presently disclosed subject matter relates, in general, to methods for modulating immune responses in the lungs, optionally wherein the immune responses are associated with one or more biological activities of eosinophils present in and/or recruited to the lungs. More particularly, the presently disclosed subject matter relates to methods for using eosinophil recruiting agents to modulate immune responses in the lungs of subjects.

BACKGROUND

Lung grafts have the worst overall survival of all solid organs (Balsara et al., 2018). A complex and unique immunoregulatory network, that differs significantly from other organ grafts, is at least partially responsible for such poor long-term outcomes. Clinically accepted immunosuppression regimens, that globally downregulate or even temporarily ablate the adaptive immune response, result in acceptable long-term survival of heart and kidney grafts but yield close to a 50% lung allograft loss 5 years post-engraftment (Kulkarni et al., 2019). It has been suggested that unique immunoregulatory pathways that contribute to acceptance of this mucosal barrier organ could require a different strategy for long-term graft survival (Knoop et al., 2004; Witt et al., 2014). For example, depletion of CD8$^+$ T cells as well as other pro-inflammatory cells, contributes to the acceptance of most transplanted organs but prevents lung allograft acceptance (Witt et al., 2014; Witt et al., 2014).

Recent work has suggested that myeloid cells might play an important role in mediating allo-specific tolerance. DC-SIGN$^+$ macrophages, for example, are necessary for heart allograft acceptance (Conde et al., 2015). Bone marrow derived CD11b$^+$CD115$^+$Gr1$^+$ monocytes, a type of myeloid-derived suppressor cells, similarly have the capacity to downregulate the adaptive immune response during tolerance induction in the heart (Garcia et al., 2010). A group of dendritic cells (DCs), described as tolerogenic DCs, can potentiate solid organ acceptance in other models as well (Li & Shi, 2015). The presence of granulocytic cells, however, is generally considered deleterious for successful organ engraftment. Neutrophilia associated with ischemia-reperfusion injury has been associated with co-stimulatory blockade resistant lung allograft rejection (Kreisel et al., 2011) and eosinophils have been shown to contribute to rejection of multiple solid organs (Martinez et al., 1993; Nagral et al., 1998). Furthermore, eosinophils promote damaging inflammation in many other disease processes, specifically in mucosal barrier organs (Griseri et al., 2015; Carr et al., 2016).

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter relates to methods for enhancing immunosuppression in the lungs of subjects. In some embodiments, the methods comprise administering to a subject a composition comprising at least one eosinophil recruiting agent, wherein the administering is in an amount and via a route of administration sufficient to induce recruitment of eosinophils to the lung of the subject to thereby enhance immunosuppression in the lung of the subject. In some embodiments, the lung is a transplanted lung in the subject, optionally wherein the transplanted lung is allogeneic to the subject, and the immunosuppression is sufficient to reduce rejection of the transplanted lung in the subject. In some embodiments, the composition is formulated for administration by any one of intratracheal installation, insufflation, nebulization, dry powder inhalation, aerosol inhalation, and combinations thereof. In some embodiments, the eosinophil recruiting agent is selected from the group consisting of an interleukin-5 (IL-5), an eotaxin, a platelet activating factor, an eicosanoid, or any combination thereof. In some embodiments, the eosinophil recruiting agent comprises eotaxin-1 and/or eotaxin-2, and optionally further comprises IL-5.

In some embodiments, the presently disclosed methods further comprise administering to the subject at least one additional immunosuppressive agent. In some embodiments, the at least one additional immunosuppressive agent is selected from the group consisting of methotrexate, cyclophosphamide, cyclosporine, cyclosporin A, chloroquine, hydroxychloroquine, sulfasalazine (sulphasalazopyrine), a gold salt, D-penicillamine, leflunomide, azathioprine, anakinra, infliximab (REMICADE), etanercept, a TNFα blocker, a non-steroidal anti-inflammatory drug (NSAID), or any combination thereof. In some embodiments, the NSAID is selected from the group consisting of acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, a cyclooxygenase-2 (Cox-2) inhibitor, tramadol, rapamycin (sirolimus), an analog thereof, or any combination thereof.

In some embodiments, the presently disclosed subject matter also relates to methods for enhancing tolerance to a lung transplant in a subject. In some embodiments, the methods comprise administering to a subject a composition comprising at least one eosinophil recruiting agent, wherein the administering is in an amount and via a route of administration sufficient to induce recruitment of eosinophils to the lung of the subject to thereby enhance tolerance to the lung transplant in the subject. In some embodiments, the at least one eosinophil recruiting agent is administered to the subject in one or more doses concurrently with and/or subsequent to the lung transplant being introduced into the subject. In some embodiments, the lung transplant is allogenic to the subject. In some embodiments, the subject is an otherwise non-immunosuppressed subject.

In some embodiments, the presently disclosed subject matter also relates to methods for enhancing recruitment of eosinophils to a lung of a subject. In some embodiments, the methods comprise administering to the subject a composition comprising at least one eosinophil recruiting agent, wherein the administering enhances recruitment of eosinophils to the lung of the subject. In some embodiments, the lung is a transplanted lung.

In some embodiments, the presently disclosed subject matter also relates to methods for modulating T cell-mediated immune responses in a lung of subjects. In some embodiments, the methods comprise administering to a subject a composition comprising at least one eosinophil recruiting agent, wherein the administering enhances recruitment of eosinophils to the lung of the subject to thereby modulate the T cell-mediated immune response in the lung of the subject.

In some embodiments, the presently disclosed subject matter also relates to methods for reducing TCR signal transduction in a lung of a subject. In some embodiments, the methods comprise administering to a subject a composition comprising at least one eosinophil recruiting agent, wherein the administering enhances recruitment of eosinophils to the lung of the subject to thereby reduce TCR signal transduction in the lung of the subject. In some embodiments, the administering inhibits proliferation of CD8$^+$ T cells in the lung of the subject. In some embodiments, the administering enhances expression of an inducible nitric oxide synthase (iNOS) gene product in the lung of the subject to thereby reduce TCR signal transduction in the lung of the subject. In some embodiments, the expression of the iNOS gene product is enhanced in an eosinophil present in the lung of the subject, optionally a Th1-polarized eosinophil present in the lung of the subject.

In some embodiments of any or all of the methods disclosed herein, the subject is a human.

Accordingly, it is an object of the presently disclosed subject matter to provide methods for modulating immune responses in the lungs, optionally wherein the immune responses are associated with one or more biological activities of eosinophils present in and/or recruited to the lungs.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) Seven days after transplantation of BALB/c lung allograft to B6 recipient with or without CSB immunosuppression, the whole lung allograft (left) or flow cytometrically sorted lung-resident eosinophils (center and right) were phenotyped for Th1 or Th2 polarization using established markers. Comparison was made to E0 resting blood-resident eosinophils (white) or eosinophils polarized to the E1 (Th1) phenotype by overnight exposure to IFN-γ and TNF-α (yellow) or E2 (Th2) phenotype by overnight exposure to IL-33, IL-4, and GM-CSF (gray). Representative of 4 to 6 transplants per group, with Th2 analysis presented in FIGS. 8A-8C. (FIG. 1B) Flow cytometric analysis of lung-resident eosinophils in BALB/c to B6 lung allografts with (blue) or without (red) CSB. Analysis of eosinophils from resting, untransplanted, B6 lungs shown as black line, while isotype control is shaded in gray. Representative of 3 to 5 separate transplants. (FIG. 1C) Histologic and flow cytometric analysis of BALB/c to iPhil transplants depleted of eosinophils with treatment by DT or saline control. Representative histologic section (top) and ISHLT A grade of rejection (bottom). Scale bar: 100 μm. (FIGS. 1D and 1E) Total number of graft-resident T cells (FIG. 1D top) and a representative plot of flow cytometrically analyzed lung digest defining CD8$^+$ T cells as CD90$^+$CD8$^+$ (FIG. 1E top). Total number of proliferating Ki-67$^+$ T cells (FIG. 1D middle) and a representative plot of Ki-67$^+$CD8$^+$ T cells (FIG. 1E middle). Relative proportion of effector T cells (defined as CD44$^{hi}$CD62L$^{lo}$; FIG. 1D bottom) and a representative plot of CD8$^+$ T cell effector differentiation (FIG. 1E bottom). All statistics performed by Mann-Whitney U test. *: $p<0.05$; **: $p<0.01$; NS: $p>0.05$.

(FIG. 2A) Graphic representation of the relationship among samples of the same group and the difference between the two groups of samples, based on the principle component analysis of the top 500 genes, selected by highest row variance. (FIG. 2B) Three of the top gene clusters upregulated in lung allograft-resident CD8$^+$ T cells in eosinophil-deficient B6 recipients of Balb/c lungs as determined by gene ontology analysis using GeneSCF software. (FIG. 2C) Detailed heat maps defining the relative levels of the top fifteen genes in the inflammatory response, immune system process and regulation of cell proliferation pathways defined as part of gene ontology analysis.

(FIG. 3A) In vitro MLR established using anti-CD3/CD28 DYNABEAD® stimulation of B6 T cells with varying ratios of E1 polarized B6 eosinophils added to the culture. Graph demonstrated percent proliferation, as defined by dilution of the cell trace violet (CTV) proliferation dye and effector differentiation, as defined by percentage of CD44$^{hi}$CD62L$^{low}$ CD8$^+$ T cells after 5 days of co-culture. Representative data from one out of three similar experiments. (FIG. 3B) Proliferation and effector differentiation of B6 CD8$^+$ T cells stimulated by Balb/c dendritic cells in a co-culture with a 2:1 ratio of eosinophils. For some conditions wild-type or iNOS$^{-/-}$ eosinophils were added directly to the dendritic cell/T cell co-cultures while in other conditions the eosinophils were separated from the dendritic cell/T cell co-cultures by a semi-permeable membrane. Summary of data shown on left and representative flow cytometry plots on the right. Representative data from one out of three similar experiments. (FIG. 3C) MLRs, similar to those demonstrated in panel A were set up except E1 polarized eosinophils were removed from the culture after 24 hours and T cell proliferation was analyzed on day 5 of the MLR. Summary of data on left and representative flow cytometry plot on the right. All statistics performed by Mann Whitney U test. $p<0.01$, *$p<0.001$ (FIG. 4A) In vitro MLRs established using the co-culture of bone marrow-derived Balb/c dendritic cells, B6 T cells with a 2:1 ratio of E1 polarized B6 eosinophils directly added to the culture. T cell viability was determined flow cytometrically after 5 days of co-culture with no, wild-type, or iNOS$^{-/-}$ eosinophils as described in the graph. Representative data from one out of three similar experiments. (FIG. 4B) In vitro MLRs established using the co-culture of anti-CD3/CD28 DYNABEADS® with Nur77 T cells and a 2:1 ratio of E1 polarized eosinophils. Nur77-driven GFP expression was used as a gauge of TCR stimulation in CD8$^+$ T cells after 36 hours of co-culture with no, wild-type, or iNOS$^{-/-}$ eosinophils. Demonstrating one out of three separate experiments. (FIG. 4C) Evaluation of the TCR/CD3 complex integrity by quantification of TCRβ immunoprecipitations with co-associated CD3ζ or CD3ε on CD8$^+$ T cells isolated from in vitro MLRs in the presence of no eosinophils (grey) vs. wild-type (red line) or iNOS$^{-/-}$ eosinophils (black line). Data representative of one out of five mice. All statistics performed by Mann Whitney U test. $p<0.01$, *$p<0.001$ (FIG. 5A) In vitro MLRs established using the co-culture of bone marrow-derived Balb/c dendritic cells or anti-CD3/CD28 DYNABEADS®, fluorescently-labeled CD8$^+$ and CD4$^+$ B6 T cells with a 2:1 ratio of E1 polarized fluorescently labeled B6 eosinophils and eosinophil/T cell interactions were analyzed using HARMONY™ Software. Yellow circles in the top graphic representation demonstrate HARMONY™ Software-detected T cell-eosinophil interactions which are quantitated in graphic form at the bottom. (FIG. 5B) Quantification of T cell-eosinophil interaction during 16 hours of co-culture in vitro as determined by HARMONY™ Software analysis of live confocal microscopy. (FIG. 5C) PD-1 expression in CD4 and CD8$^+$ T cells of resting and transplanted murine lungs in vivo. Graphic representation at the top and quantification of % of T cells expressing PD-1 at the bottom. (FIG. 5D) PD-1 expression on T cells in in vitro MLRs stimulated with anti-CD3/CD28 DYNABEADS® in the presence or absence of wild-type eosinophils. (FIG. 5E) CD8$^+$ T cell-eosinophil interactions in the presence of PD-L1 blockade during 16 hours of co-culture in vitro as determined by HARMONY™ Software analysis of live confocal microscopy. (FIG. 5F) CD8$^+$ T cell proliferation and effector differentiation in the presence or absence of eosinophils and PD-L1 blockade in in vitro MLRs with anti-CD3/CD28 DYNABEAD® stimulation. All MLRs in FIGS. 5A-5F demonstrate one experiment from two to three. (FIG. 5G) Image-stream analysis of eosinophil-T cell MLRs for surface analysis of PD-L1 expression and polarization. All statistics performed by Mann Whitney U test. *$p<0.05$, $p<0.01$, *$p<0.001$, ns $p>0.05$.

(FIG. 6A) In vitro MLRs established using the co-culture of fluorescently-labeled bone marrow-derived Balb/c dendritic cells, fluorescently-labeled CD8$^+$ and CD4$^+$ B6 T cells with a 2:1 ratio of E1 polarized fluorescently labeled B6 eosinophils. Eosinophil/T cell/dendritic cell interactions were analyzed using HARMONY™ Software with graphic representation at the top with yell circles representing interactions. Bottom panel represents the number of eosinophil contacts with CD4$^+$ or CD8$^+$ T cells or dendritic cells. Data representative of two separate experiments. (FIG. 6B) Balb/c lung were engrafted into B6iPHIL mice treated with DT (eosinophil deficient) or saline (eosinophil sufficient). The phenotype of CD11c$^+$ CD64$^+$ interstitial macrophages and CD103$^+$ dendritic cells was evaluated flow cytometrically in engrafted lungs in the presence of the full complement of T lymphocytes (left panels) or after depletion of both CD4$^+$ and CD8$^+$ T cells (right panel). Representative of two separate sets of transplants. All statistics performed by Mann Whitney U test. ***$p<0.001$.

FIGS. 7A-7C: Rejection of Balb/c to B6 lung grafts treated with intratracheal eotaxin 1,2 and IL-5. Balb/c lungs were transplanted into B6 recipients which were treated with an intratracheal chemokine and cytokine cocktail of eotaxin1,2 and IL-5 immediately after engraftment and on post-operative day number one. Lung grafts were evaluated flow cytometrically and histologically on post-operative day seven for rejection (FIG. 7A), total eosinophil content (FIG. 7B) and CD8$^+$ T cell differentiation (FIG. 7C). Histologic analysis for ISHLT grade of rejection was performed on H+E stained slides and eosinophil peroxidase immunohistochemistry was performed to evaluate eosinophil orientation in the tissue (eosinophils stained red). Line marker on histology and immunohistochemistry indicates 100 μl. All statistics performed by Mann Whitney U test. *$p<0.05$.

(FIG. 8A) Seven days after transplantation of Balb/c lung allograft to B6 recipient with or without CSB immunosuppression the whole lung allograft (left) or flow cytometrically sorted lung-resident eosinophils (right) were phenotyped for Th1 or Th2 polarization using established markers. Comparison was made to E0 resting blood resident eosinophils (white) or eosinophils polarized to the E1 (Th1) phenotype by overnight exposure to IFN-g and TNF-a (yellow) or E2 (Th2) phenotype by overnight exposure to IL-33, IL-4 and GMCSF (grey). Representative of 4-6 transplants per group with Th1 analysis presented in FIG. 1. Representative of 4-6 transplants per group. (FIG. 8B) Flow cytometric analysis of lung resident eosinophils from Balb/c to B6 lung grafts for donor-specific MHC I (H2Kd) and MHC II (IAd). Representative of 3-5 separate transplants. (FIG. 8C) Representative lung digest (top) and quantitative analysis of iPHIL mouse treated with saline (right sided panel) or DT (left sided panel) for flow cytometric quantification of eosinophils.

(FIG. 9A) Volcano plot demonstrating the 2956 genes upregulated and the 2360 genes downregulated in CD8$^+$ T cells from eosinophil deficient compared to sufficient lung grafts. (FIG. 9B) Ontogeny cluster analysis of the gene expression pattern of CD8$^+$ T cells from eosinophil deficient compared to eosinophil sufficient lung grafts.

(FIG. 10A) In vitro MLR established using anti-CD3/CD28 DYNABEAD® stimulation of B6 T cells with varying ratios of E1 polarized B6 eosinophils added to the culture. Graph demonstrated percent proliferation, as defined by dilution of the cell trace violet (CTV) proliferation dye of CD4$^+$ T cells after 5 days of co-culture. Representative data from one out of three similar experiments. (FIG. 10B) Proliferation of B6 CD4$^+$ T cells stimulated by Balb/c dendritic cells in a co-culture with a 2:1 ratio of eosinophils. For some conditions wild-type or iNOS−/− eosinophils were added directly to the dendritic cell/T cell co-cultures while in other conditions the eosinophils were separated from the dendritic cell/T cell co-cultures by a semi-permeable membrane. Representative data from one out of three similar experiments.

(FIG. 11A) Proliferation of CD8$^+$ T cells stimulated by Balb/c dendritic cells in a co-culture with a 2:1 ratio of eosinophils and 100 U/ml of IL-2. (FIG. 11B) GFP expression as a gauge of Nur77/TCR stimulation in CD4 T cells after 36 hours of co-culture with no, wild-type, or iNOS$^{-/-}$ eosinophils. All statistics performed by unpaired Mann Whitney U test. ns p>0.05 ***p<0.001. (FIG. 11C) Transcript level of Nur77 in CD8$^+$ T cells from day 7 Balb/c to B6 lung allografts in eosinophil deficient or eosinophil sufficient microenvironment, determined by RNAseq. p<0.00001; adj.p<0.001.

(FIG. 12A) MHC class I (MHC-I), PD-L1, ICAM-1, ICAM-2 and LFA-1 expression in wild-type and iNOS$^{-/-}$ eosinophils before (E0) and after (E1) polarization in vitro. (FIG. 12B) CD8$^+$ T cell-eosinophil interactions in the presence of CD11b blockade during 16 hours of co-culture in vitro as determined by live confocal microscopy. (FIG. 12C) CD4$^+$ T cell proliferation and effector differentiation in the presence or absence of PD-1 blockade in in vitro MLRs.

(FIG. 14A) Flow cytometric and histologic analysis of Balb/c to B6CD45.1$^+$ lung transplants with (right panel) or without (left panel) adoptive transfer of 15×10$^6$ CD45.2$^+$; eosinophils at the time of transplantation and on post-operative day 1. Representative of two separate transplants. (FIG. 14B) Balb/c lungs were transplanted into B6 recipients which were treated with an intratracheal chemokine and cytokine cocktail of eotaxin 1,2 and 1-5 immediately after engraftment and on post-operative day number one. Lung grafts were evaluated flow cytometrically for number of CD8$^+$ T cells on post-operative day seven.

(FIG. 15A) Quantitative RT-PCR reveals a significant increase in iNOS transcript levels seven days after transplantation of Balb/c lungs to B6 recipients with CSB-immunosuppression. (FIG. 15B) Flow cytometric analysis demonstrated that lung allografts are infiltrated by iNOS' hematopoietic cells. Represents 8 separate transplants. (FIG. 15C) Time-course analysis demonstrates a gradual increase in iNOS$^+$ cells which decrease to baseline levels one month post-transplantation (representative of at least four transplants per time point). (FIG. 15D) Transplantation of a Balb/c$^{CD45.2+}$ lung grafts to a B6$^{CD45.1+}$ recipient demonstrates that all iNOS' graft infiltrating cells are of recipient origin. Representative of three separate transplants (*=p<0.05, **=p<0.01)

(FIG. 16B) iNOS$^+$ cells in Balb/c to B6 lung transplantation with CSB immunosuppression (representative of seven transplants), and (FIG. 16C) Cytospin preparation and Romanowsky staining of iNOS$^+$ cells in accepting lung grafts, demonstrate an eosinophil phenotype.

(FIG. 17B) Quantitative analysis of eosinophils in resting B6 and Balb/c mice, and Balb/c to B6 lung transplantation with CSB or CsA/MP immunosuppression as a percentage (left panel) and total number of lung-resident cells (right panel). (**=p<0.01).

(FIG. 18A) Recipient IL-5 neutralization virtually eliminates all eosinophils in the lung allograft with minimal impact on other cell types. (FIG. 18B) IL-5 neutralization also eliminates iNOS expressing graft-resident cells and (FIG. 18C) reduces lung graft NO production to levels statistically comparable to B6$^{iNOS-/-}$ recipients. (FIG. 18D) Depletion of eosinophils results in lung allograft rejection as measured by gross changes (top left), histologic evidence of inflammation (bottom left) and ISHLT grade (right). (ns=p>0.05, =p<0.01, *=p<0.001)

(FIG. 19A) Gene expression analysis of lungs demonstrates a Th1 like polarization four days after transplantation. Representative of six separate transplants with Balb/c to B6 allografts in blue, Balb/c resting lungs white and B6 resting lungs black dots. (FIG. 19B) Eosinophils flow cytometrically sorted from Balb/c to B6 lung grafts seven days after transplantation with CSB immunosuppression demonstrate an E1-like gene fingerprint pattern that resembles that of eosinophils exposed to IFN-γ and TNF-α ex vivo. Data from 5 separate transplants (=p<0.01, *=p<0.001)

(FIG. 21A) Proliferation, as measured by Ki67 expression among B6$^{CD45.1+}$ CD8$^+$ T cells activated with Balb/c allogenic splenocytes with or without the addition of E1 or E0 eosinophils. (FIG. 21B) In vitro differentiation, as measured by CD44 and CD62L expression on B6M$^{CD45.1+}$ CD8$^+$ T cells stimulated by Balb/c allogenic splenocytes with or without the addition of E1 or E0 eosinophils. (FIG. 21C) iNOS expression in CD8$^+$ T cells activated with Balb/c allogenic splenocytes with or without the addition of IFN-γ and TNF-α blocking antibodies. Representative experiment of four separate MLRs. (FIG. 21D) Modulation of CD8$^+$ T cell proliferation by E0 and E1 eosinophil in MLR of Balb/c allogenic splenocytes stimulators with IFN-γ and TNF-αc blockade. (FIG. 21E) Schematic representation of regulatory feedback loop between alloreactive lymphocytes and eosinophils in lung grafts. (ns=p>0.05, **=p<0.01)

(FIG. 22A) CD101 and CD62L levels in eosinophils from resting B6 and Balb/c to B6 lung grafts. (FIG. 22B) Relative expression of IL-27 and CXCL13 levels in eosinophils isolated from peripheral blood and lungs of accepting Balb/c to B6 lung grafts. (FIG. 22C) Rejection, as measured by gross appearance (top), histology (middle) and ISHLT grade (bottom) of B6 to ΔdblGATA and B6 to Balb/c mice with CSB.

DETAILED DESCRIPTION

Figure 1A:
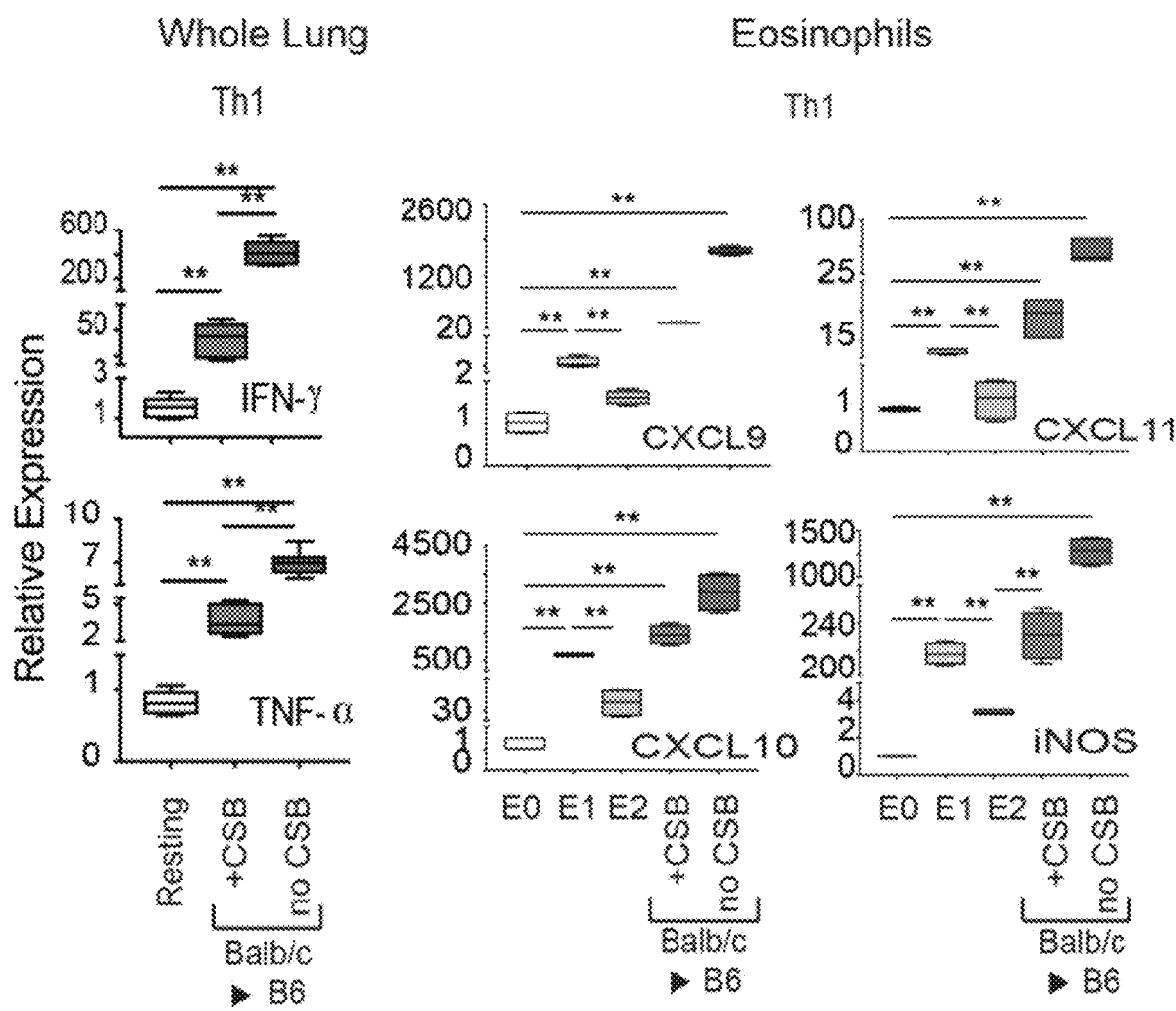
FIGS. 1A-1E: Th-1 polarization of the lung allograft.

The presently disclosed subject matter demonstrates that eosinophils, a granulocytic population long considered deleterious for long-term graft function, play a critical role in co-stimulatory blockade (CSB)-mediated induction of lung allograft tolerance. The role of this cell population in the absence of CSB or its mechanism of immunosuppression remain unknown. Herein is demonstrated that eosinophils play a unique role in the downregulation of the lung alloimmune response even in the absence of traditional or CSB-mediated immunosuppression. Thus, unlike the case for other solid organs (Goldman et al., 2001), eosinophils play a tolerogenic role in the lung allograft. Mechanistically, that Th1-polarized eosinophils inhibit $CD8^+$ T cell proliferation by interfering with T cell receptor (TCR/CD3) subunit association and signal transduction in an iNOS-dependent manner has been shown. It is further shown that PD-L1-dependent eosinophil-T cell contact plays a role in eosinophil suppressive function.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the phrase "biological sample" refers to a sample isolated from a subject (e.g., a biopsy, blood, serum, etc.) or from a cell or tissue from a subject (e.g., RNA and/or DNA and/or a protein or polypeptide isolated therefrom). Biological samples can be of any biological tissue or fluid or cells from any organism as well as cells cultured in vitro, such as cell lines and tissue culture cells. Frequently the sample will be a "clinical sample" which is a sample derived from a subject (i.e., a subject undergoing a diagnostic procedure and/or a treatment). Typical clinical samples include, but are not limited to cerebrospinal fluid, serum, plasma, blood, saliva, skin, muscle, olfactory tissue, lacrimal fluid, synovial fluid, nail tissue, hair, feces, urine, a tissue or cell type, and combinations thereof, tissue or fine needle biopsy samples, and cells therefrom. Biological samples can also include sections of tissues, such as frozen sections or formalin fixed sections taken for histological purposes.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter. By way of example and not limitation, a pharmaceutical composition comprising a particular active agent and a pharmaceutically acceptable carrier can also contain other components including, but not limited to other active agents, other carriers and excipients, and any other molecule that might be appropriate for inclusion in the pharmaceutical composition without any limitation.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause, other elements are not excluded from the claim as a whole. By way of example and not limitation, a pharmaceutical composition consisting of a active agent and a pharmaceutically acceptable carrier contains no other components besides the particular active agent and the pharmaceutically acceptable carrier. It is understood that any molecule that is below a reasonable level of detection is considered to be absent.

As used herein, the phrase "consisting essentially of" limits the scope of a claim to the specified materials or steps, plus those that do not materially affect the basic and novel characteristic(s) of the claimed subject matter. By way of example and not limitation, a pharmaceutical composition consisting essentially of an active agent and a pharmaceutically acceptable carrier contains active agent and the pharmaceutically acceptable carrier, but can also include any additional elements that might be present but that do not materially affect the biological functions of the composition in vitro or in vivo.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

As used herein, the term "isolated" when referring to cells or a cell population refers to cells or a cell population collected from a subject, in some embodiments a mammalian subject, and in some embodiments a human. Typically, collection of the desired cells or cell population is achieved based on detection of one or more cell markers, such as but not limited to antibody-based detection.

tioned herein (e.g., IL-5, eotaxin, eotaxin 2, iNOS, etc.) and for which Accession Nos. for various exemplary gene products disclosed in the GENBANK® biosequence database for the human gene products are disclosed herein below, are intended to encompass homologous and variant genes and gene products from humans and other animals including, but not limited to other mammals.

Exemplary GENBANK ® Accession Nos. for Various Human Gene Products

| Gene Symbol | Nucleic Acid Accession No. | Amino Acid Accession No. |
| --- | --- | --- |
| Interleukin-5 | NM_000879.3 (SEQ ID NO: 1) | NP_0000870.1 (SEQ ID NO: 2) |
| Eotaxin (CCL11) | NM_002986.3 (SEQ ID NO: 3) | NP_002977.1 (SEQ ID NO: 4) |
| Eotaxin 2 (CCL24) | NM_002991.3 (SEQ ID NO: 5) | NP_002982.2 (SEQ ID NO: 6) |
| iNOS | NM_000625.4 (SEQ ID NO: 35) | NP_000616.3 (SEQ ID NO: 36) |

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein. In some embodiments, a subject is a human.

Similarly, all genes, gene names, and gene products disclosed herein are intended to correspond to orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, the genes specifically men- The methods of the presently disclosed subject matter are particularly useful for warm-blooded vertebrates. Thus, the presently disclosed subject matter concerns mammals and birds. More particularly contemplated is the isolation, manipulation, and use of stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of stem cells from livestock, including but not limited to domesticated swine (pigs and hogs), ruminants, horses, poultry, and the like.

As used herein, the phrase "substantially" refers to a condition wherein in some embodiments no more than 50%, in some embodiments no more than 40%, in some embodiments no more than 30%, in some embodiments no more than 25%, in some embodiments no more than 20%, in some embodiments no more than 15%, in some embodiments no more than 10%, in some embodiments no more than 9%, in some embodiments no more than 8%, in some embodiments no more than 7%, in some embodiments no more than 6%, in some embodiments no more than 5%, in some embodiments no more than 4%, in some embodiments no more than 3%, in some embodiments no more than 2%, in some embodiments no more than 1%, and in some embodiments no more than 0% of the components of a collection of entities does not have a given characteristic.

As used herein, the phrase "cell surface marker" refers not only for a protein expressed on the surface of a cell but also any carbohydrate, lipid, or any other target that is detectable using specific antibodies or any other standard detection method.

The phrase "intracellular marker" as used herein refers to any gene or intracellular gene product that is detectable.

The phrase "expression of [gene X]" as used herein when referring to a cell indicates that the cell expresses a transcription and/or translation product of that gene at a level that is sufficient for detection using standard detection methods. Expression of a gene product is also referred to as "positively expressing", "+", "positive", or "pos". The terms "not expressing [gene X]" as used herein when referring to a cell indicates that the cell does not express a transcription and/or translation product of that gene at a level that is sufficient for detection using standard detection methods. Absence of expression of a gene product is also referred to as "negative expression", "−", "negative", and "neg".

For some markers, expression or absence of expression is often in fact based on comparison with other cells which also express the marker. For these markers determining positive or negative expression is based on a threshold. Methods for determining positive or negative expression based on thresholds are known to the person skilled in the art and typically involve calibrating based on a "negative control". Accordingly, it will be understood that for these markers, reference to positive expression in fact implies "elevated expression compared to negative controls" and "negative expression" in fact refers to "reduced expression compared to positive controls".

When referring to a cell population, reference is made to a population which "expresses [gene X]" where at least 10%, 20%, or 30% or 40%, 50%, or 60% or 70%, 80%, or 90% or 95%, 96%, 97%, 98%, 99%, or even 100% of the cells within the population express the cell markers of interest. By "substantially free" is intended less than about 25%, 20%, 15%, 10%, 9%, 8%, 7%, 6%, 5%, 4%, 3%, 2%, 1%, or even 0% of the cells in the population express the marker of interest.

The terms "additional therapeutically active compound" or "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the presently disclosed subject matter or a prodrug thereof to a subject in need of treatment.

As used herein, "alleviating a disease or disorder symptom," means reducing the severity of the symptom or the frequency with which such a symptom is experienced by a subject, or both.

As used herein, the terms "biologically active fragment" and "bioactive fragment" of a peptide encompass natural and synthetic portions of a longer peptide or protein that are capable of specific binding to their natural ligand and/or of performing a desired function of a protein, for example, a fragment of a protein of larger peptide which still contains the epitope of interest and is immunogenic.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" refers to an amount of a compound or composition sufficient to produce a selected effect, such as but not limited to alleviating symptoms of a condition, disease, or disorder. In the context of administering compounds in the form of a combination, such as multiple compounds, the amount of each compound, when administered in combination with one or more other compounds, may be different from when that compound is administered alone. Thus, an effective amount of a combination of compounds refers collectively to the combination as a whole, although the actual amounts of each compound may vary. The term "more effective" means that the selected effect occurs to a greater extent by one treatment relative to the second treatment to which it is being compared.

A "fragment", "segment", or "subsequence" is a portion of an amino acid sequence, comprising at least one amino acid, or a portion of a nucleic acid sequence comprising at least one nucleotide. The terms "fragment", "segment", and "subsequence" are used interchangeably herein.

As used herein, a "functional" biological molecule is a biological molecule in a form in which it exhibits a property by which it can be characterized. A functional enzyme, for example, is one that exhibits the characteristic catalytic activity by which the enzyme can be characterized.

As used herein, the term "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

The term "pharmaceutical composition" refers to a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Pharmaceutically acceptable" means physiologically tolerable, for either human or veterinary application. Similarly, "pharmaceutical compositions" include formulations for human and veterinary use.

As used herein, the term "pharmaceutically acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" refers to non-naturally occurring peptides or polypeptides. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition. It is noted that "prevention" need not be absolute, and thus can occur as a matter of degree.

A "preventive" or "prophylactic" treatment is a treatment administered to a subject who does not exhibit signs, or exhibits only early signs, of a condition, disease, or disorder. A prophylactic or preventative treatment is administered for the purpose of decreasing the risk of developing pathology associated with developing the condition, disease, or disorder.

"Primer" refers to a polynucleotide that is capable of specifically hybridizing to a designated polynucleotide template and providing a point of initiation for synthesis of a complementary polynucleotide (e.g., polymerization). Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. In some embodiments, primers can be labeled, e.g., with chromogenic, radioactive, and/or fluorescent moieties and used as detectable moieties.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process.

A "highly purified" compound as used herein refers to a compound that is in some embodiments greater than 90% pure, that is in some embodiments greater than 95% pure, and that is in some embodiments greater than 98% pure.

As used herein, the term "mammal" refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection. For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters. In some embodiments, a percent identity is calculated over the full length of one or both of the two sequences being compared.

Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (e.g., GAP, BESTFIT, FASTA, and TFASTA), or by visual inspection. See generally, Ausubel et al., 1992.

An exemplary algorithm for determining percent sequence identity and sequence similarity is the BLAST algorithm, which is described in Altschul et al., 1990a. Software for performing BLAST analyses is publicly available through the website of the United States National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

The term "polynucleotide" as used herein includes but is not limited to DNA, RNA, complementary DNA (cDNA), messenger RNA (mRNA), ribosomal RNA (rRNA), small hairpin RNA (shRNA), small nuclear RNA (snRNA), short nucleolar RNA (snoRNA), microRNA (miRNA), genomic DNA, synthetic DNA, synthetic RNA, and/or tRNA.

As used herein, a "subject in need thereof" is a patient, animal, mammal, or human, who will benefit from the methods of the presently disclosed subject matter.

As used herein, "substantially homologous amino acid sequences" includes those amino acid sequences which have in some embodiments at least about 95% homology, in some embodiments at least about 96% homology, in some embodiments at least about 97% homology, in some embodiments at least about 98% homology, and in some embodiments at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the presently disclosed subject matter.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In some embodiments, the substantially identical nucleic acid sequence encodes the peptide encoded by the reference nucleic acid sequence. The percentage of identity between the substantially similar nucleic acid sequence and the reference nucleic acid sequence is in some embodiments at least about 50%, 65%, 75%, 85%, 95%, 99%, or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: in some embodiments in 7% sodium dodecyl sulfate SDS, 0.5 M NaPO$_4$, 1 mM EDTA at 50° C. with washing in 2× standard saline citrate (SSC), 0.1% SDS at 50° C.; in some embodiments in 7% (SDS), 0.5 M NaPO$_4$, 1 mM EDTA at 50° C. with washing in 1×SSC, 0.1% SDS at 50° C.; in some embodiments in 7% SDS, 0.5 M NaPO$_4$, 1 mM EDTA at 50° C. with washing in 0.5×SSC, 0.1% SDS at 50° C.; and in some embodiments in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984), and the BLASTN or FASTA programs (Altschul et al., 1990a,b; Altschul et al., 1997). The default settings provided with these programs are suitable for determining substantial similarity of nucleic acid sequences for purposes of the presently disclosed subject matter.

The term "substantially pure" describes a compound, e.g., a protein or polypeptide, which has been separated from components which naturally accompany it. Typically, a compound is substantially pure when in some embodiments at least 10%, in some embodiments at least 20%, in some embodiments at least 50%, in some embodiments at least 60%, in some embodiments at least 75%, in some embodiments at least 90%, and in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse, and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

II. Methods and Compositions of the Presently Disclosed Subject Matter

In some embodiments, the presently disclosed subject matter relates to methods for enhancing immunosuppression in the lung(s) of subject(s) in need thereof. As used herein, the phrase "enhancing immunosuppression" refers to any enhancement of a subject to accept a transplanted lung, which in some embodiments can be an allogenic transplanted lung. Stated another way, "enhancing immunosuppression" refers in some embodiments to reducing the immune response in a subject against a transplanted lung.

In some embodiments, a method of enhancing immunosuppression can comprise administering to a subject in need thereof a composition comprising at least one eosinophil recruiting agent, wherein the administering is in an amount and via a route of administration sufficient to induce recruitment of eosinophils to the lung of the subject to thereby enhance immunosuppression in the lung of the subject. As used herein, the phrase "eosinophil recruiting agent" refers to any agent that when administered to a subject, results in the accumulation of eosinophils in the lung of the subject to a greater degree than would have occurred had the eosinophil recruiting agent not been administered to the subject. Any molecule that results in such an accumulation of eosinophils in the lung of the subject can be employed in the methods of the presently disclosed subject matter. For example, as disclosed herein interleukin-5 (IL-5) and the eotaxins are known to attract eosinophils, and if administered to the lungs can result in accumulation of eosinophils in the lung. Other exemplary, non-limiting eosinophil recruiting agents include platelet activating factor (PAF; 1-O-alkyl-2-acetyl-sn-glycero-3-phosphocholine) and certain eicosanoids, including leukotriene $B_4$, cysteinyl leukotrienes, and prostaglandin $D_2$.

The presently disclosed subject matter thus provides in some embodiments methods for enhancing immunosuppression in the lung(s) of subject(s) comprising administering to the subject(s) a pharmaceutical composition, wherein the pharmaceutical composition comprises one or more eosinophil recruiting agents in any combination thereof, optionally wherein the one or more eosinophil recruiting agents are provided in a pharmaceutically acceptable carrier, in an amount and via a route sufficient to allow the one or more eosinophil recruiting agents to recruit sufficient eosinophils into the lung(s) of the subjects to enhance immunosuppression in the lung(s) of the subjects.

In some embodiments, the presently disclosed subject matter also relates to methods for enhancing tolerance to a lung transplant in a subject. In some embodiments, the methods comprise administering to the subject a composition comprising at least one eosinophil recruiting agent, wherein the administering is in an amount and via a route of administration sufficient to induce recruitment of eosinophils to the lung of the subject to thereby enhance tolerance to the lung transplant in the subject. In some embodiments, the at least one eosinophil recruiting agent is administered to the subject in one or more doses concurrently with and/or subsequent to the lung transplant being introduced into the subject. In some embodiments, the lung transplant is allogenic to the subject. Unlike in most transplant procedures, in some embodiments of the presently disclosed methods, the subject is an otherwise non-immunosuppressed subject.

Approaches to determine and extent of immunosuppression and/or transplant acceptance/rejection are known, and include but are not limited to those set forth in U.S. Patent Application Publication No. 2017/0114411 and U.S. Pat. Nos. 8,247,175; 8,637,232; and 10,000,809, the disclosure of each of which is incorporated herein by reference in its entirety.

Additionally, in some embodiments the presently disclosed subject matter thus relates to methods for enhancing recruitment of eosinophils to a lung of a subject. As used herein, the phrase "enhancing recruitment of eosinophils" refers to any intervention that, as compared to the same circumstances absent the intervention, results in a greater accumulation of eosinophils in the target organ (e.g., the lung). In some embodiments, enhancing recruitment of eosinophils to a lung of a subject is accomplished by administering to the subject a composition comprising at least one eosinophil recruiting agent, wherein the administering enhances recruitment of eosinophils to the lung of the subject. With respect to the presently disclosed methods, in some embodiments the lung is a transplanted lung.

Furthermore, in some embodiments the presently disclosed subject matter thus relates to methods for modulating a T cell-mediated immune response in a lung of a subject. The phrase "modulating a T cell-mediated immune response" refers to any intervention that, as compared to the same circumstances absent the intervention, results in a change in the degree, timing, or extent of a T cell mediated immune response in the target organ (e.g., the lung). In some embodiments, modulating a T cell-mediated immune response in the lung of a subject is accomplished by administering to the subject a composition comprising at least one eosinophil recruiting agent, wherein the administering enhances recruitment of eosinophils to the lung of the subject to thereby modulate the T cell-mediated immune response in the lung of the subject.

In some embodiments the presently disclosed subject matter also relates to methods for reducing TCR signal transduction in a lung of a subject. The phrase "reducing TCR signal transduction" refers to any intervention that, as compared to the same circumstances absent the intervention, results in a reduction in signal transduction through the T cell antigen receptor (TCR) in the lung of the subject. In some embodiments, a reduction in TCR signal transduction results in an enhancement of immunosuppression in the lung and/or a reduction in lung transplant rejection in the subject. In some embodiments, a reduction in TCR signal transduction in the lung of a subject is accomplished by administering to the subject a composition comprising at least one eosinophil recruiting agent, wherein the administering enhances recruitment of eosinophils to the lung of the subject to thereby reduce TCR signal transduction in the lung of the subject. In some embodiments, the administering inhibits proliferation of $CD8^+$ T cells in the lung of the subject. In some embodiments, the administering enhances expression of an inducible nitric oxide synthase (iNOS) gene product in the lung of the subject to thereby reduce TCR signal transduction in the lung of the subject. In some embodiments, the iNOS gene product is enhanced in an eosinophil present in the lung of the subject.

In some embodiments of the presently disclosed methods, the at least one eosinophil recruiting agent recruits eosinophils to the lung that are Th1-polarized eosinophils.

II.A. Formulations

Thus, in some embodiments the presently disclosed subject matter relates to compositions, in some embodiments pharmaceutical compositions, for use in the presently disclosed methods. In some embodiments, the pharmaceutical composition comprises an effective amount of an eosinophil recruiting agent or combinations thereof as set forth herein.

In some embodiments, an eosinophil recruiting agent or combinations thereof of the presently disclosed subject matter comprise be provided in a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The methods and compositions of the presently disclosed subject matter can be used with additional adjuvants or biological response modifiers including, but not limited to, cytokines and other immunomodulating compounds.

In some embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the compositions described herein. Drugs useful in the presently disclosed subject matter may, for example, possess a pharmaceutical property selected from the group consisting of antimitotic, antikinase, alkylating, antimetabolite, antibiotic, alkaloid, anti-angiogenic, pro-apoptotic agents, and combinations thereof.

In some embodiments, the presently disclosed compositions and methods can further comprise administering to the subject at least one additional immunosuppressive agent to a subject. In some embodiments, the at least one additional immunosuppressive agent is selected from the group consisting of methotrexate, cyclophosphamide, cyclosporine, cyclosporin A, chloroquine, hydroxychloroquine, sulfasalazine (sulphasalazopyrine), a gold salt, D-penicillamine, leflunomide, azathioprine, anakinra, infliximab (REMICADE), etanercept, a TNFα blocker, a non-steroidal anti-inflammatory drug (NSAID), or any combination thereof. In some embodiments, the NSAID is selected from the group consisting of acetyl salicylic acid, choline magnesium salicylate, diflunisal, magnesium salicylate, salalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, a cyclooxygenase-2 (Cox-2) inhibitor, tramadol, rapamycin (sirolimus), an analog thereof, or any combination thereof.

II.B. Administration

Suitable methods for administration of the compositions of the presently disclosed subject matter include, but are not limited to intravenous administration and delivery directly to the target tissue or organ (e.g., the lung). In some embodiments, the method of administration encompasses features for regionalized delivery or accumulation of the eosinophil recruiting agent(s) at the site in need of treatment. In some embodiments, the eosinophil recruiting agent(s) is/are delivered directly into the lung. In some embodiments, selective delivery of the eosinophil recruiting agent(s) is accomplished by intravenous injection of eosinophil recruiting agent(s), where they accumulate in the lung. Other modes of administration that can be employed include topical, oral, buccal, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. Compounds or agents of the presently disclosed subject matter can be administered to a subject by one or more of these routes when appropriate. In some embodiments, intratracheal installation, insufflation, nebulization, dry powder inhalation, aerosol inhalation, and combinations thereof are employed as a route or routes of administration of the eosinophil recruiting agent(s) of the presently disclosed subject matter.

Where the administration of the eosinophil recruiting agent(s) is by injection or direct application, the injection or direct application may be in a single dose or in multiple doses. Where the administration of the eosinophil recruiting agent(s) is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the presently disclosed subject matter may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 10% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Genaro, ed., 1985, *Remington's Pharmaceutical Sciences*, Mack Publishing Co., Easton, Pennsylvania, which is incorporated herein by reference.

II.C. Doses

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). In some embodiments, an activity that inhibits an anti-transplant immune response (e.g., transplant rejection) is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using generally applicable assay methods, one skilled in the art can readily assess the potency and efficacy of a candidate compound of the presently disclosed subject matter and adjust the therapeutic regimen accordingly. After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

As such, in some embodiments the presently disclosed eosinophil recruiting agent(s) thereof is/are present in a pharmaceutically acceptable carrier, which in some embodiments can be a pharmaceutically acceptable for use in humans.

Typically, dosages of the compound of the presently disclosed subject matter which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In one aspect, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Materials and Methods Employed in EXAMPLES 1-6

Animals.

C57BL/6$^{CD45.2+}$ (B6) (H2$^b$), B6.SJL/BoyJ(B6$^{CD45.1+}$) (H2$^b$), Balb/c (H2$^d$) and Nur-77 GFP (C57BL/6-Tg (Nr4a1EGFP/cre) 820Khog/J) mice were obtained from The Jackson Laboratory (Bar Harbor, Maine). iPHIL mice (expressing diphtheria toxin receptor on an eosinophil-peroxidase specific promoter) and hypereosinophilic IL-5 transgenic mice (NJ. 1638) were developed in at the Mayo Clinic (Scottsdale, AZ; Lee et al., 1997; Jacobsen et al., 2014a), bred, and maintained at the vivarium facility at the University of Virginia School of Medicine. For in vitro experiments iNOS$^{-/-}$ hypereosinophilic mice were generated by crossing the NJ1638 strain to the B6.129P2-Nos2$^{tm1Lau}$/J (iNOS$^{-/-}$) strain (Jackson Laboratory) for at least three generations. Such mice were then maintained as a colony by crossing the NJ1638 iNOS$^{-/-}$ strain to wild type iNOS$^{-/-}$ mice. The animals passed all necessary genotyping screening or quarantine serological tests for those that were transported from one University to the other, before they were used in this study. Mice used as donors were 5-8 weeks old males, those used as graft recipients in this study were also males at 2-4 months of age, while both male and female hypereosinophilic mice were used when they were 3-7 months old for eosinophil isolation.

Surgery and Transplantation.

Orthotopic transplantation of a left lung allograft was carried out according to our previous reports (Okazaki et al., 2007; Krupnick et al., 2009). To achieve allograft acceptance mice were treated either with double co-stimulatory blockade of the CD28/B7 and the CD40/CD40L pathways as previously described (Larsen et al., 1996).

Histology.

Lungs were fixed in formalin, sectioned and stained with Hematoxylin and Eosin (H+E). A lung pathologist blinded to the experimental conditions graded graft rejection using standard criteria (International Society for Heart and Lung Transplantation (ISHLT) A Grade) developed by the Lung Rejection Study Group (Yousem et al., 1996).

Immunohistochemistry.

Formalin-fixed lung tissues embedded in paraffin were sectioned, subjected to antigen retrieval and stained with either mouse anti-mouse eosinophil peroxidase and a secondary goat anti-mouse antibodies or rat-anti-mouse CD8 and a secondary donkey anti-rat antibodies for the detection of eosinophils or CD8$^+$ cells respectively as previously (Bradshaw et al., 2017; Jacobsen et al., 2017). The protocol for eosinophil detection included blocking with Dual Endogenous Blocking Solution (Dako) and Donkey serum respectively before incubation in the primary antibody, while horse serum was used for the initial blocking of the tissue slide for CD8 staining and detection.

Flow Cytometry.

For flow cytometric analysis lung tissue derived from resting or graft recipient mice was well minced with scissors and digested by placing it into RPMI 1640 medium (Thermo Fisher) containing 0.5 mg/ml collagenase II (Worthington Biochemical Corporation, Lakewood, New Jersey) and 5 U/ml DNAse (Sigma, St. Louis, Missouri) for 60 minutes at 37° C. in a shaker. The digested lung tissue was passed through a 70 µm cell strainer and treated with ACK lysing buffer (Lonza, Walkersville, Maryland) to remove red cell contamination. This digestion methods have been previously described (Onyema et al., 2017).

Measuring the subunit ratios within the TCR/CD3 complex via immunoprecipitation-flow cytometry (IP-FCM) was performed as previously described (Nagaraj et al., 2010). Briefly CD8+ T cells were purified from a 36-hour cultures where T cells were activated by plate-bound CD3/CD28 in the presence of no eosinophils, wild-type eosinophils or iNOS$^{-/-}$ eosinophils. For evaluation of the TCR complex the CD8+ T cells were lysed in 1% Digitonin isotonic lysis buffer, and post-nuclear lysates were incubated for IP with a monoclonal antibody specific for TCRβ (clone H57-597) to immunoprecipitate the native TCR/CD3 complexes. With the β-chain functioning to pull down the TCR such captured complexes were then probed in parallel with PE-conjugated monoclonal antibodies specific for CD3ζ (clone 6B10) or CD3ε (clone 2C11) for evaluation of TCR complex integrity.

All antibodies for flow cytometry were primarily fluorochrome-conjugated anti-mouse monoclonal antibodies, mostly derived from rat. Thus, staining of samples was by direct immunofluorescence. Intracellular staining was performed as previously described (Onyema et al., 2017). The following antibodies were purchased from BD Biosciences, (San Jose, California): anti iNOS FITC (clone 6/iNOS/NOS Type II), anti-PD-L1 PE or brilliant violet (BV)-421 (clone MIH5), and anti Siglec-F PE or PerCPCy5.5 (clone E50-2440). Antibodies purchased from Biolegend (San Diego, California) include anti CD68 alexa-488 or BV-421 (clone FA-11), anti CD206 FITC, APC or BV-421 (clone C068C5), anti CD64 PE-Cy7 (clone X54-5/7.1) and anti CCR3 PE or PE-Cy7 (clone J073E5), while the following antibodies were purchased from Thermo Fisher—eBiosciences (San Diego, California): anti CD45 eFluor-450 or eFluor-506 (clone 30-F11), anti CD45.2 eFluor-450 or eluor-506 (clone 104), anti CD45.1 APC-eFluor-780 or eFluour 506 (clone A20), anti CD11b FITC or APC-eFluor-780 (clone M1/70), anti CD86 PE or PE-Cy7 (clone GL1), anti CD80 APC or PE-Cy7 (clone 16-10A1), anti MHC-II (IA/IE) APC-eFluor-780 (clone M5/114.15.2), anti CD8a FITC, PerCPCy5.5 or APC-eFluor-780 (clone 53-6.7), anti CD90.2 FITC or APC-eFluor-780 (clone Thy-1.2), anti MHC-I (H2Kb) PE or APC (clone AF6-88.5.5.3), anti MHC-I (H2Kd) PerCP-eFluor710 (clone SF1-1.1.1), anti MHC-II (IA/IE) alexa-488 (clone M5/114.15.2), anti MHC-II (IA-b) PE (clone AF6-120.1), anti MHC-II (IA-d) APC (clone AMS-32.1), anti CD11c PerCPCy5.5 or eFluor-506 (clone N418), anti F4/80 FITC or PE (clone BM8), CD103 eFluor 450 (clone 2E7), anti PD-1 APC (clone J43), anti CD40 APC (clone 1C10), anti CD4 APC or eFluor 405 (clone RM4-5), anti CD44 PE or PerCPCy5.5 (clone IM7), anti CD62L PE-Cy7 (clone MEL-14), anti CD101 PE (clone Moushi 101), and anti Ki-67 PE (clone SolA15). All fluorochrome conjugated antibodies were matched with the corresponding IgG isotypes as antibody controls. In addition, FMO controls were also used to separate the negative and positive populations. Dead cells were excluded with Live/Dead Fixable Stain (Thermo Fisher). To block non-specific binding to Fc-receptors, we used anti CD16/CD32 (Thermo Fisher) (clone 93). Cells expressing various markers of interest were acquired either in a BD Canto II, equipped with three lasers for 10 parameters detection (BD Biosciences, San Jose, California). Quality controls were performed daily on the flow cytometers according to manufacturer's instruction. Analysis of flow cytometry data was done with FLOWJO™ Software, Version 10.

Image Cytometry.

IMAGESTREAM™ Mark II (Millipore Sigma, Burlington, Massachusetts) was used to visualize and study immune synapse formation between eosinophils and T cells. The procedure is as previously reported (Wabnitz et al., 2011), with slight modifications. Briefly a combination of purified T cells (stimulated with dendritic cells or anti-CD3/CD28 agonistic antibodies) and eosinophils were incubated for 24 hours to establish contacts. Cells were washed in 2% FBS in PBS and centrifuged at a low speed of 200 g for 4 minutes. Cells were fixed with BD CYTOFIX™ brand fixative buffer for 20 minutes and washed with BD PERM/WASH™ brand wash buffer at 200 g for 4 minutes. Cells were stained with a combination of rat anti mouse antibodies, including anti CD8 FITC (clone 53-6.7), anti PD-L1 PE (clone MIH5), and anti Siglec-F PerCpCy5.5 (clone E50-2440), and incubated for 30 minutes at 4° C. The cells were washed in BD PERM/WASH™ brand wash buffer at 200 g for 4 minutes and resuspended in 2% FBS in PBS for acquisition. Image data was visualized and analyzed with the IDEAS™ Software version 6.

Fluorescent Activated Cell Sorting for Lung Eosinophil.

Eosinophils were sorted as CD45+CD11b+Siglec-F+CD11c- cells following the staining of digested lungs with a panel of fluorochrome-conjugated antibodies similar to the ones used for flow cytometry. Sorting was done using the BD Influx (BD Biosciences).

Isolation, Culture, and Polarization of Mouse Peripheral Blood Eosinophils.

Eosinophils were isolated from peripheral blood of NJ.1638 or NJ1638 iNOS$^{-/-}$ strain after density dependent separation of the eosinophil-rich white blood cells using a combination of Histopaque 1119 and 1083 (Sigma-Aldrich) at a ratio of 1:9, followed by negative selection of >98% pure eosinophil population after incubation of white blood cells with a combination of CD45R/B220 and CD90.2/Thy-1.2 immunomagnetic beads (Miltenyi Biotech, San Diego, California). The purity of eosinophils was confirmed by flow cytometry (CD45+CD11b+Siglec-F+CD11c- cells). The details of the cell preparation and eosinophil purification protocol are as has been previously described (Jacobsen et al., 2015). For in vitro experiments purified eosinophils were cultured at 5×10$^5$/ml concentration for 18-24 hours in RMPI-1640 media (containing glutamine and 25 mM HEPES) (Thermo Fisher) supplemented with 10% FBS, 10 U/ml Penicillin, 10 µg/ml Streptomycin, 29.2 µg/ml L-Glutamine, and 55 µM β-mercaptoethanol. Eosinophils maintained in an unpolarized (E0) state were cultured with 10 ng/ml IL-5. Th-1 polarized eosinophils (E1) were cultured with 10 ng/ml IL-5, 15 ng/ml IFN-γ, and 15 ng/ml TNF-α, while Th-2 polarized eosinophils (E2) were cultured with IL-5 10 ng/ml, IL-33 30 ng/ml, IL-4 10 ng/ml, and GM-CSF 10 ng/ml. All cytokines and growth factors used for eosinophil polarization culture were recombinant proteins purchased from Peprotech (Rocky Hill, New Jersey).

In Vitro Mixed Leukocyte Reaction (MLR).

Bone marrow-derived dendritic cells (BMDCs; Helft et al., 2015) from Balb/cJ mice or anti-CD3/CD28 agonistic antibodies (DYNABEADS® or plate bound, ThermoFisher) were used to stimulate Thy 1.2 positive (CD90.2 positive) cells from B6, B6.SJL/BoyJ or Nur77$^{GFP}$ mice splenocytes. After careful titration, the volume of DYNABEADS® used was 5.0 µl for 1 ml of media containing 1×10$^6$ T cells. Such concentration resulted in 50-90% T cell proliferation after 5 days of culture. To prepare the coated plate used for a maximum of 48 hours culture, the concentration of soluble anti-CD3/CD28 agonistic antibodies used were 2.0 µg/ml anti-CD3 and 1.0 µg/ml anti-CD28 agonistic antibodies in PBS. 250 µl of the solution was used to coat one well of a 96-well round bottomed plate. The CD90.2$^+$ cells were obtained by positive selection with Manual activated Cell Separation (MACS) using Mouse CD90.2 MICROBEADS® (Miltenyi Biotech). In some experiments, where we needed to re-isolate CD8$^+$ T cells from the MLRs after culture, T cells were isolated from the splenocytes by negative selection using MOUSE PAN T CELL ISOLATION KIT II® (Miltenyi Biotech). CD90.2$^+$ cells or purified T cells were cultured together with the BMDCs in a round-bottomed 96-well plate at a ratio of 10:1 (T cells:BMDCs). In some experiments, eosinophils isolated from NJ1638 or NJ1638 iNOS$^{-/-}$ mice were also added to the culture at 2:1 eosinophil:T cell ratio or as stated herein below in the EXAMPLES. Cells were cultured at 37° C. with addition of 50% carbon dioxide. Proliferation of the T cells was analyzed flow cytometrically based on Ki-67 expression or dilution of Cell Trace Violet (CTV) after three or five days of culture as described in the text.

In Vitro Antibody-Mediated Protein Neutralization.

CD11b and PD-L1, were neutralized in vitro using 20 µg/ml of rat anti-mouse/human CD11b (clone M1/70) and 20 µg/ml rat anti-mouse PD-L1 (clone 10F.9G2; Bio X Cell), respectively. The proteins were added to the culture on set-up days.

Confocal Microscopy for Live Cell Imaging.

T cells, eosinophils and dendritic cells were separately labelled with a single fluorochrome cell surface antibody specific for each population or marker of interest at 20 µl of each antibody per 5×10$^6$ cells in 200 µl of the staining solution comprising 2% FBS in PBS. Cells were incubated at 4° C. and washed in the staining solution before the they were added to the MLR in a 96-well plate as follows: 5×10$^5$ T cells, 5×10$^5$ eosinophils, and 1×10$^5$ dendritic cells (when required). The rat anti-mouse antibodies used include: anti CD8 FITC (clone 53-6.7; Thermo Fisher), and anti-Siglec-F PE (clone E50-2440), anti CD4 alexa-647 or BV 421 (clone RM4-5), anti CD11b BV-421 (clone M1/70) and anti CD11c BV-421 (clone N418; BD Biosciences). Cells were cultured for 4 hours in the incubator at 37° C. and 5% carbon dioxide before the cultures were transferred into the confocal microscope, OPERETTA CLS™ (Perkin Elmer, Boston, Massachusetts), where the initial incubation conditions (37° C. and 5% carbon dioxide) were also maintained during live cell imaging and data acquisition. Data acquisition and analysis was done with HARMONY™ Software, version 4.5 (Perkin Elmer). To analyze eosinophil-T cell or eosinophil-DC contacts, the outer border of each cell population was established and a contact/fluorescent threshold was set after inspection based on the nearness or overlap of cells to one another measured as the intensity of detection of the fluorochrome signal of one cell in another cell type. All two cells separated by lower distances than the threshold were captured by the HARMONY™ Software.

Eosinophil Ablation.

Eosinophils were ablated in iPHI1 mice through intraperitoneal administration of Diptheria toxin (DT) (Millipore-Sigma) as described in (Jacobsen et al., 2014a). DT was reconstituted in PBS and administered at a dose of 15 ng/gm mouse at days −5, −4, −3, and +1 post-transplantation. Control mice received equivalent volume of vehicle.

In Vivo Antibody-Mediated Cytokine Neutralization.

All neutralization antibodies are of rat origin and purchased from Bio X cell, West Lebanon, New Hampshire. For the targeted depletion of eosinophils in allograft recipients, 200 µg of anti-mouse/human IL5 (clone TRFK5) was administered to each mouse on days −2, −1, +1, and +2 post-transplantation. For the depletion of T cells, 200 µg each of anti-mouse CD4 (clone GK 1.5) and anti-mouse CD8 (clone YTS 169.4) were administered together in a cocktail to each mouse on days −3, −1, and +1 post-transplantation. Each control animal for all the antibody mediated cell depletion experiments received an equivalent concentration of rat IgG control (clone HRPN).

In Vivo Eosinophil Mobilization.

This was achieved through the intra-tracheal administration of a combination the following recombinant proteins purchased from Peprotech: 3 µg recombinant mouse CCL11 (eotaxin), 3 µg recombinant mouse CCL24 (eotaxin 2) and 1 µg recombinant mouse IL-5 to each graft recipient immediately after transplant and on post-transplant day one. The chemokine/cytokine combination was given in 100 µl volume intratracheally.

Quantitative Polymerase Chain Reaction (qPCR).

RNA was extracted from lung digests, eosinophils isolated from the lung or in vitro polarized eosinophils using the TRIzol based technique according to manufacturer's guidelines (Thermo Fisher). cDNA was reverse-transcribed from RNA samples using the High Capacity cDNA Reverse Transcription Kit in accordance with manufacturer's instruction (Thermo Fisher—Applied Biosystem). qPCR was run on the cDNA samples using Power Syber Green PCR Master Mix (Thermo Fisher—Applied Biosystem) in a CFX-96 Real-Time PCR Detection System (Bio-Rad). Cycling and reaction conditions were as provided by the manufacturer. The sequences of the primers used were as follows:

| Gene | Forward Primer | Reverse Primer |
| --- | --- | --- |
| IFN-γ | ATGAACGCTACACACTGCATC (SEQ ID NO: 7) | CCATCCTTTTGCCAGTTCCTC (SEQ ID NO: 8) |
| TNF-α | CCCTCACACTCAGATCATCTTCT (SEQ ID NO: 9) | GCTACGACGTGGGCTACAG (SEQ ID NO: 10) |
| IL-5 | CTCTGTTGACAAGCAATGAGACG (SEQ ID NO: 11) | TCTTCAGTATGTCTAGCCCCTG (SEQ ID NO: 12) |

-continued

| Gene | Forward Primer | Reverse Primer |
|------|----------------|----------------|
| IL-33 | TCCAACTCCAAGATTTCCCCG (SEQ ID NO: 13) | CATGCAGTAGACATGGCAGAA (SEQ ID NO: 14) |
| IL-4 | GGTCTCAACCCCCAGCTAGT (SEQ ID NO: 15) | GCCGATGATCTCTCTCAAGTGAT (SEQ ID NO: 16) |
| GM-CSF | GGCCTTGGAAGCATGTAGAGG (SEQ ID NO: 17) | GGAGAACTCGTTAGAGACGACTT (SEQ ID NO: 18) |
| iNOS | GTTCTCAGCCCAACAATACAAGA (SEQ ID NO: 19) | GTGGACGGGTCGATGTCAC (SEQ ID NO: 20) |
| β-actin | CGTGCGTGACATCAAAGAG (SEQ ID NO: 21) | TGCCACAGGATTCCATAC (SEQ ID NO: 22) |
| CCL17 | TACCATGAGGTCACTTCAGATGC (SEQ ID NO: 23) | GCACTCTCGGCCTACATTGG (SEQ ID NO: 24) |
| IL-13 | CCTGGCTCTTGCTTGCCTT (SEQ ID NO: 25) | GGTCTTGTGTGATGTTGCTCA (SEQ ID NO: 26) |
| CXCL9 | GGAGTTCGAGGAACCCTAGTG (SEQ ID NO: 27) | GGGATTTGTAGTGGATCGTGC (SEQ ID NO: 28) |
| CXCL10 | CCAAGTGCTGCCGTCATTTTC (SEQ ID NO: 29) | GGCTCGCAGGGATGATTTCAA (SEQ ID NO: 30) |
| CXCL11 | GGCTTCCTTATGTTCAAACAGGG (SEQ ID NO: 31) | GCCGTTACTCGGGTAAATTACA (SEQ ID NO: 32) |
| CCL22 | AGGTCCCTATGGTGCCAATGT (SEQ ID NO: 33) | CGGCAGGATTTTGAGGTCCA (SEQ ID NO: 34) |

Sample Preparation and RNA Extraction.

RNA was extracted from CD8$^+$ T cells isolated from left lung allografts of either eosinophil depleted or non-depleted B6 recipients of Balb/c left lung grafts on post transplantation day 4, using the TRIzol based technique according to manufacturer's guidelines (Thermo Fisher).

RNA Library Preparation Via polyA Selection and Multiplexing of Mus musculus.

RNA samples were quantified using Qubit 2.0 Fluorometer (Thermo Fisher—Life Technologies) and RNA integrity was checked with 2100 Bioanalyzer (Agilent Technologies, Palo Alto, California). RNA library preparations, sequencing reactions, and initial bioinformatics analysis were conducted at GENEWIZ, LLC. (South Plainfield, New Jersey). RNA sequencing library preparation used the NEBNEXT® ULTRA™ RNA Library Prep Kit for ILLUMINA® by following manufacturer's recommendations (NEB, Ipswich, Massachusetts). Briefly, mRNA was first enriched with Oligod(T) beads. Enriched mRNAs were fragmented for 15 minutes at 94° C. First strand and second strand cDNA were subsequently synthesized. cDNA fragments were end repaired and adenylated at the 3'-ends, and a universal adapter was ligated to the cDNA fragments followed by index addition and library enrichment with limited cycle PCR. Sequencing libraries were validated using a DNA Chip on the Agilent 2100 Bioanalyzer (Agilent Technologies, Palo Alto, California), and quantified by using QUBIT® 2.0 Fluorometer (Thermo Fisher—Invitrogen) as well as by quantitative PCR (Thermo Fisher—Applied Biosystems).

Sequencing.

The sequencing libraries were multiplexed and clustered onto a flowcell. After clustering, the flowcell was loaded on the Illumina HiSeq 4000 or equivalent instrument according to manufacturer's instructions. The samples were sequenced using a 2×150 bp Paired End (PE) configuration. Image analysis and base calling were conducted by the HiSeq Control Software (HCS) on the HiSeq instrument. Raw sequence data (.bcl files) generated from Illumina HiSeq was converted into fastq files and de-multiplexed using the Illumina bcl2fastq v 2.17 program. One mis-match was allowed for index sequence identification.

RNA-Seq Analysis.

After investigating the quality of the raw data, sequence reads were trimmed to remove possible adapter sequences and nucleotides with poor quality using Trimmomatic v.0.36 (Bolger et al., 2014). The trimmed reads were mapped to the Mus musculus reference genome available on ENSEMBL using the STAR aligner v.2.5.2b. The STAR aligner uses a splice aligner that detects splice junctions and incorporates them to help align the entire read sequences. BAM files were generated as a result of this step. Unique gene hit counts were calculated by using feature Counts from the Subread package v.1.5.2. Only unique reads that fell within exon regions were counted. Since a strand-specific library preparation was performed, the reads were strand-specifically counted.

After extraction of gene hit counts, the gene hit counts table was used for downstream differential expression analysis. Using DESeq2, a comparison of gene expression between the groups of samples was performed. The Wald test was used to generate p-values and $Log_2$ fold changes. Genes with adjusted p-values<0.05 and absolute $log_2$ fold changes>1 were called as differentially expressed genes for each comparison. A gene ontology analysis was performed on the statistically significant set of genes by implementing the software GeneSCF. The mgi GO list was used to cluster the set of genes based on their biological process and determine their statistical significance. A PCA analysis was performed using the "plotPCA" function within the DESeq2 R package. The plot shows the samples in a 2D plane spanned by their first two principal components. The top 500 genes, selected by highest row variance, were used to generate the plot. The RNASeq data has been stored at https://figshare.com/s/e6c0df2faacdf1ffb306. It can also be located through DOI; 10.6084/m9.figshare.7910444.

Statistics.

Friedman's test was used for paired data, while the Kruskall Wallis test was used for unpaired group of observations. Post-hoc analysis of differences and comparison of differences between pairs of data was done with the Wilcoxon Rank test and the Mann Whitney U test for paired and unpaired observations respectively. Differences were considered significant at p<0.05. Differences in RNASeq analysis between the test and control groups were further considered significant at an adjusted p-value<0.05. The primary outcome measures are presented in scatter or dot plots. For the scatter plots, the inner dark line represents the mean value while the whiskers above and below the mean represent the standard error of mean. For the box plots, the bottom and top of the boxes represent the lower and upper quartiles respectively, the dark band inside the box represents the median, while the top and bottom whiskers represent the maximum and minimum observed values respectively. Data analysis and preparation of figures was done with GraphPad Prism 7.0b software.

Example 1

E1 Polarized Eosinophils Accumulate in Tolerant a Rejecting Lung Allografts

Figure 8A:
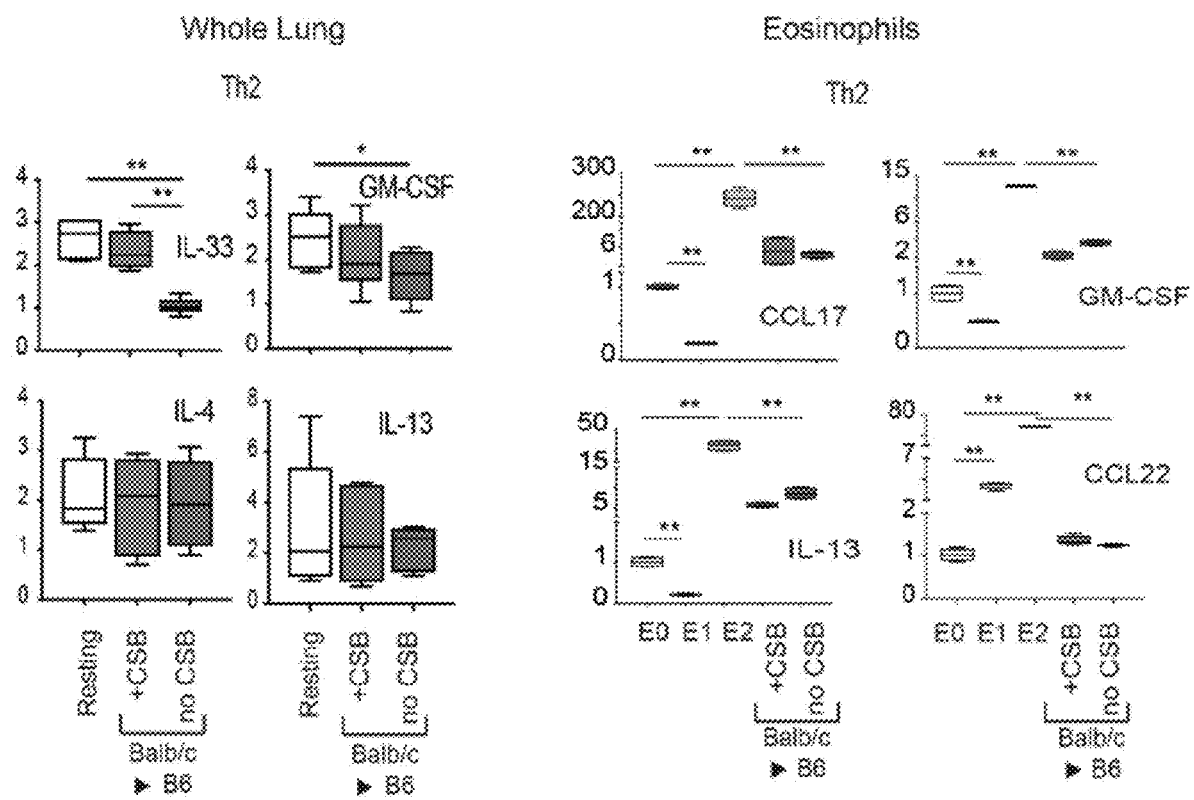
FIGS. 8A-8C.

It has been demonstrated that eosinophils can alter their phenotype and function based on the local environment (Jacobsen et al., 2015; Onyema et al., 2017; Abdala-Valencia et al., 2018). Since co-stimulation plays a critical role in T cell cytokine production and environmental polarization (Kato & Nariuchi, 2000; Sharpe, 2009), the possibility that eosinophils could lose their tolerogenic properties in the absence of co-stimulatory blockade (CSB) immunosuppression was investigated. Cytokine expression was examined in Balb/c ($H2^d$) lung allografts transplanted into fully MHC-mismatched C57BL/6 (B6)($H2^b$) recipient mice. In the absence of immunosuppression, lung allografts had higher levels of Th-1 polarizing cytokines IFN-γ and TNF-αc than CSB-treated accepting lung grafts (FIG. 1A). Limited amounts of Th-2 polarizing cytokines IL-4, IL-13, IL-33 and GM-CSF were evident in lung allografts treated with or without CSB immunosuppression (FIG. 8A).

Figure 1B:
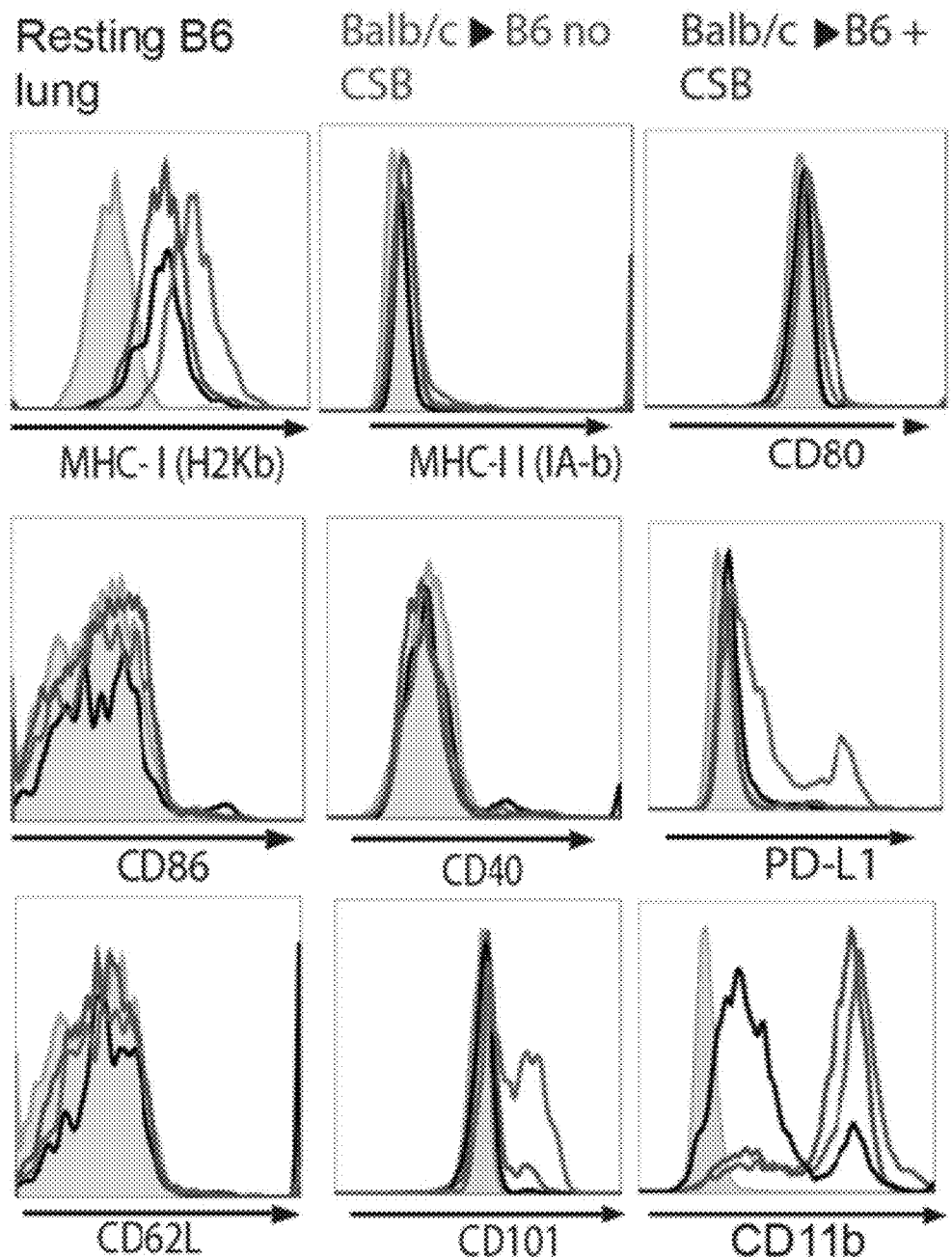
Figure 8B:
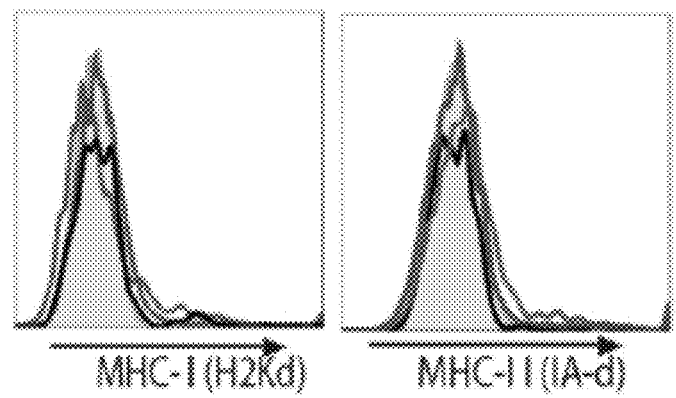

Lung-resident eosinophils from both CSB-treated and non-immunosuppressed grafts were then evaluated. Based on a previously identified eosinophil polarization phenotype (Onyema et al., 2017), higher levels of Th-1 (or E1)-defining features, such as CXCL9, CXCL10, CXCL11 and iNOS in eosinophils isolated from rejecting compared to CSB-treated lung allografts were observed (FIG. 1A). In no group was Th-2 (or E2)-polarization of eosinophils detected (FIG. 8A). Flow cytometric characterization demonstrated an absence of MHC II and costimulatory molecules such as CD80, CD86 and CD40. However, there were high levels of recipient-derived MHC I ($H2K^b$), PD-L1 and CD101 on lung-resident eosinophils in the absence of CSB (FIG. 1B). Of note, Balb/c-derived $H2^d$-MHC were not detected on graft-resident eosinophils indicating a lack of "cross-dressing" or antigen swapping for donor derived-antigens (Markey et al., 2014; FIG. 8B). Thus, while eosinophils from rejecting lungs resembled those from accepting lungs in some aspects, some differences were observed. It is thus possible that in the absence of immunosuppression eosinophils may contribute to graft rejection rather than acceptance, specifically since CD101 expression has been previously associated with an inflammatory eosinophil subtype (Mesnil et al., 2016).

Figure 1C:
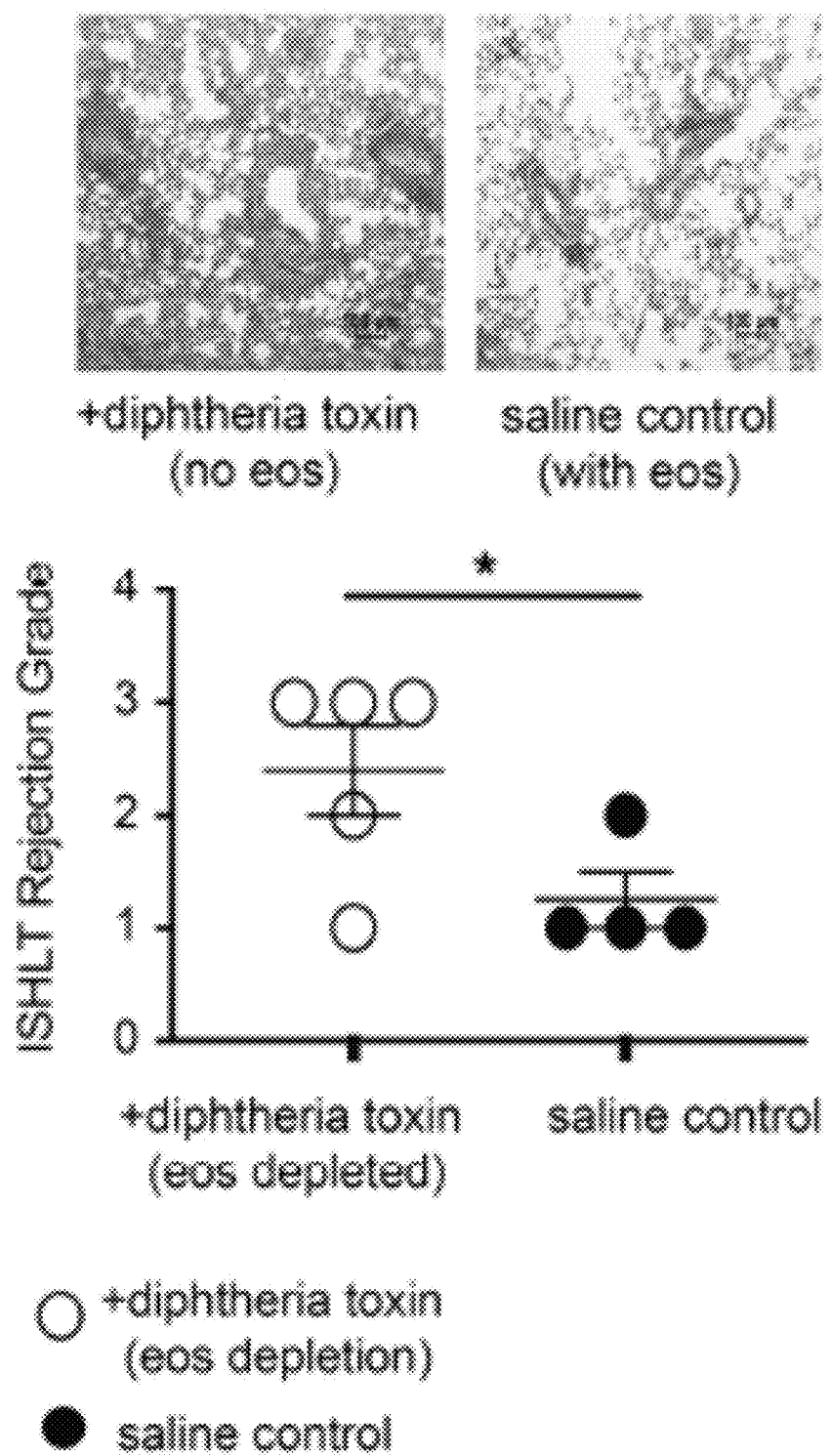
Figure 1D:
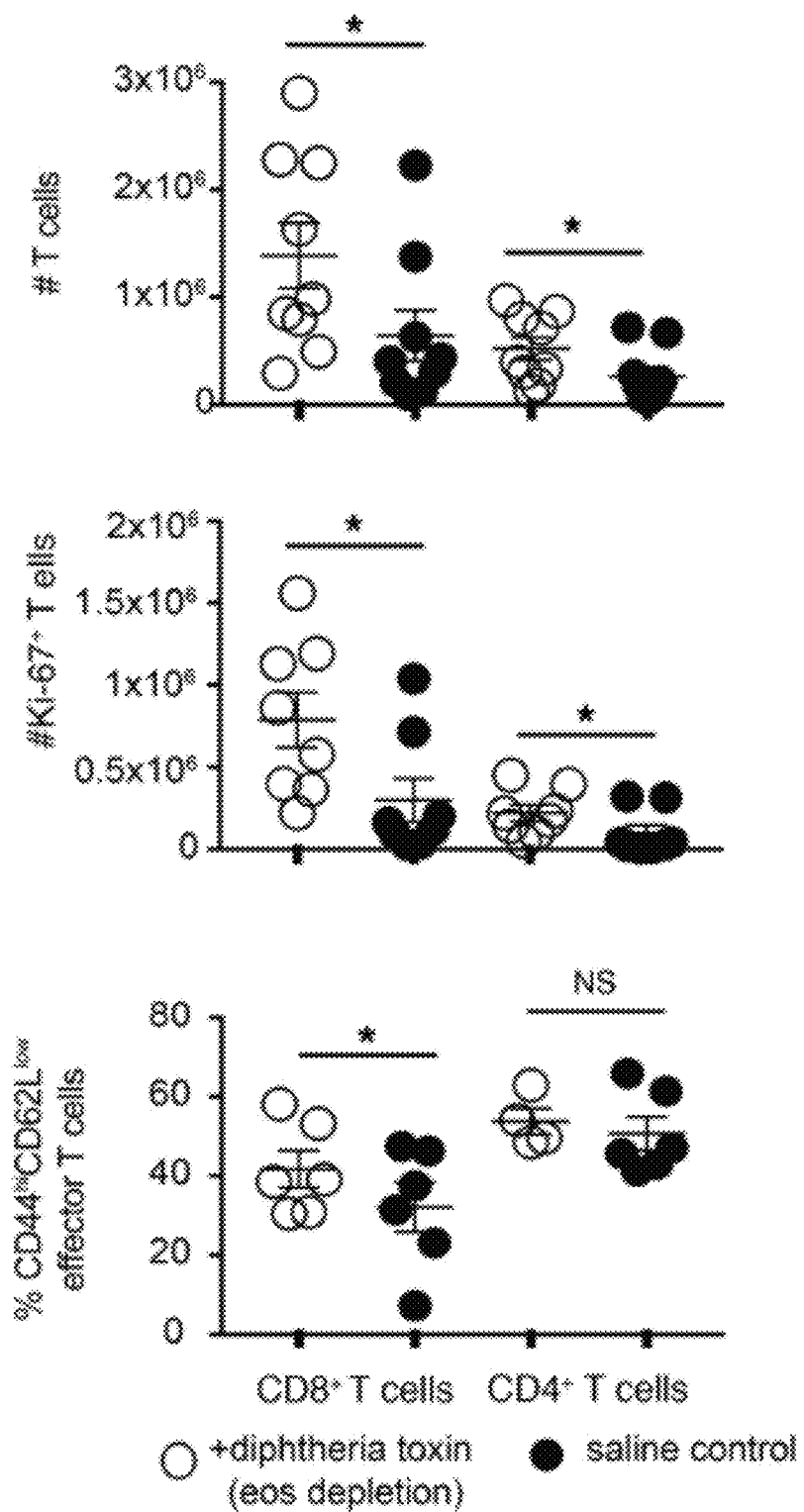
Figure 1E:
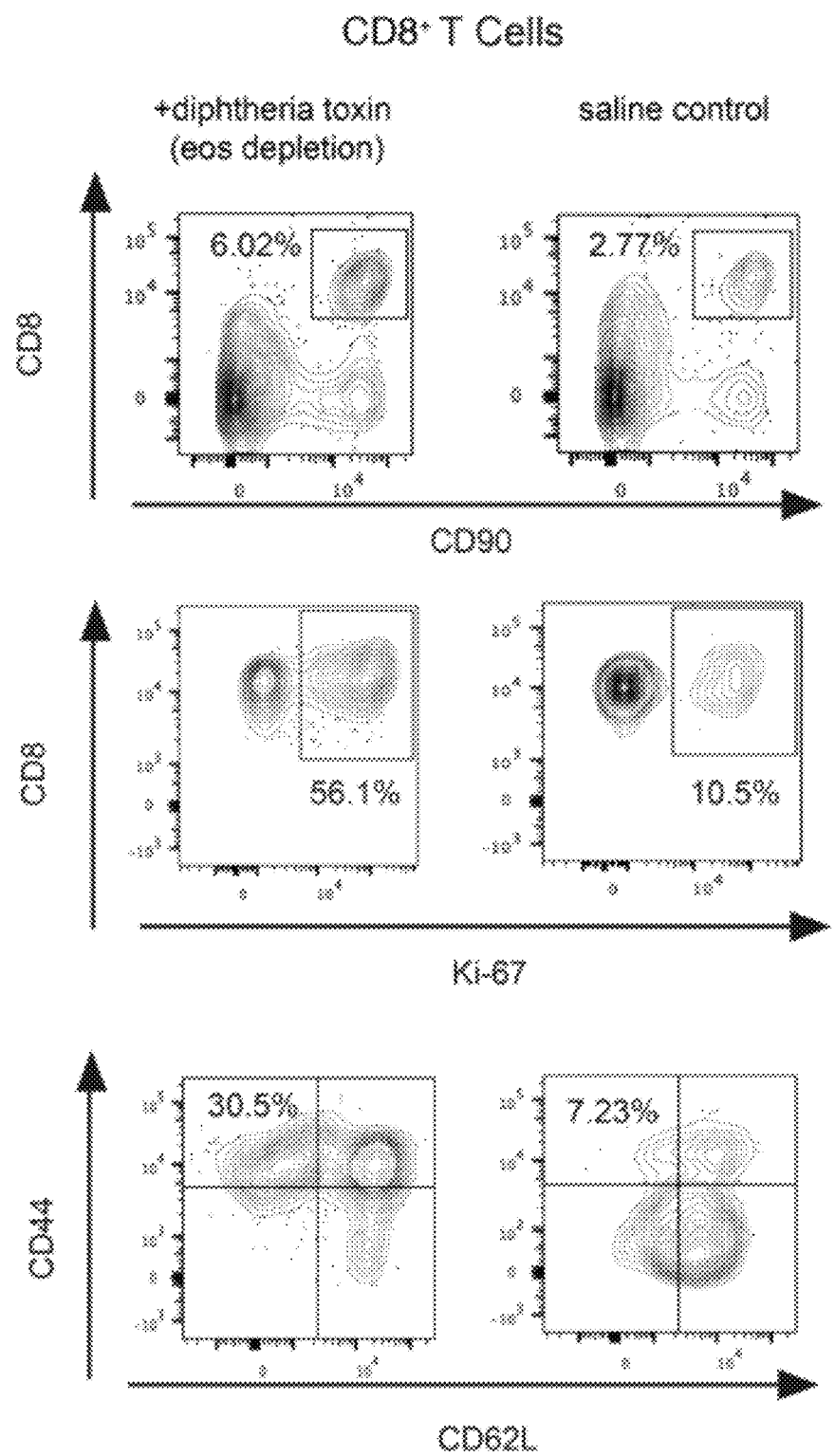
Figure 8C:
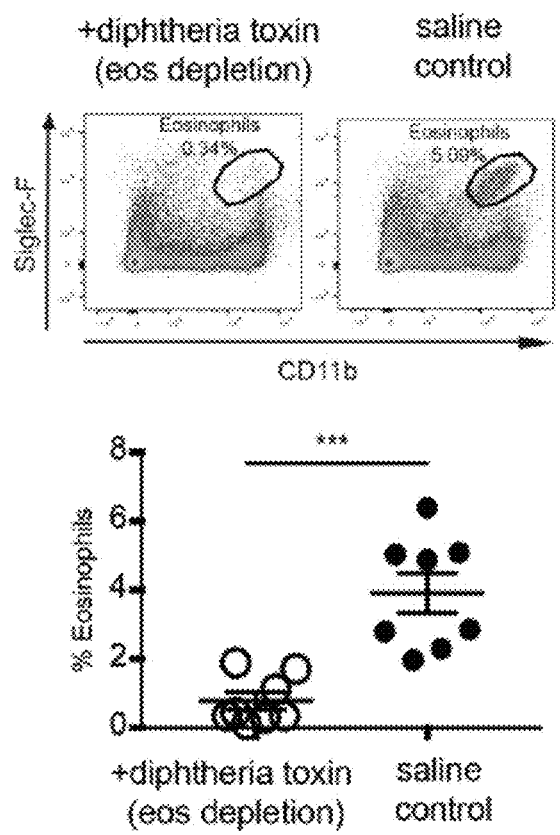

In order to evaluate this directly, eosinophils were conditionally depleted from B6 iPHIL mice, where the diphtheria toxin (DT) receptor is expressed under the control of the eosinophil peroxidase promoter (FIG. 8C; Jacobsen et al., 2014a). DT treated mice or saline injected controls were challenged with a Balb/c lung allograft in the absence of immunosuppression. Surprisingly, mice depleted of eosinophils had higher grades of rejection (FIG. 1C), increased numbers of lung-resident T lymphocytes, increased rates of T cell proliferation, and increased effector cell differentiation by day 4 post-engraftment (FIGS. 1D and 1E). These patterns of T lymphocytes activation and infiltration were especially prominent for CD8+ T cells. CD4+ T cell proliferation did increase slightly in the absence of eosinophils, but the relative proportion of $CD44^{hi}CD62L^{low}$ effector cells did not change (FIGS. 1D and 1E).

Figure 2A:
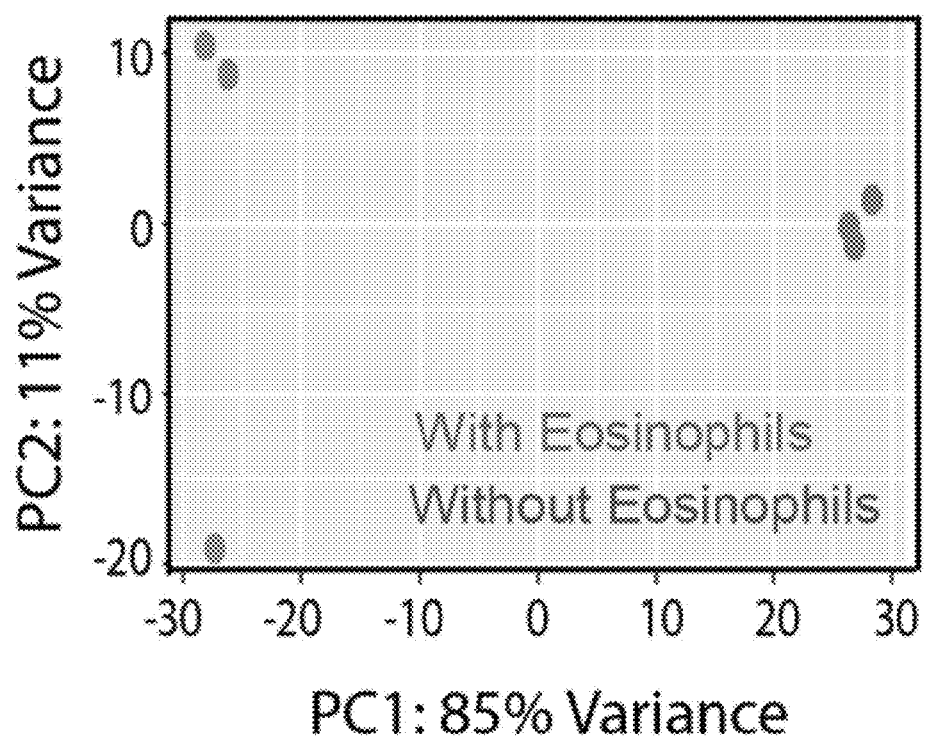
FIGS. 2A-2C: Gene expression analysis of lung allograft-resident CD8$^+$ T cells in the presence or absence of eosinophils.
Figure 2B:
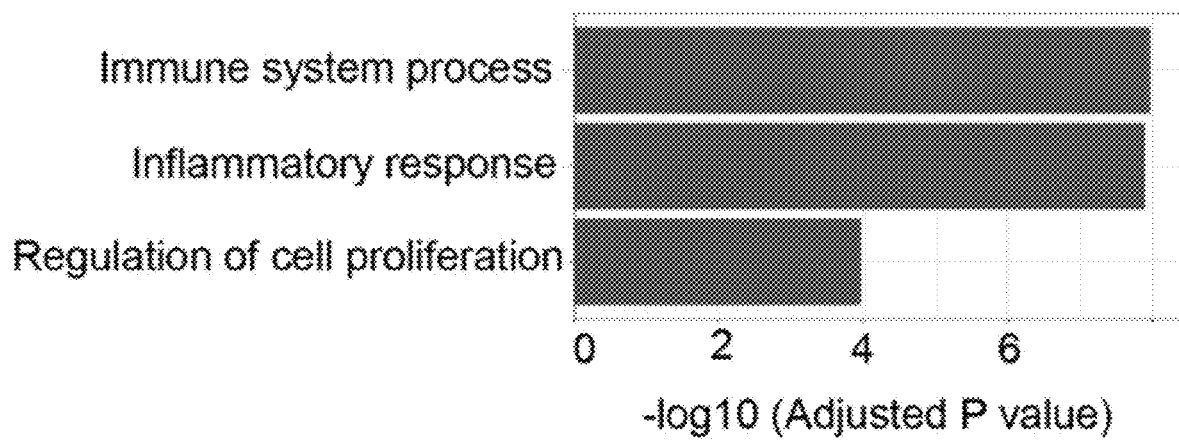
Figure 2C:
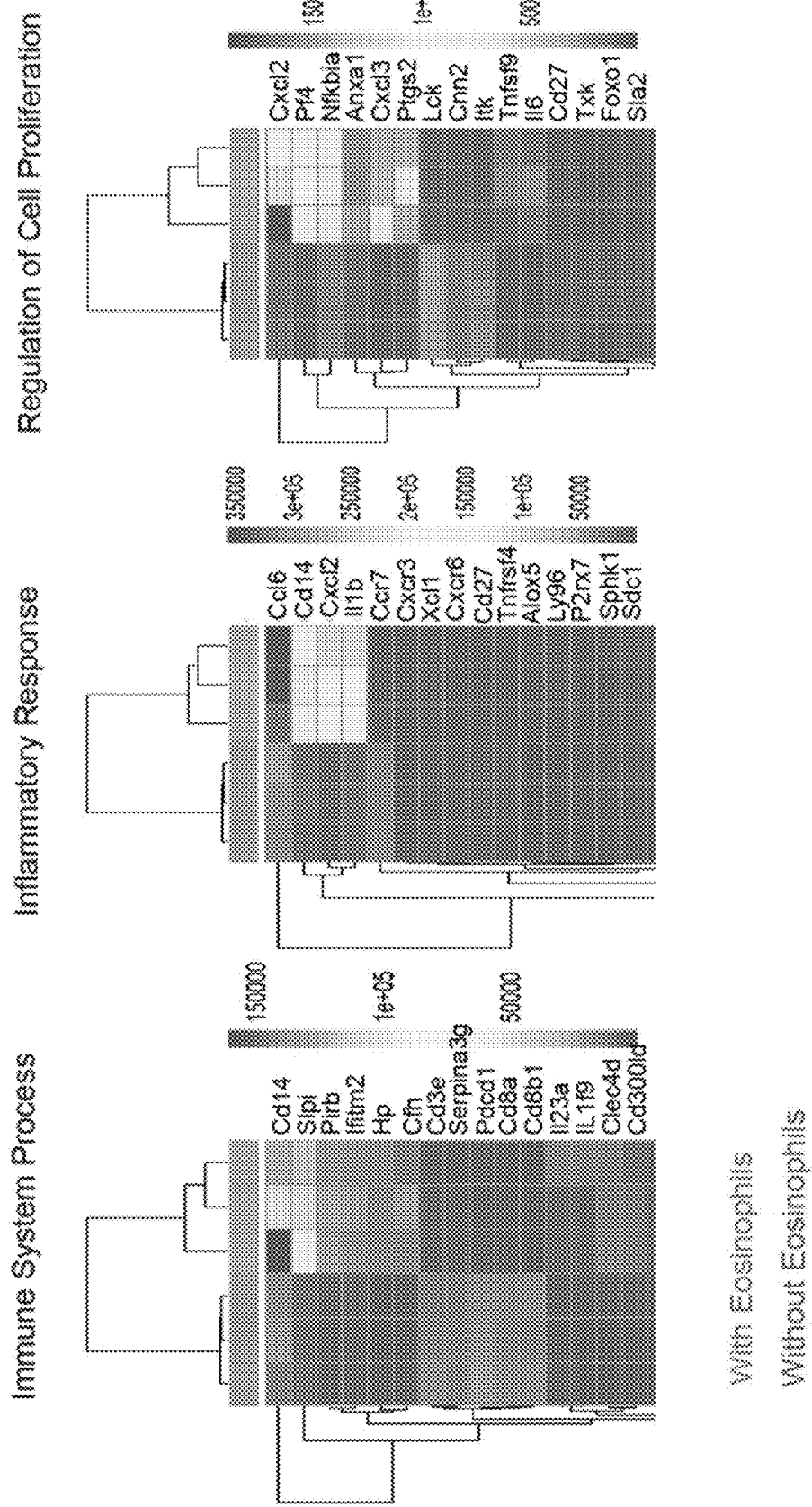
Figure 9A:
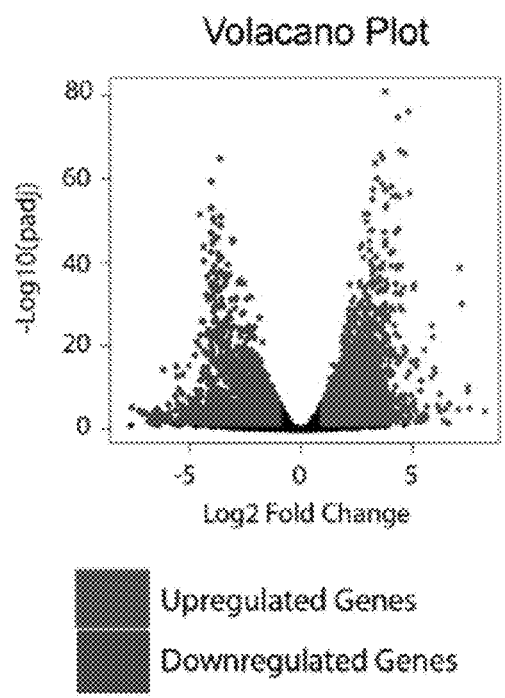
FIGS. 9A and 9B.
Figure 9B:
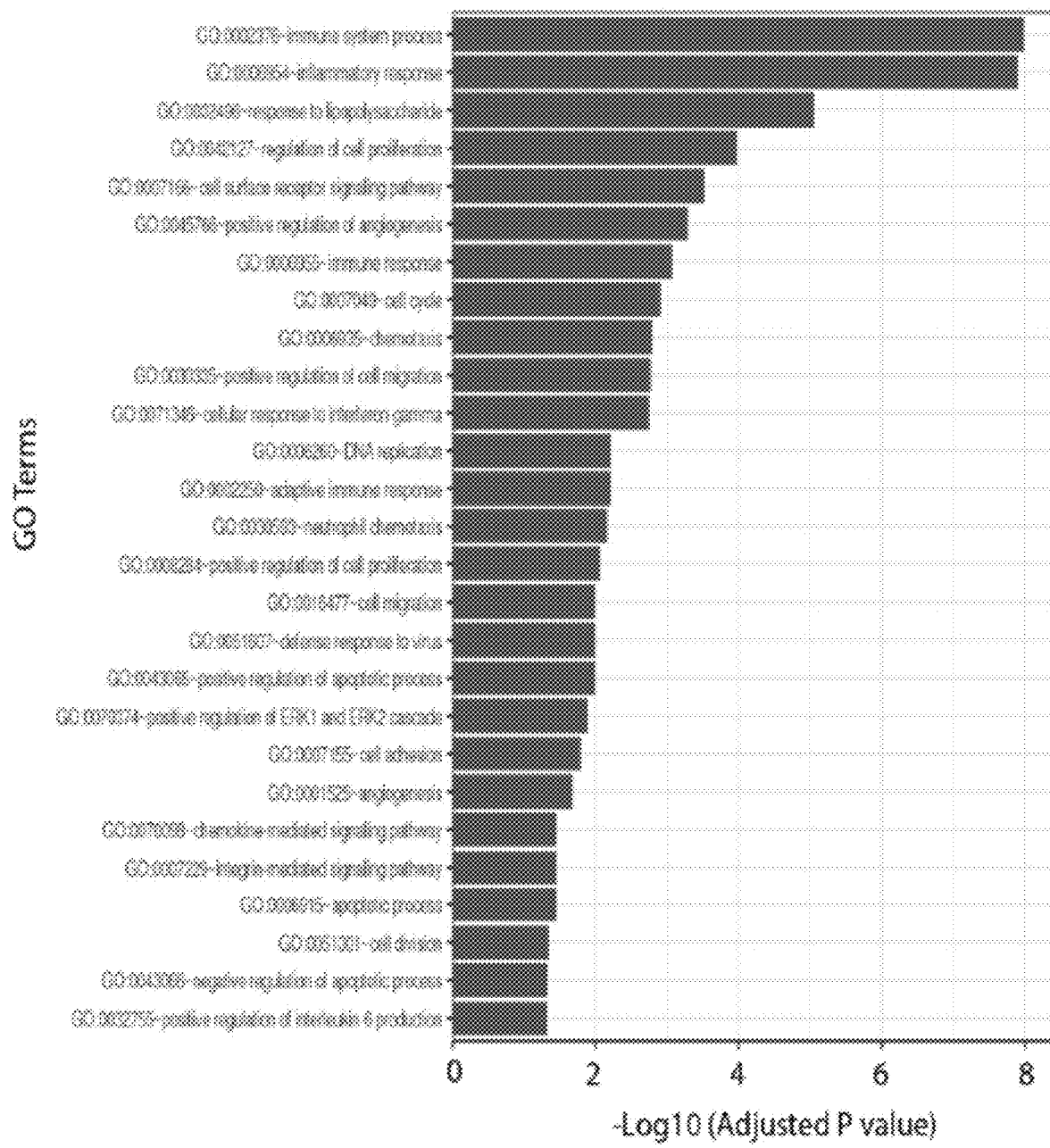

To further characterize eosinophil-mediated effects on CD8+ T cells, lung allograft resident CD8+ T cells were transcript profiled in eosinophil-sufficient or eosinophil-depleted mice. Principal component analysis (PCA) demonstrated that CD8+ T cells from eosinophil sufficient or deficient mice differed substantially (FIG. 2A). Gene expression analysis demonstrated an upregulation of 2956 and downregulation of 2360 genes in the absence of eosinophils (FIG. 9A). Using unbiased hierarchical gene ontology analysis to cluster the 5316 differentially expressed genes, significant upregulation of the inflammatory response, immune system processing, and cell proliferation clusters were noted as three of the top four clusters among the 27 gene ontology groups that differ substantially between lung-resident CD8+ T cells in eosinophil-depleted and eosinophil-sufficient mice (FIGS. 2B and 2C; FIG. 9B). Taken together, it can be concluded that eosinophils played a unique and unequivocal role in the downregulation of CD8+ T cell-mediated alloimmune responses in the lung allograft. However, mechanistic aspects of CD8+ T cell suppression remained unclear.

Example 2

Figure 3A:
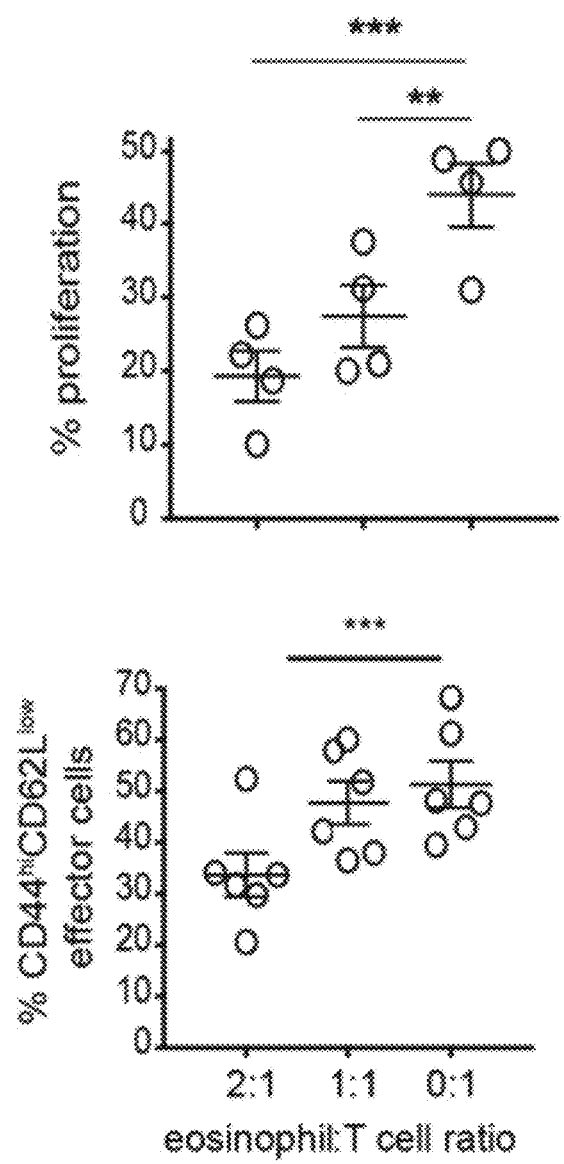
FIGS. 3A-3C: In vitro inhibition of T cells by E1 polarized eosinophils.
Figure 10A:
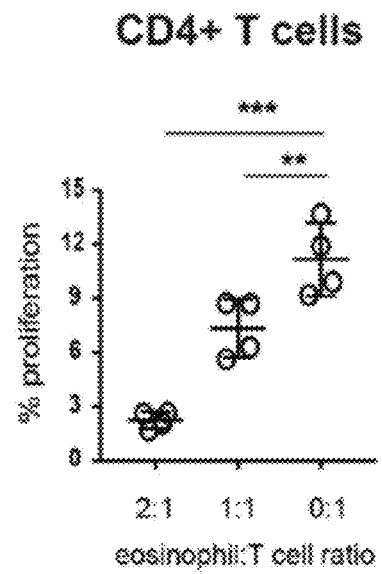
FIGS. 10A and 10B.

Eosinophils Suppress T Cell Responses in a Dose-, Contact-, and iNOS– Dependent-Manner In order to further define the mechanism of eosinophil-mediated immunosuppression, a reductionist approach was taken and increasing ratios of E1 polarized eosinophils were co-cultured with B6 T cells in the presence of anti-CD3/CD28 polyclonal stimulation for a total of five days in vitro. Consistent with in vivo observations, eosinophils inhibited both proliferation as well as effector differentiation of CD8+ T cells in a dose dependent manner, even in the absence of professional antigen presenting cells (FIG. 3A). A similar, but less pronounced, degree of inhibition was observed for CD4+ T cells (FIG. 10A).

Figure 10B:
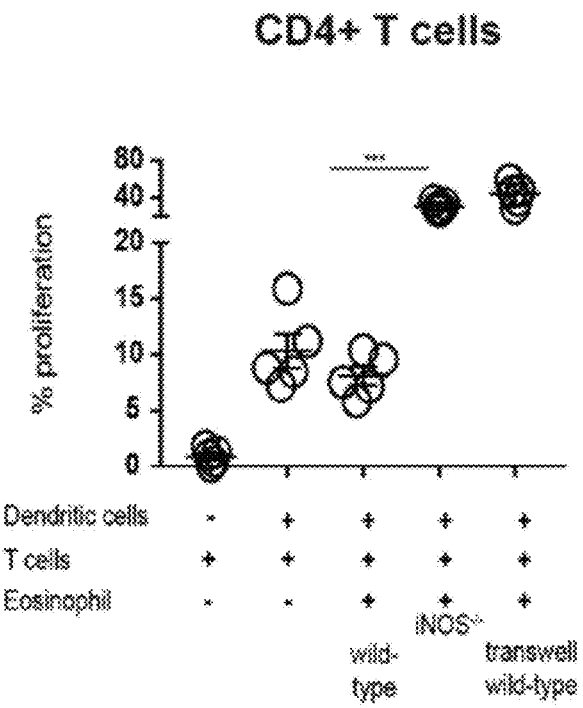

To define in more detail those factors that controlled eosinophil-mediated T cell regulation, iNOS was initially focused on based on its upregulation in the lung graft (FIG. 1A; Onyema et al., 2017), as well as physical contact of eosinophils with T lymphocytes. Thus, B6 T cells were cultured with Balb/c dendritic cells in the presence of wild-type eosinophils, $iNOS^{-/-}$ eosinophils or wild-type eosinophils separated from T cells by a semi-permeable transwell, preventing direct T cell-eosinophil contact. Elimination of either eosinophil iNOS expression or eosinophil-T cell interaction ameliorated suppression of T cell responses (FIG. 3B; Supplemental FIG. 10B).

Figure 3B:
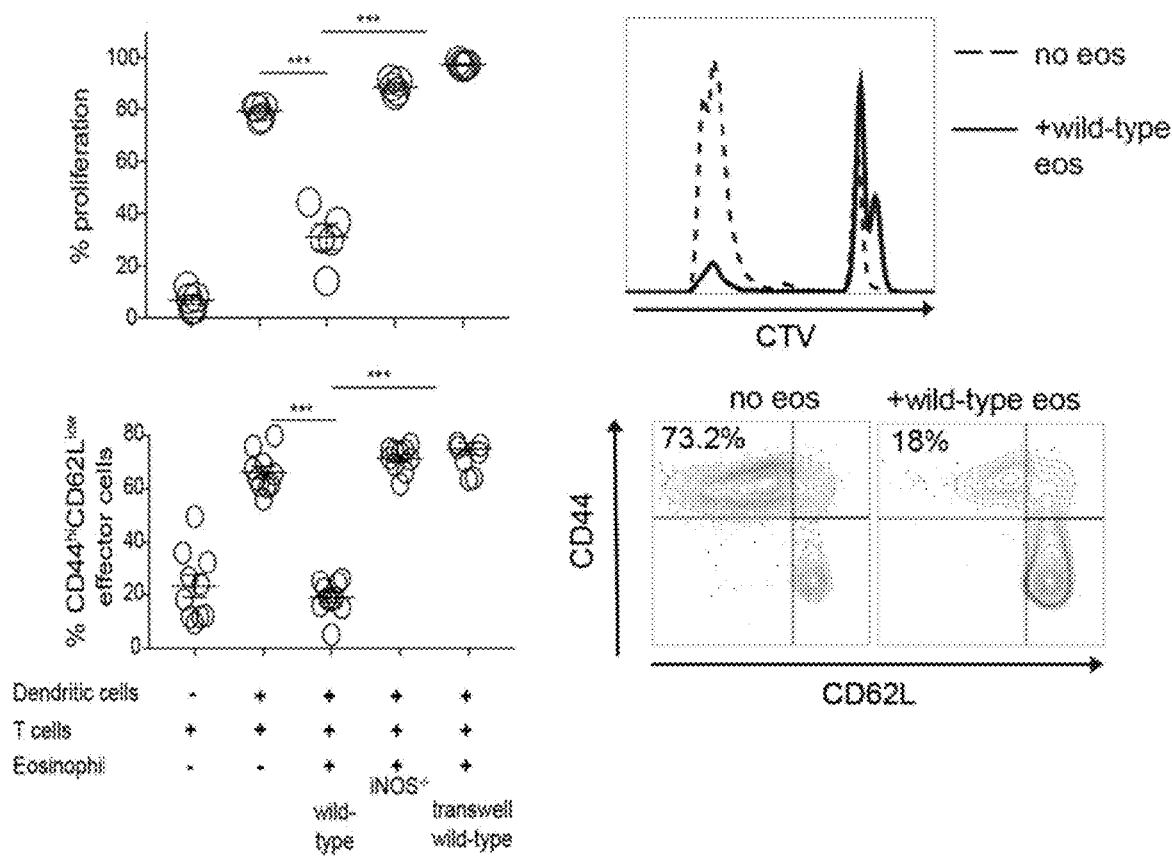
Figure 3C:
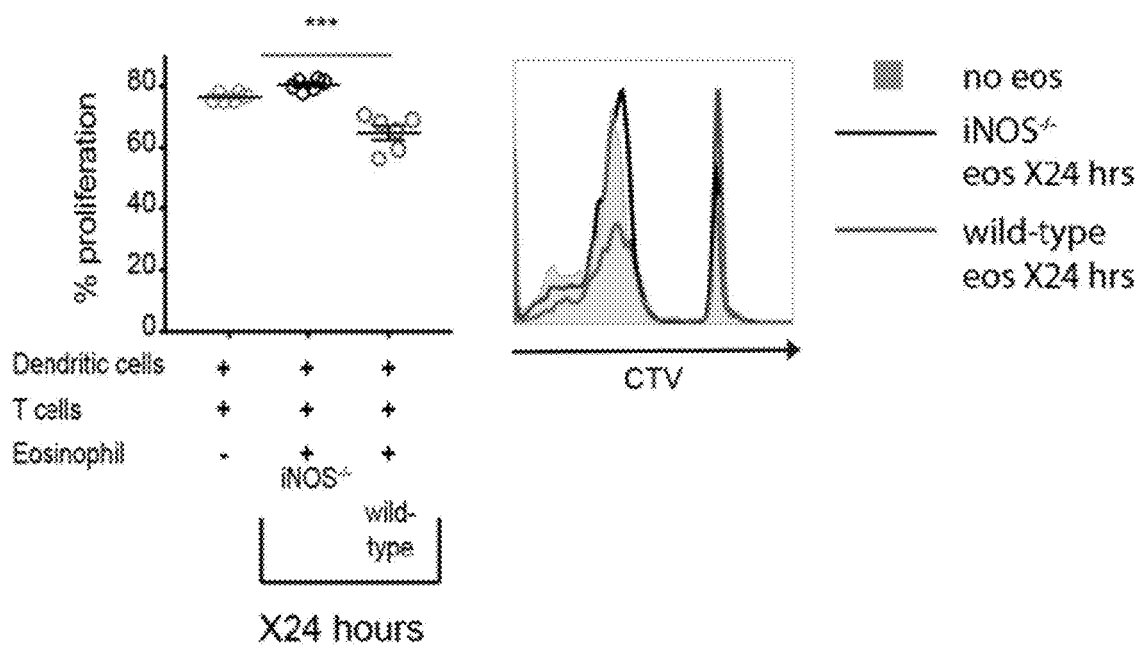

These experiments were extended by co-culturing wild-type or iNOS$^{-/-}$ eosinophils with B6 T cells and Balb/c dendritic cells but removed eosinophils after 24 hours of culture. Even after this brief period of interaction eosinophils still suppressed T cell proliferation (FIG. 3C). Taken together, these data suggested that eosinophils suppressed T cell responses through a contact and iNOS-dependent mechanism early during the course of the immune response.

Example 3

Figure 4A:
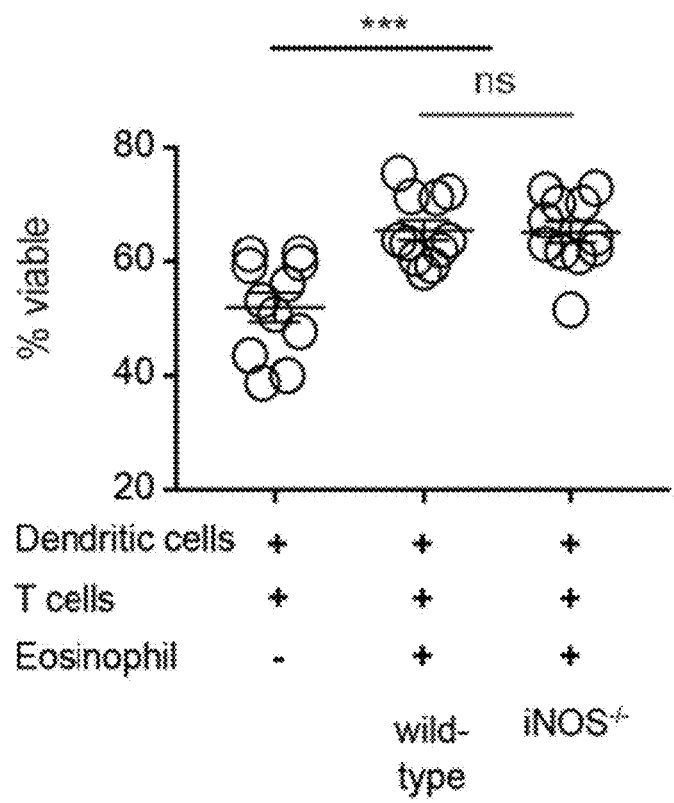
FIGS. 4A-4C: Eosinophils alter TCR signal transduction.
Figure 11A:
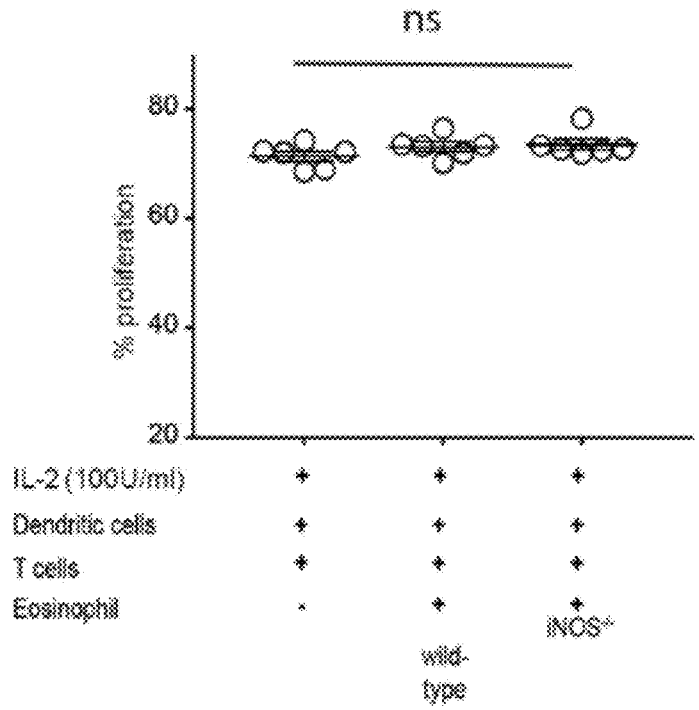
FIGS. 11A-11C.

Eosinophils Suppress T Cell Responses by Altering the Integrity of the TCR/CD3 Complex How eosinophil-derived iNOS inhibits T cell activation was investigated. Previous work had described that iNOS elaborated mediators such as nitric oxide (NO) and reactive oxygen species (ROS) can initiate T cell death (Murphy, 1999), raising the possibility that eosinophils might control alloreactivity by altering T cell viability. However, the presence of eosinophils in in vitro MLRs did not decrease T cell viability and, surprisingly, even enhanced survival (FIG. 4A). It has been described that iNOS-expressing myeloid-derived suppressor cells may modify T cell reactivity in a contact-dependent fashion through post-translational modification of key signaling intermediates within the IL-2 signaling pathway (Schouppe et al., 2013). IL-2-mediated T cell proliferation, however, was not affected upon culture with wild type eosinophils (FIG. 11A).

Figure 4B:
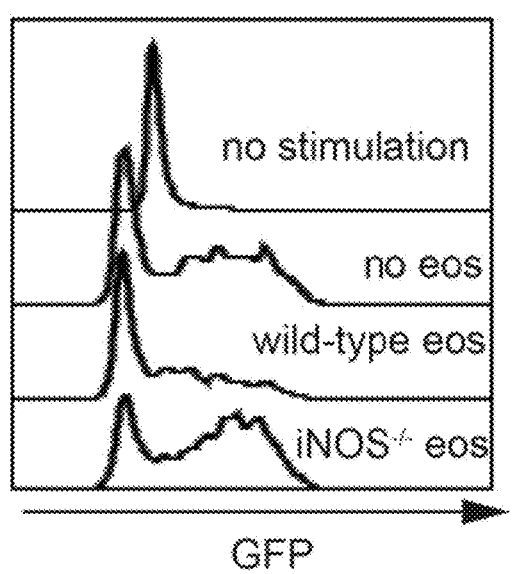
Figure 4B:
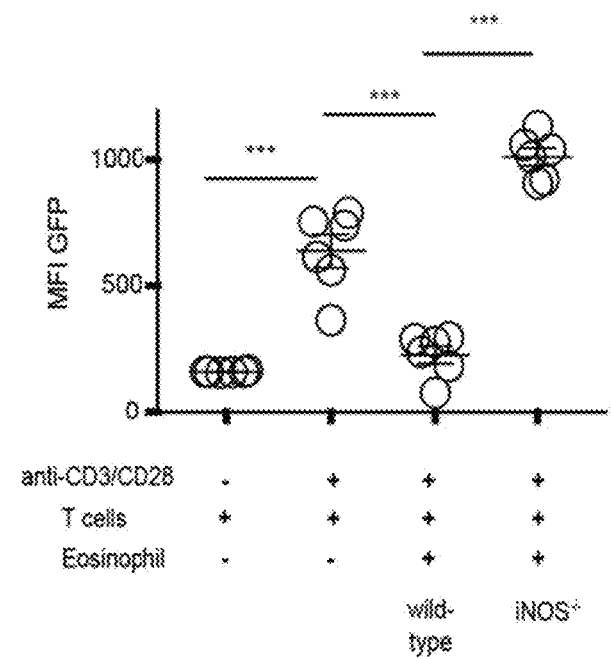
Figure 11B:
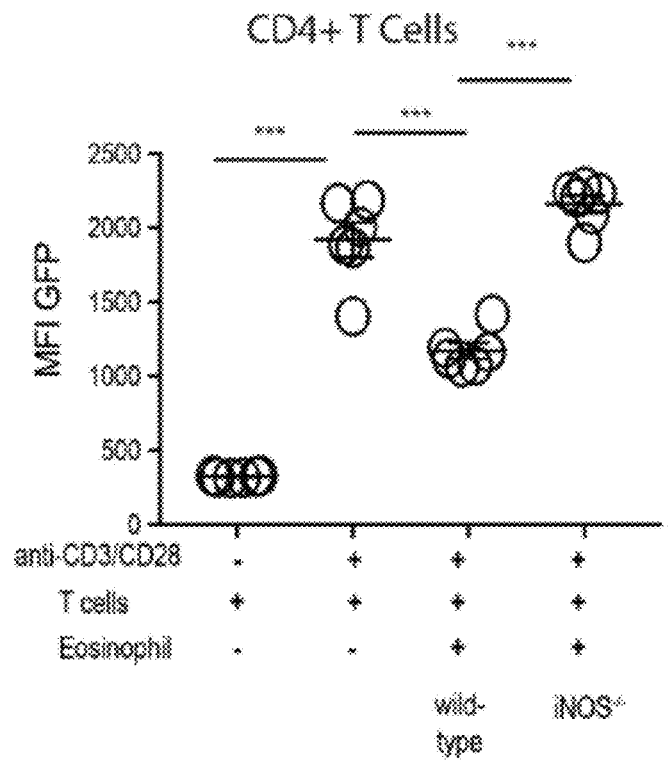
Figure 11C:
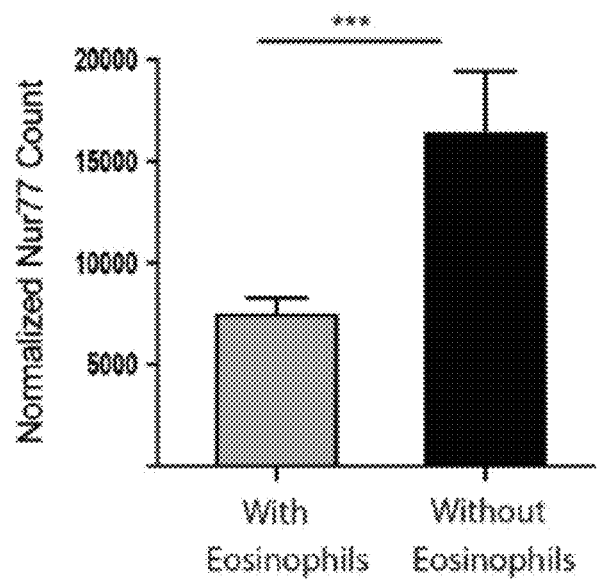

Alternatively, modulation of T cell receptor (TCR) signaling has been described as another mechanism of iNOS-mediated immunoregulation. Particularly, it has been demonstrated that myeloid derived suppressor cells can induce tumor-specific T cell tolerance by interfering with TCR signal transduction and altering the integrity of the TCR in a contact dependent fashion (Nagaraj et al., 2007; Nagaraj et al., 2010). Signal transduction in CD8$^+$ T cells was thus evaluated using a system of green fluorescent protein (GFP) driven by Nr4a1 (Nur77), an early TCR-responsive gene the expression of which directly correlates with the strength of the TCR signal (Moran et al., 2011; Ashouri & Weiss, 2017). Indeed, a near complete ablation of TCR signal transduction was noted in T cells cultured with wild-type, but not iNOS$^{-/-}$ eosinophils (FIG. 4B; FIG. 11B). Further validation through transcriptome analysis of CD8$^+$ T cells from lung allografts depleted of eosinophils demonstrated a similar upregulation of Nr4a1 compared with CD8$^+$ T cells from eosinophil sufficient allografts (FIG. 11C).

Figure 4C:
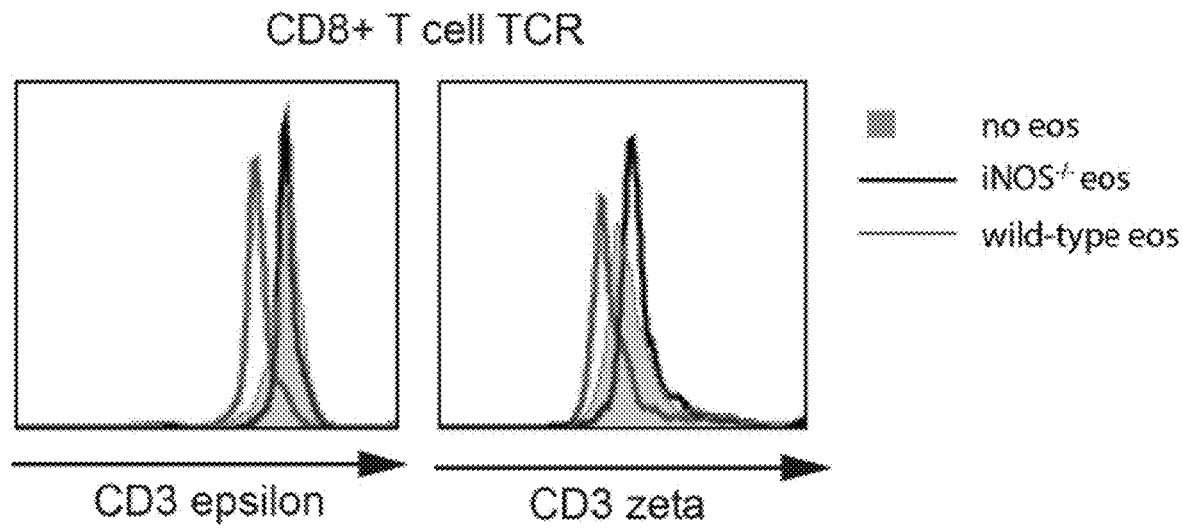

To further explore this, the structural integrity of the TCR from CD8$^+$ T cells cultured in the presence of wild-type or iNOS$^{-/-}$ eosinophils was evaluated utilizing a technique of immunoprecipitation flow cytometry recently described by our group (Schrum et al., 2007; Nagaraj et al., 2010). It was observed that in the presence of wild-type but not iNOS$^{-/-}$ eosinophils the TCRβ subunit showed decreased association with both CD3ε and CD3ζ (FIG. 4C), suggesting dissociation of the TCR/CD3 complex. Taken together, these data suggested that eosinophils controlled T cell responses through contact and iNOS-dependent inhibition of TCR stability and signal transduction.

Example 4

Figure 5A:
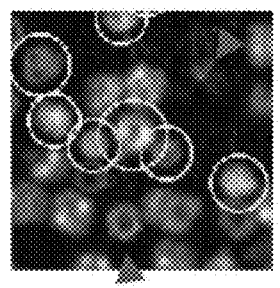
FIGS. 5A-5G: PD-L1 mediated T cell-eosinophil interaction.
Figure 5A:
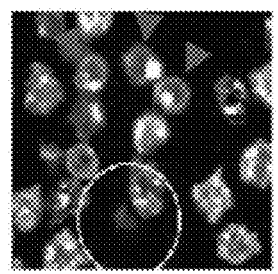
Figure 5A:
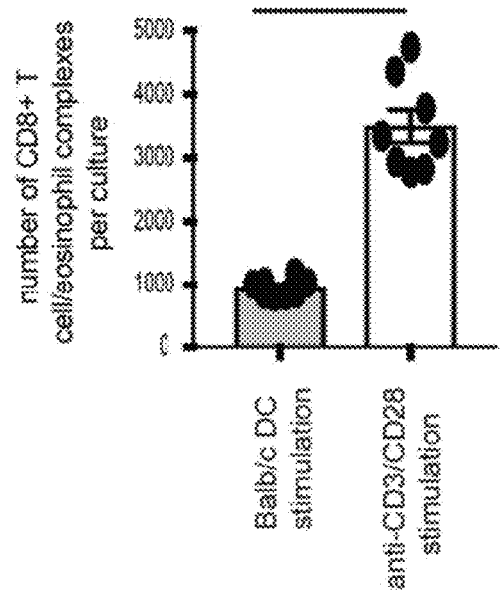
Figure 5A:
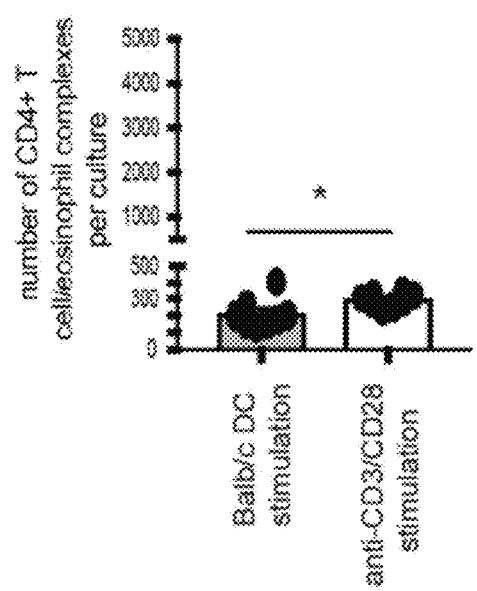
Figure 5B:
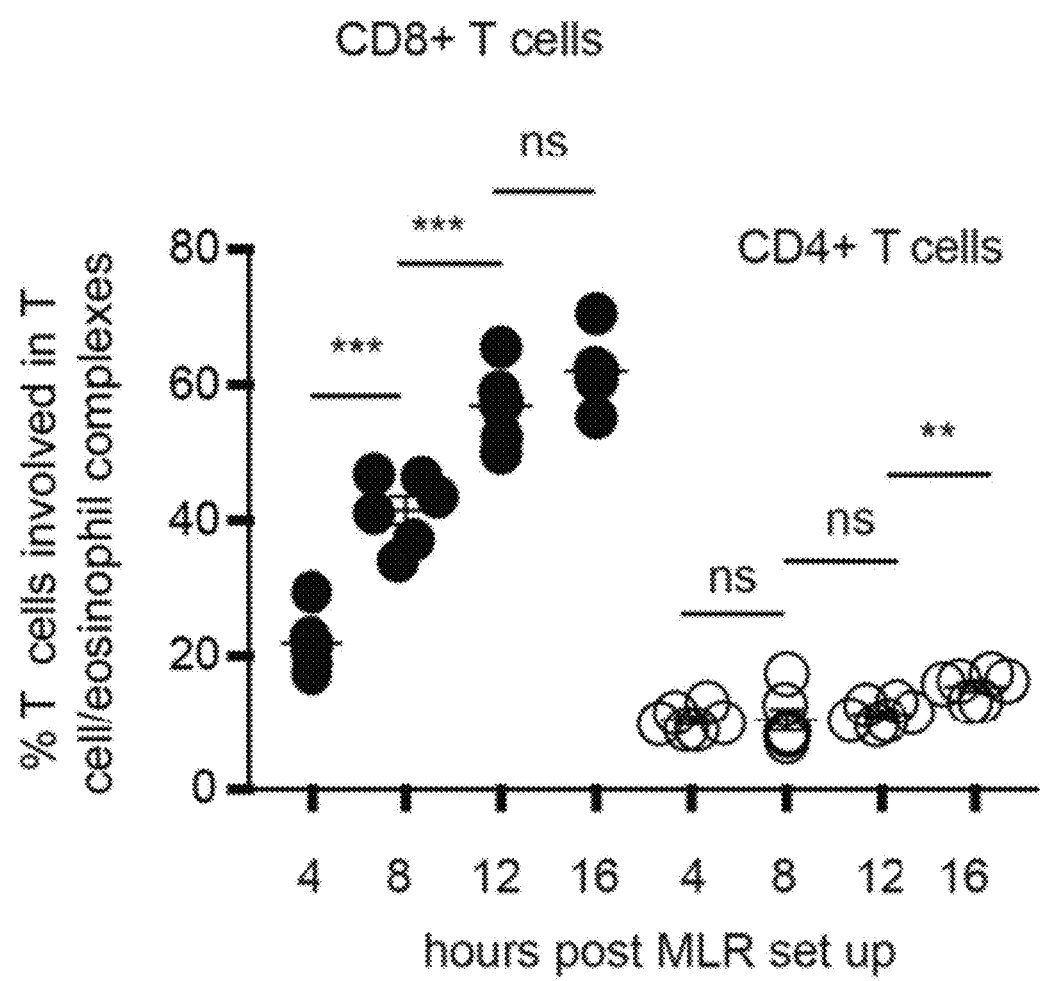

Eosinophils Mediate T Cell Suppression Through PD-L1 Mediated Immunological Synapse Independent of Professional Antigen Presenting Cells Based on the finding that the suppressive capacity of eosinophils depends on their contact with T cells (FIG. 3B), the possibility that professional antigen presenting cells might act as a scaffolding to facilitate eosinophil-T cell contact was tested. This assumption was based in part on previous demonstrations that T cells make stable and durable contact with lung-resident dendritic cells (Gelman et al., 2009) and the fact that eosinophils can mediate the recruitment and accumulation of dendritic cells in asthma models (Jacobsen et al., 2011; Veres et al., 2017). To this end, formation of eosinophil-T cell complexes in co-cultures of B6 T cells stimulated with bone marrow-derived Balb/c dendritic cells or CD3/CD28 agonistic antibodies was compared in a pairwise-fashion. Unexpectedly, no increase in T cell-eosinophil interaction was evident in the presence of dendritic cells. In fact, higher numbers of eosinophil-CD8$^+$ T cell complexes formed with CD3/CD28 stimulation (FIG. 5A). A similar trend was evident for CD4$^+$ T cells, albeit at much lower levels of cell to cell contact (FIG. 5A). In addition, the frequency of T cell-eosinophil interactions increased with the duration of co-cultures for both CD8$^+$ and CD4$^+$ T cells (FIG. 5B), suggesting that other factors, such as degree of T cell activation, might be responsible for contact formation.

Figure 12A:
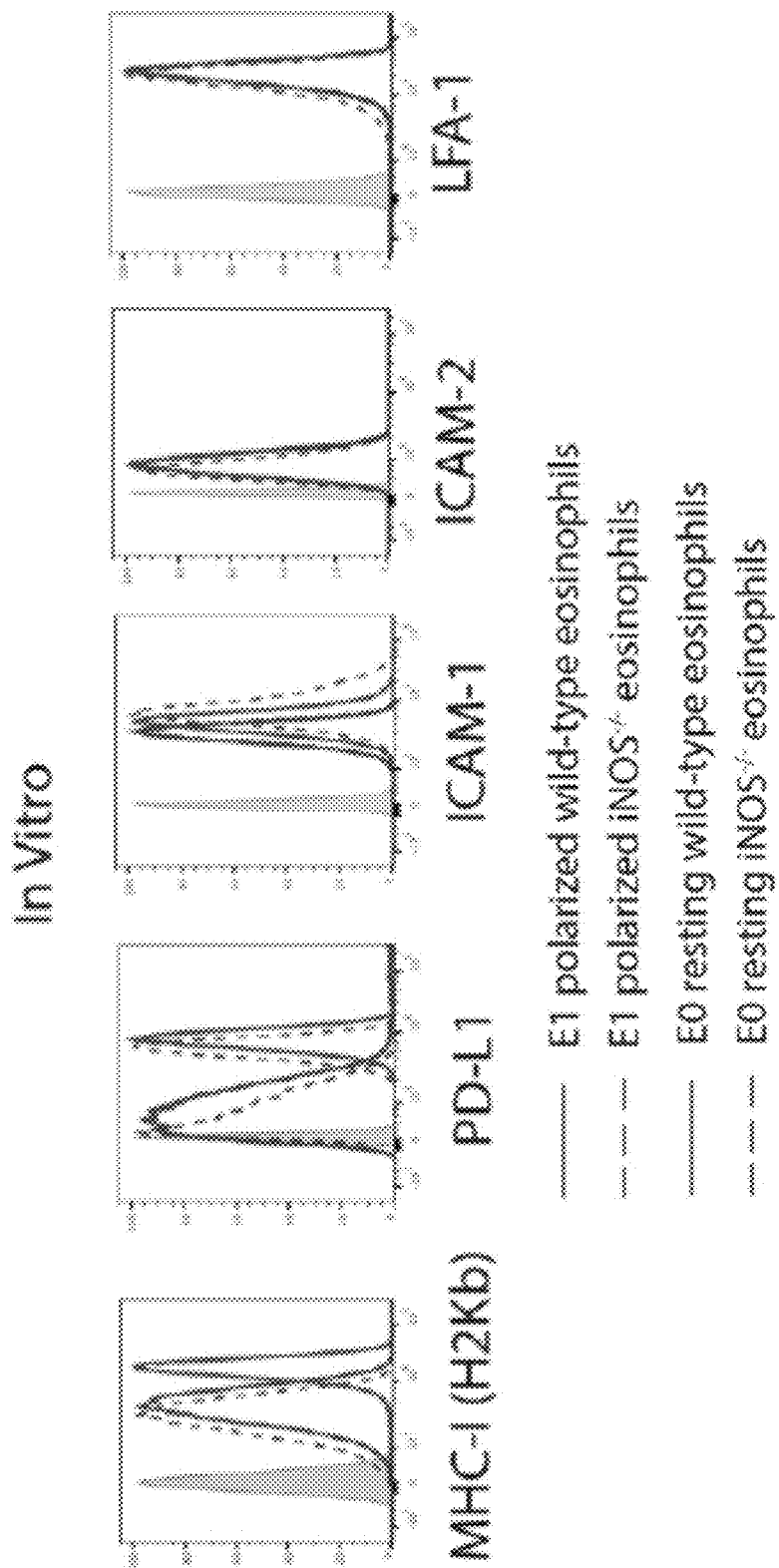
FIGS. 12A-12C.
Figure 12B:
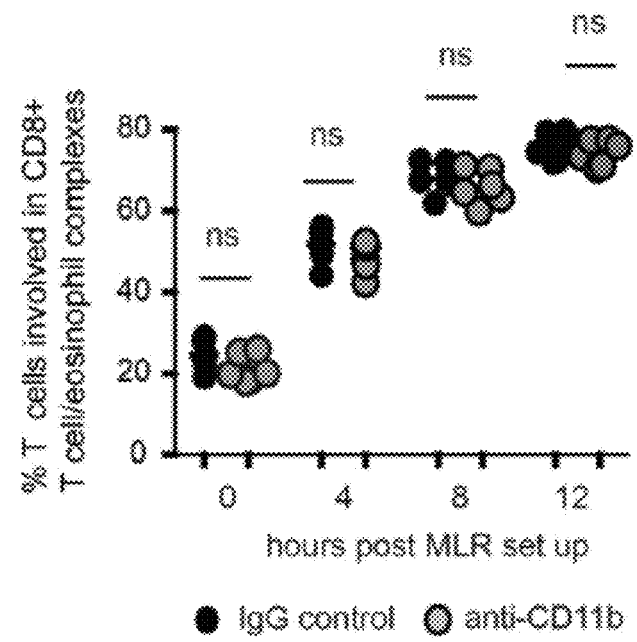

Based on these data, the role of surface junctional proteins in controlling T cell responses was evaluated. E1 polarization of eosinophils specifically upregulated the expression of CD11b and PD-L1 (FIG. 1B; FIG. 12A) but did not affect ICAM-1, 2 or LFA-1 levels (FIG. 12A). As a result, CD11b was initially focused on based on previous data implicating this integrin in mediating human granulocyte-T cell interactions (Pillay et al., 2012). CD11b blockade however did not alter eosinophil/T cell contact (FIG. 12B).

Figure 5C:
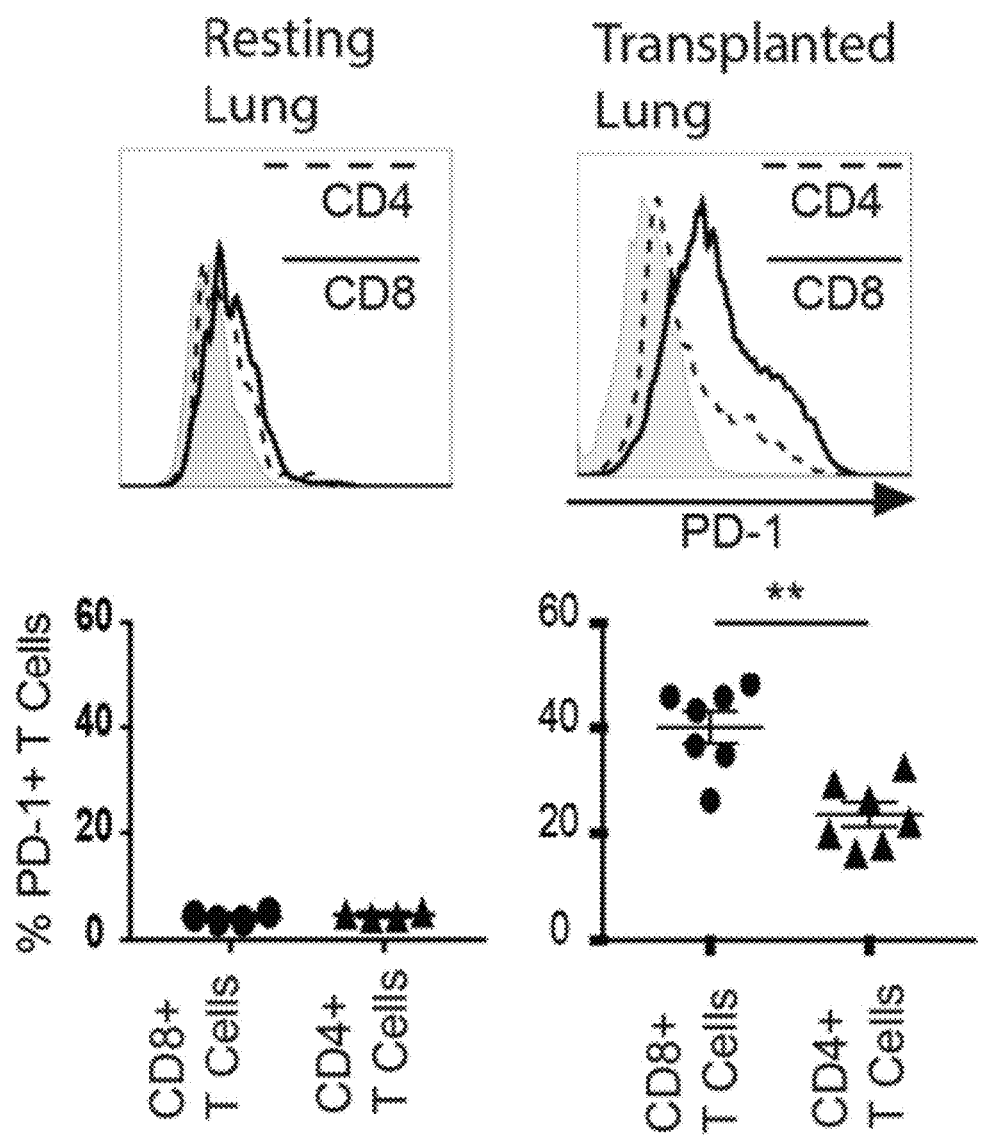
Figure 5D:
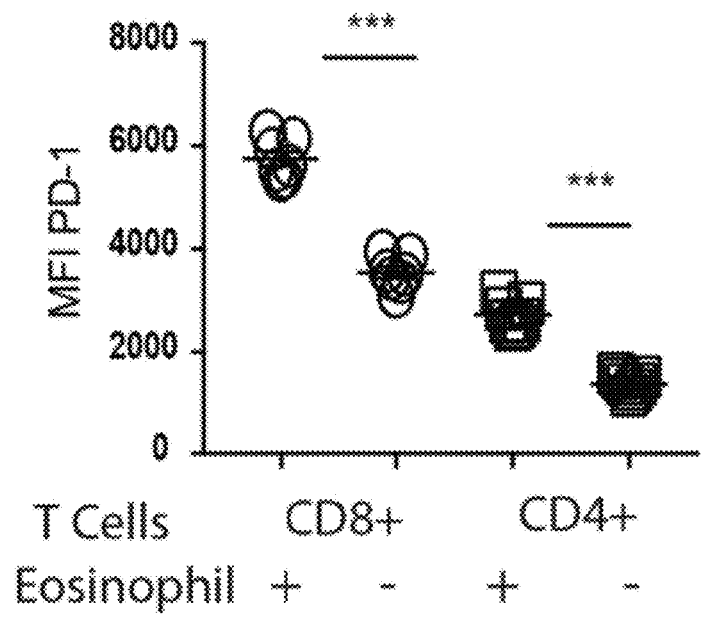
Figure 5E:
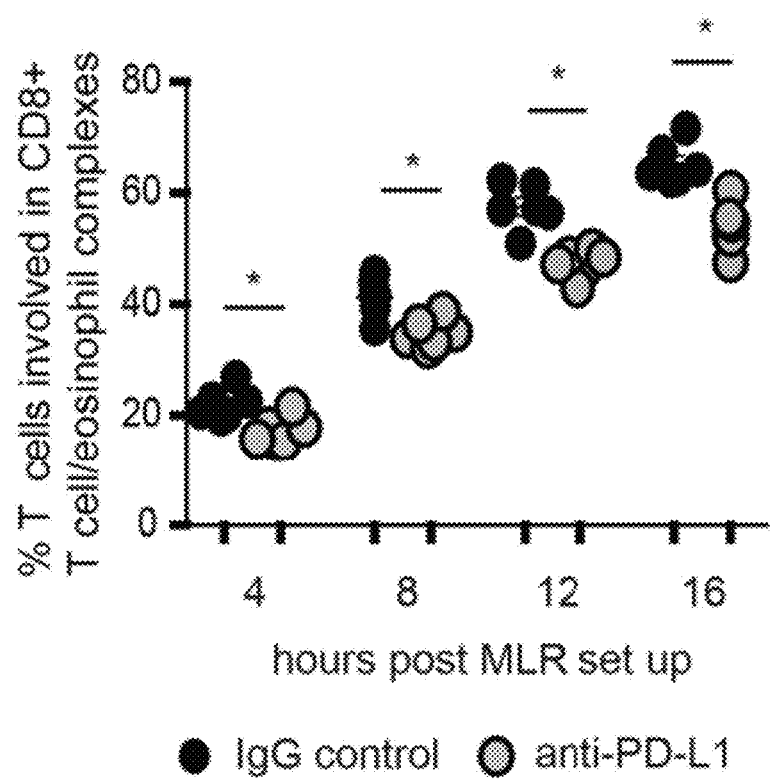
Figure 5F:
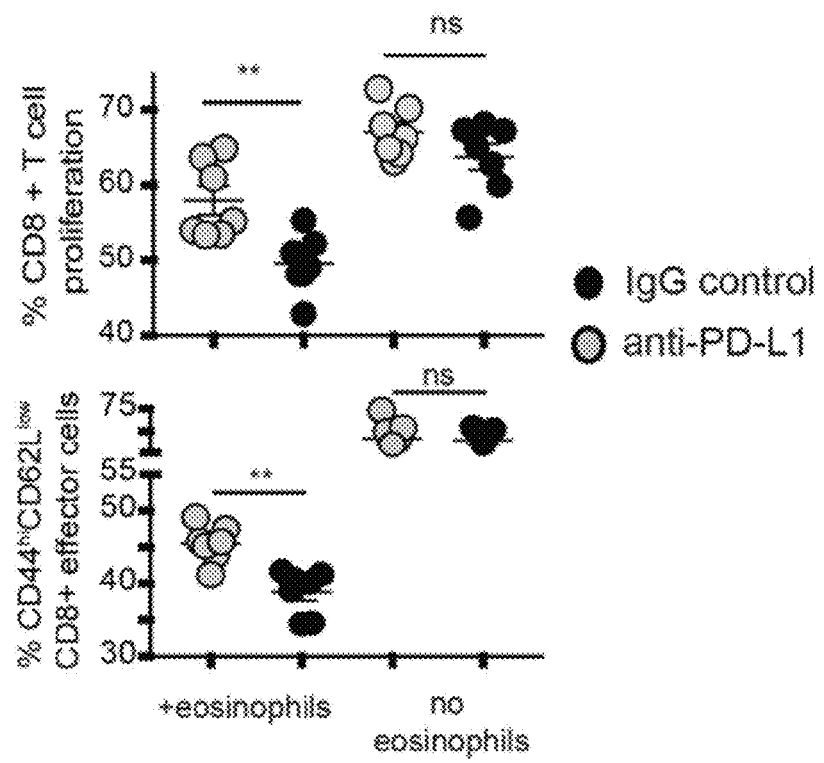
Figure 5G:
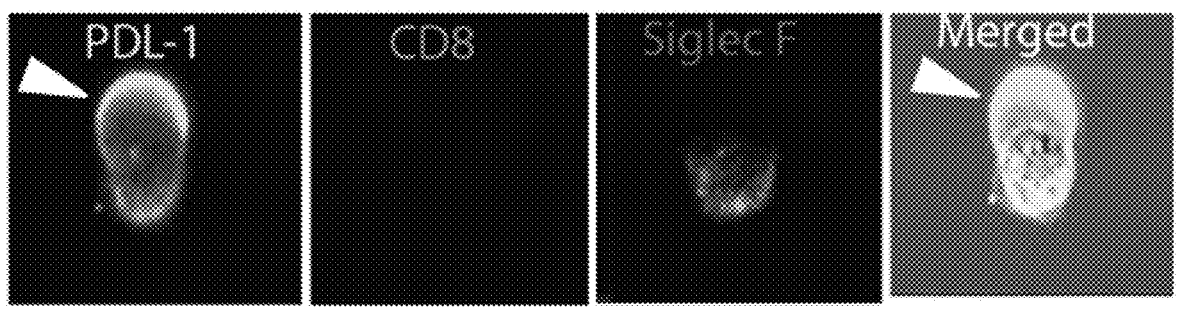
Figure 5G:
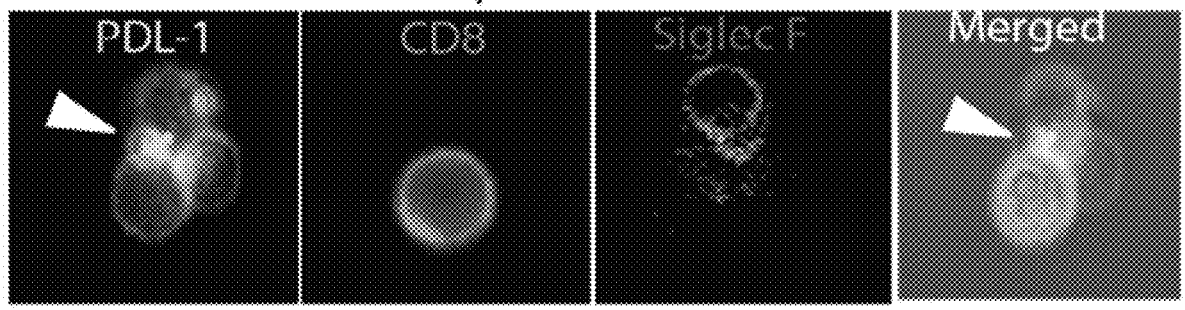
Figure 12C:
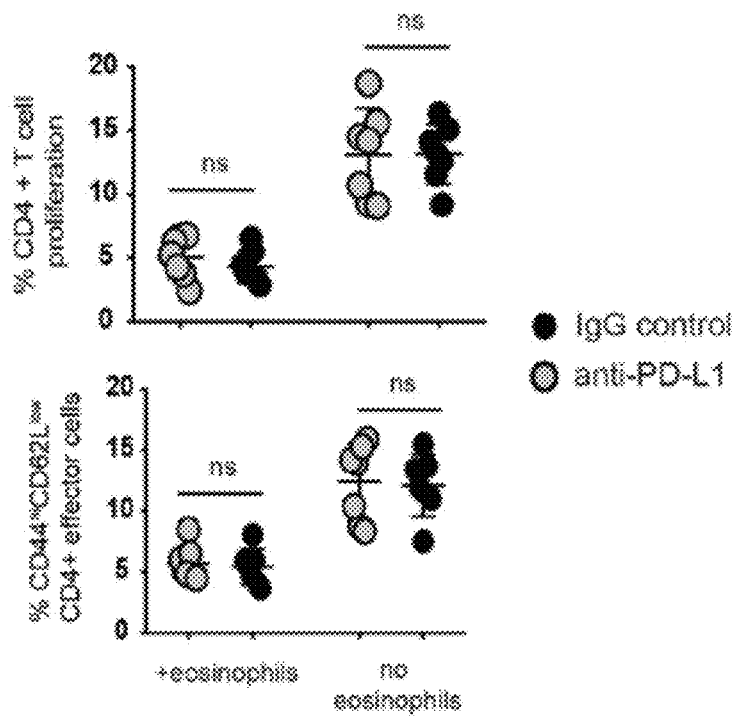

Attention was then directed to PD-L1 due to: (1) its role in lung allograft tolerance and CD8; T cell differentiation (Takahashi et al., 2018); (2) its upregulation during the course of E0 to E1 polarization (FIG. 12A); (3) the increase of its ligand PD-1 on lung-resident T cells after transplantation in vivo (FIG. 5C) and in in vitro during alloreactivity (FIG. 5D) as well as; and (4) data that PD-L1/PD-1 interactions control T cell/dendritic cell synapse formation in the lung (Takahashi et al., 2018). Antibody blockage of PD-L1/PD-1 interactions led to a decrease in number of eosinophil/T cell complexes (FIG. 5E) and increased T cell proliferation and effector differentiation (FIG. 5F and FIG. 12C). Using image stream single cell analysis of T cell and eosinophil co-cultures, it was noted that PD-L1 expression on eosinophils was highly polarized and predominantly sequestered to the membrane region in contact with T cells (FIG. 5G). Thus, eosinophils made direct contact with T cells through PD-L1, which was critical for their suppressive effect. Of note, CD8$^+$ T cells expressed higher levels of the PD-L1 receptor PD-1 compared to CD4$^+$ T cells (FIGS. 5C and 5D). Such data provided a possible explanation of why eosinophil-mediated interaction and suppression is more pronounced for CD8$^+$ rather than CD4$^+$ T cells. Unexpectedly, PD-L1 levels were similar between wild-type and iNOS$^{-/-}$ eosinophils (FIG. 12A) despite the fact that iNOS$^{-/-}$ eosinophils were unable to inhibit T cell proliferation (FIG. 3B). It is thus unlikely that eosinophil-derived PD-L1 directly contributed to downregulation of T cells responses through engagement and signaling via PD-1, but rather acted only indirectly by mediating cell-to-cell interactions.

Example 5

Figure 6A:
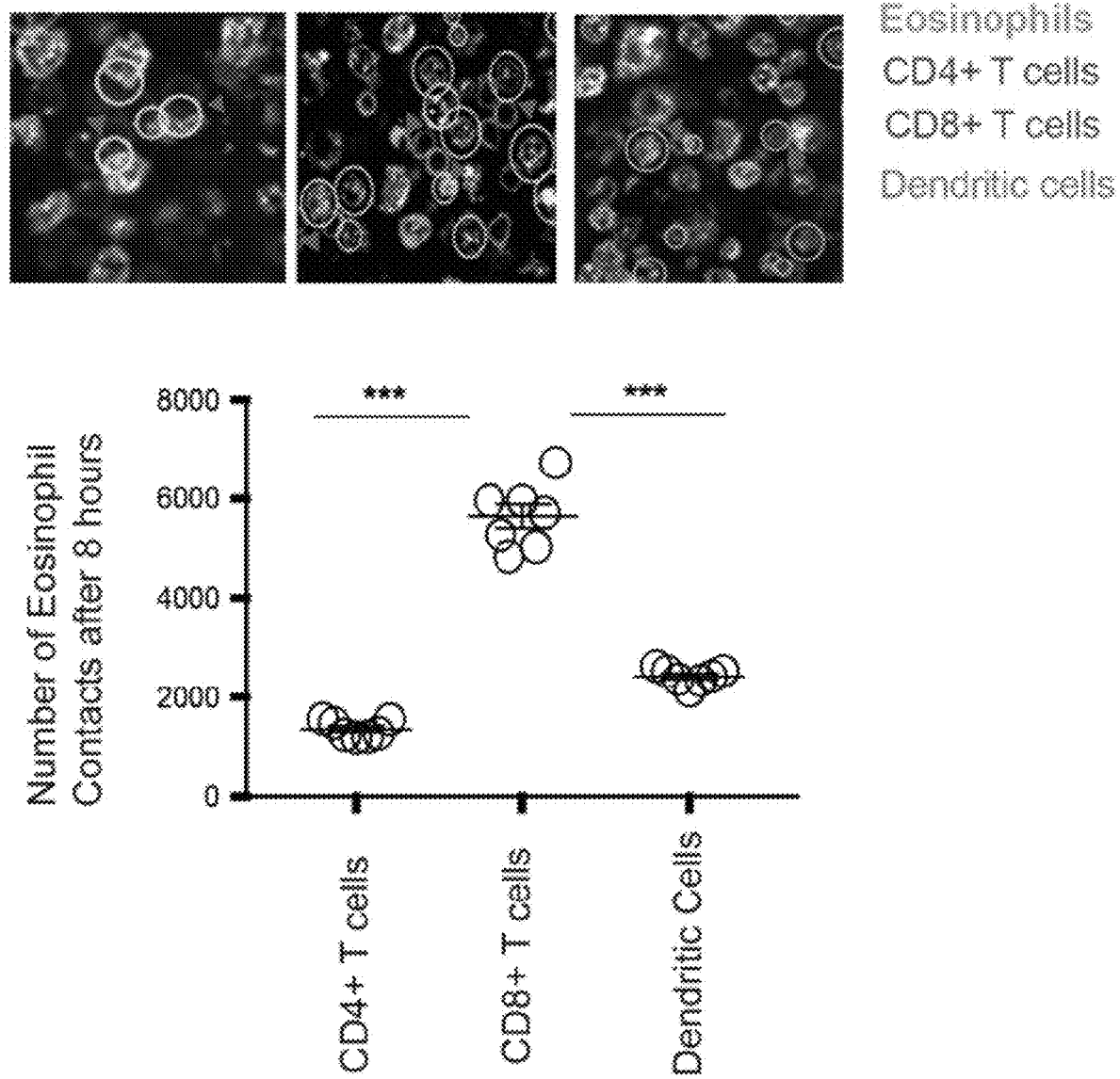
FIGS. 6A and 6B: Eosinophil interaction with and phenotypic alteration of myeloid cells.
Figure 13:
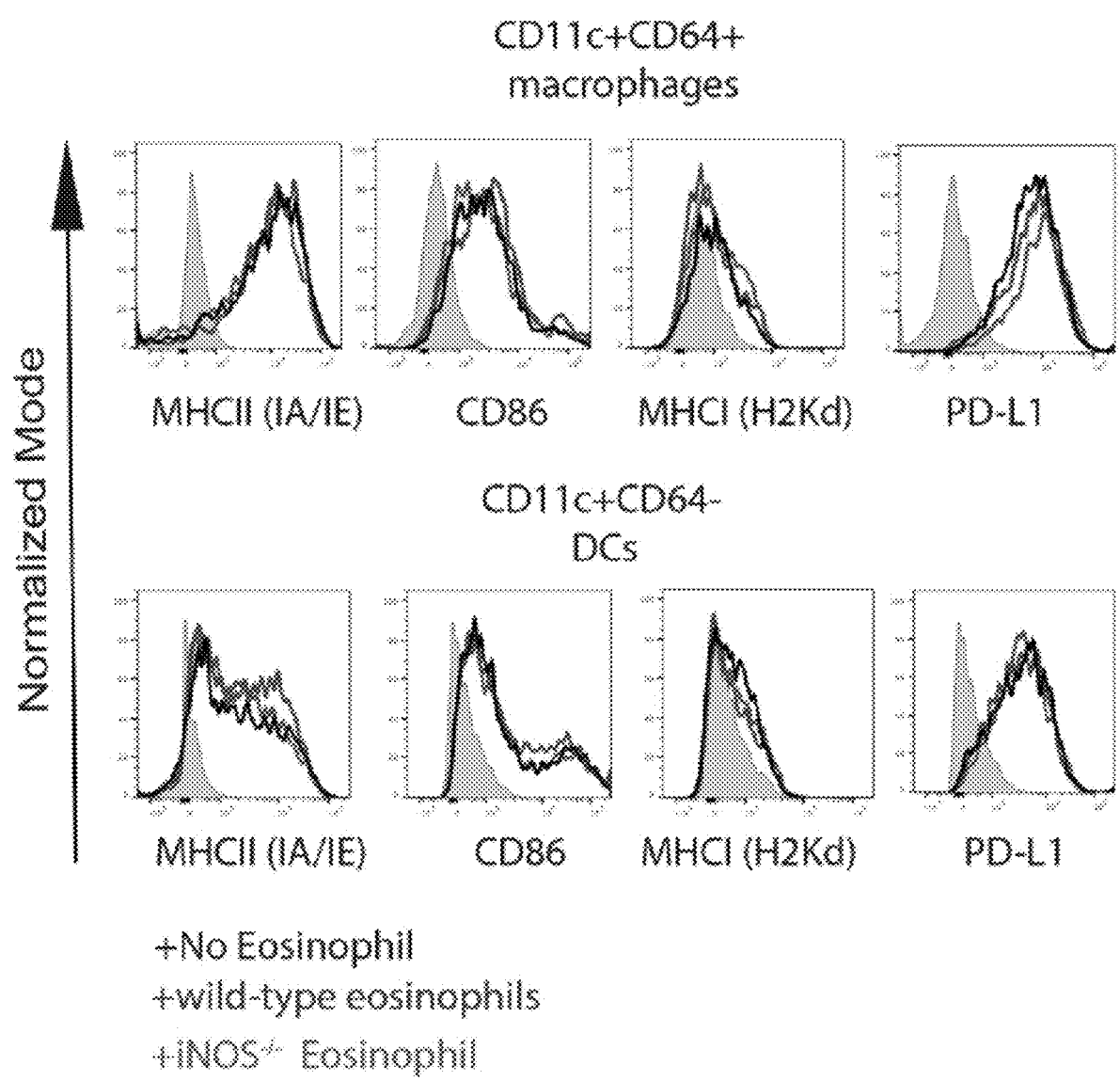
FIG. 13: Phenotype of bone marrow-derived myeloid cells matured by GMCSF in the presence or absence of E1 polarized eosinophils.

Eosinophils do not Directly Inhibit Allogeneic Professional Antigen Presenting Cells In addition to their direct effect on T cell activity, the possibility existed that eosinophils might also influence T cell responses by altering the antigen presenting capacity of professional antigen presenting cells (APCs). This notion is based on work showing that E2-polarized eosinophils could modulate antigen presenting cells to affect Th2 pulmonary immune responses (Lotfi & Lotze, 2008; Jacobsen et al., 2011; Mesnil et al., 2016). However, in in vitro MLRs only limited numbers of dendritic-eosinophil interactions were detected, similar to the low number of CD4$^+$ T cell-eosinophil interactions described herein above (FIG. 6A). In addition, eosinophils did not alter the maturation of bone marrow-derived myeloid cells in vitro (FIG. 13).

Figure 6B:
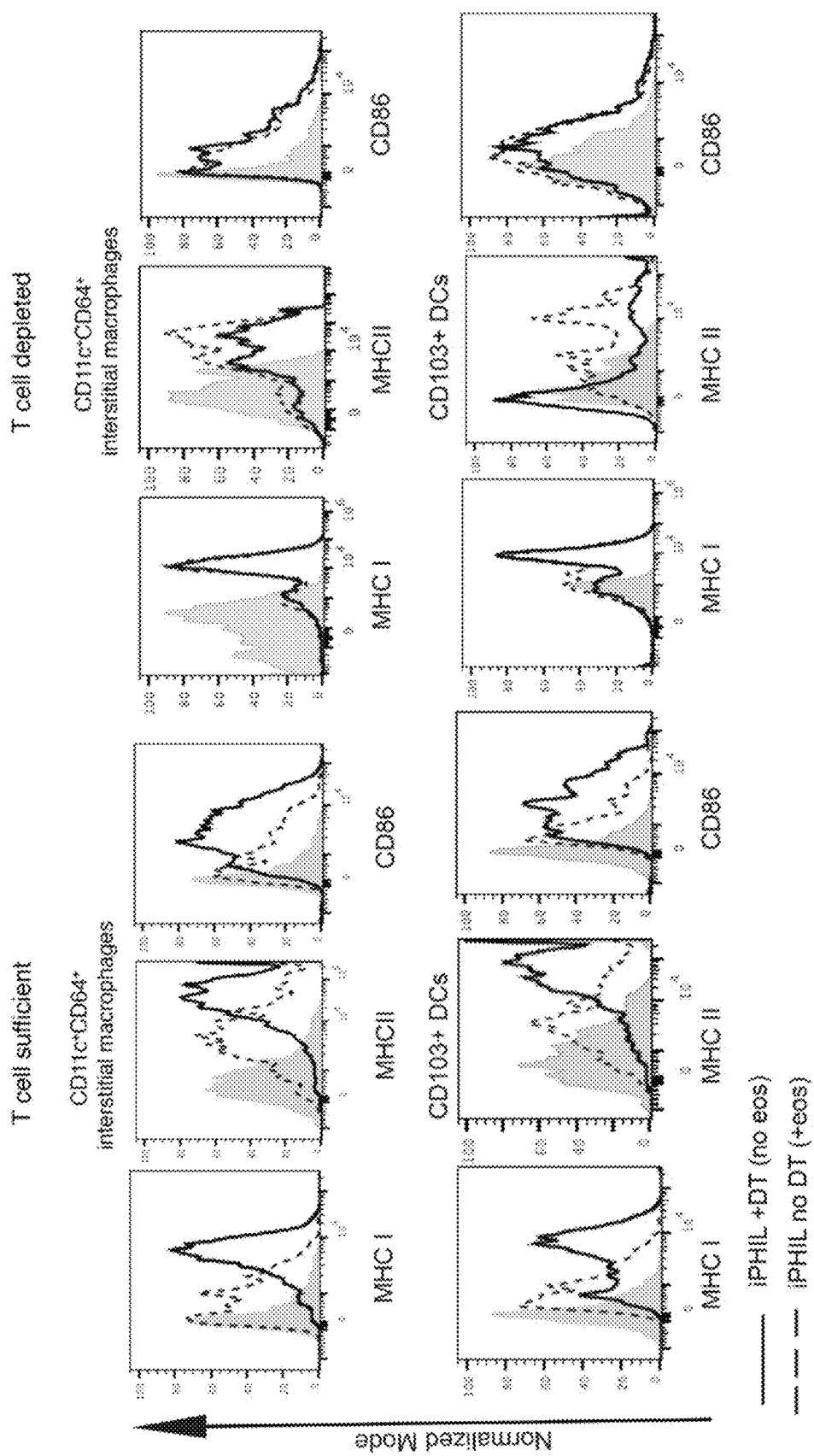

To further evaluate the role of eosinophils in controlling myeloid cell activation in vivo, Balb/c lungs were transplanted to either DT-treated or control B6 iPHIL mice. Both CD11c$^+$/CD64$^+$ interstitial macrophages as well as CD11c$^+$/CD103$^+$/CD64$^-$ dendritic cells expressed higher levels of MHCI and MHCII and co-stimulatory markers following eosinophil depletion (FIG. 6B). Such differences in APC maturation, however, were absent in T cell depleted mice (FIG. 6C), suggesting that effects of T cell activation, rather than the direct action of eosinophils, were responsible for the activation of myeloid cells. Taken together with the T cell-eosinophil contact data, it can be concluded that eosinophil-dependent immunoregulation was primarily due to their direct interactions with T and not myeloid cells.

Example 6

Figures 14A, 14B:
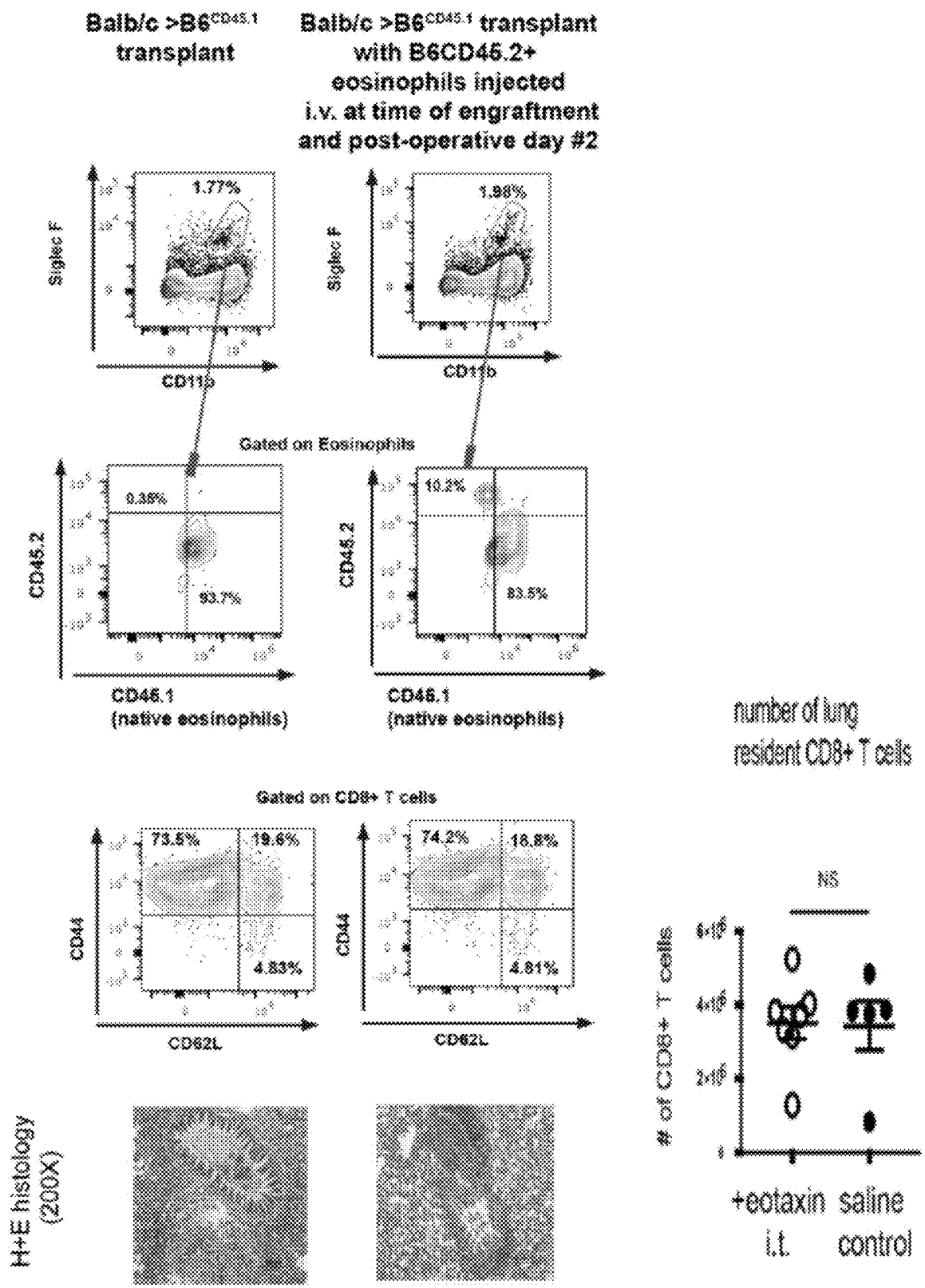
FIGS. 14A and 14B.

Augmenting Eosinophil Recruitment to the Lung Downregulates Alloimmunity and Acute Graft Rejection To evaluate whether eosinophils could be used as a cellular therapy to downregulate alloimmune responses after pulmonary transplantation, 15×10$^6$ B6 eosinophils were administered to B6$^{CD45.1+}$ congenic recipients of Balb/c lungs at the time of engraftment. Only limited numbers of injected eosinophils were observed to have homed to the lung graft with severe graft rejection and CD8$^+$ T cell effector differentiation despite adoptive transfer (FIG. 14A). Thus, an alternative approach was needed to evaluate the role of augmented eosinophil migration on alloimmune responses.

Figure 14C:
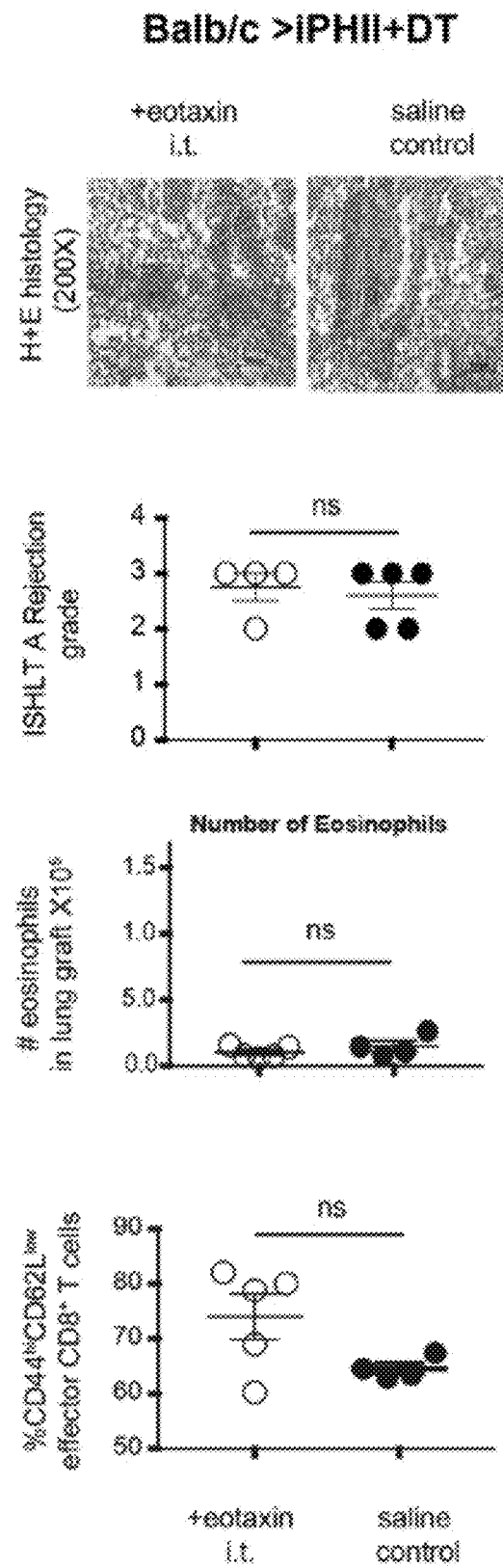
(FIG. 14C) Rejection grade and CD8$^+$ T cell differentiation in Balb/c to DT treated iPHIL lung grafts treated with intratracheal eotaxin 1,2 and IL-5 on days 0 and 1 post engraftment. All statistics performed by unpaired t test. ns p>0.05.

The chemokines eotaxin 1 (CCL11) and eotaxin 2 (CCL24) promote eosinophil migration and homing (Rankin et al., 2000) while IL-5 promotes eosinophil survival (Shen & Malter, 2015). A combination of eotaxin 1, eotaxin 2, and IL-5 were administered intratracheally (Jacobsen et al., 2008) to B6 recipients of Balb/c allografts immediately after, as well as 24 hours following, lung transplantation, and the immune responses were evaluated seven days later in the absence of conventional immunosuppression or CSB. Compared to saline controls, eotaxin-treated mice manifested less inflammation and decreased ISHLT A grade of rejection (FIG. 7A). Eotaxin and IL-5 administration also resulted in higher numbers of graft-resident eosinophils (FIG. 7B). While total numbers of CD8$^+$ T cells in the lung graft did not change, there were significantly fewer CD8/CD44$^{hi}$/CD62L$^{low}$ effector cells in eotaxin/IL-5-treated lungs (FIG. 7C and FIG. 14B). Eotaxin/IL-5-mediated immunosuppression was not evident in eosinophil-depleted mice (FIG. 14C) indicating that this regimen was not directly immunosuppressive on T cells, but relied on eosinophil migration for its function. Collectively, the data suggested that augmenting eosinophil accumulation can be utilized to downregulate lung alloimmune responses.

Materials and Methods Employed in Examples 7-11

Animals.

C57BL/6(B6)$^{CD45.2+}$ (H2$^b$), B6.SJL/BoyJ$^{B6CD45.1+}$ (H2$^b$) and Balb/c (H2$^d$) mice were obtained from The Jackson Laboratory (Bar Harbor, Maine). ΔdblGATA (C.129S1(B6)-Gata1$^{tm6Sho}$/J) GATA mutant mice on a Balb/C background were purchased from Jackson Laboratory as well but then bred and expanded at the University of Virginia along with Balb/C wild-type control mice. NJ1638 IL-5 overexpressing hypereosinophilic transgenic mice were developed at the Mayo Clinic (Scottsdale, Arizona; Lee et al., 1997) and bred in the same laboratory or colonies bred and maintained at the vivarium facility at the University of Virginia School of Medicine. The animals passed all necessary genotyping screening or quarantine serological tests for those that were transported from one University to the other, before they were used in this study. All mice used in this study were between 8 and 10 weeks old.

Surgery and Transplantation.

Orthotopic transplantation of a left lung allograft was carried out according to our previous reports. To achieve allograft acceptance mice were treated either with double co-stimulatory blockade of the CD28/B7 and the CD40/CD40L pathways as previously described (Larsen et al., 1997; Krupnick et al., 2014) or high dose cyclosporine A and low-dose methylprednisolone as described (Chen et al., 2013).

Histology.

Lungs were fixed in formaldehyde, sectioned and stained with Hematoxylin and Eosin (H+E). A lung pathologist blinded to the experimental conditions graded graft rejection using standard criteria (International Society for Heart and Lung Transplantation (ISHLT) A Grade) developed by the Lung Rejection Study Group (Yousen et al., 1996).

Preparation of Lung Cells.

Lung tissue derived from resting or graft recipient mice was well minced with scissors and digested by placing them into RPMI 1640 medium (Thermo Fisher) containing 0.5 mg/ml collagenase II (Worthington Biochemical Corporation, Lakewood, New Jersey) and 5 U/ml DNAse (Sigma, St. Louis, Missouri) for 60 minutes at 37° C. in a shaker. The digested lung tissue was passed through a 70 μm cell strainer and treated with ACK lysing buffer (Lonza, Walkersville, Maryland) to remove red cell contamination. This digestion methods have been previously described (Krupnick et al., 2014).

Flow Cytometry.

All antibodies for flow cytometry were primarily fluorochrome-conjugated rat anti-mouse monoclonal antibodies. Thus, staining of samples was by direct immunofluorescence. Intracellular staining was performed as previously described (Gelman et al., 2008). The following antibodies were purchased from BD Biosciences, (San Jose, California): anti iNOS FITC, anti Ly6G (clone IA8) APC, anti integrin β7 PE, anti Siglec-F PE or PerCPCy5.5, anti Gr-1 PE or APC, and anti CD127 APC. Antibodies purchased from Biolegend (San Diego, California) include anti Ly6C PE-Cy7, anti CCR3 PE or PE-Cy7 and anti CD49d APC, while the following antibodies were purchased from Thermo Fisher—eBiosciences (San Diego, California): anti CD45 eFluor-450, anti CD45.2 eFluor-450 or eluor-506, anti CD45.1 APC-eFluor-780, anti CD11b PerCPCy5.5 or APC-eFluor-780, anti CD8a FITC or APC-eFluor-780, anti CD90.2 FITC or APC-eFluor-780, anti CD11c PerCPCy5.5 or APC-eFluor-780, anti F4/80 PE or PerCPCy5.5, anti CD206 PE, anti CD68 PE, anti CD38 PE, anti CD31 APC, anti CD4 APC or eFluor 506, anti CD44 PerCPCy5.5, anti CD62L PE-Cy7 and anti Ki-67 PE. All fluorochrome conjugated antibodies were matched with the corresponding Rat IgG isotypes as antibody controls. In addition, FMO controls were also used to separate the negative and positive populations. Dead cells were excluded with Live/Dead Fixable Stain (Thermo Fisher). To block non-specific binding to Fc-receptors, we used anti CD16/CD32 (Thermo Fisher). Cells expressing various markers of interest were acquired either in a BD Canto II, equipped with three lasers for 10 parameters detection or BD LSR Fortessa equipped with four lasers for 18 parameters detection (BD Biosciences, San Jose, California) or in FACS Scan upgraded with three lasers for 10 parameter detection capacity (Cytek development, Fremont, California). Quality controls were performed daily on the flow cytometers according to manufacturer's instruction.

Fluorescent Activated Cell Sorting for Lung Eosinophil.

Eosinophils were sorted as CD45$^+$CD11b$^+$Siglec$^-$CD11c$^-$ cells following the staining of digested lungs with a panel of fluorochrome-conjugated antibodies similar to the ones used for flow cytometry. Sorting was done using the BD Influx (BD Biosciences) or Sony SY3200 "Synergy" Cell Sorter (Sony Biotechnology, San Jose, California).

Differential Staining for Leukocytes.

Cytospin-slides of sorted CD45$^+$CD11b$^+$Siglec$^-$F$^+$CD11c$^-$ recipient mice lung graft cells were stained using the Hema 3 staining kit (Fischer Scientific, Waltham, Massachusetts), a Romanowsky stain variant. Staining was done according to the manufacturer's instruction.

Nitric Oxide Measurement.

Nitric Oxide Assay Kit (Colorimetric; Abcam, Cambridge, Massachusetts), based on the Greiss reagent was used for the measurement of NO concentration in the lung. Lung tissues were homogenized using GentleMacs Dissociator (Miltenyi Biotec, San Diego, California) and other sample preparation procedures were according to manufacturer's recommendations. Prepared samples were analyzed in iMark Microplate Absorbance Reader (Bio-Rad, Hercules, California).

Isolation, Culture and Polarization of Mouse Peripheral Blood Eosinophil.

Eosinophils were isolated from peripheral blood of the hypereosinophilic IL-5 transgenic mice (NJ.1638) after density dependent separation of the eosinophil-rich white blood cells using a combination of Histopaque 1119 and 1083 (Sigma-Aldrich) at a ratio of 1:9, followed by negative selection of >98% pure eosinophil population after incubation of white blood cells with immunomagnetic beads conjugated with CD45R/B220 and CD90.2/Thy.2 antibodies (Miltenyi Biotech, San Diego, California). The purity of eosinophils was confirmed by flow cytometry (CD45$^+$CD11b$^+$Siglec-F$^+$CCR3$^+$ cells). Details of the cell preparation and eosinophil purification protocol are as previously described (Jacobsen et al., 2015). To obtain polarized eosinophils, purified eosinophils were cultured at 5×10$^5$/ml concentration for 18-24 hours in RMPI-1640 media (containing glutamine and 25 mM HEPES) (Thermo Fisher) supplemented with 10% FBS, 10 U/ml Penicillin, 10 µg/ml Streptomycin, 29.2 µg/ml L-Glutamine, and 55 µM ß-Mercaptoethanol; and in addition, E0 culture also included 10 ng/ml IL-5, E1 included 10 ng/ml IL-5, 15 ng/ml IFN-γ, 15 ng/ml TNF-α, while E2 culture also had IL-5 10 ng/ml, IL-33 30 ng/ml, IL-4 10 ng/ml, and GM-CSF 10 ng/ml. All cytokines and growth factors used for eosinophil polarization culture were purchased from Peprotech (Rocky Hill, New Jersey).

In Vitro Mixed Lymphocyte Reaction.

Stromal cells from Balb/cJ mice (CD45.2) and CD90.2 positive cells from B6.SJL/BoyJ mice (CD45.1) were respectively obtained by negative and positive selection, respectively, by Manual activated Cell Separation (MACS) using CD90.2$^+$ MicroBeads (Miltenyi Biotech). Labeled or unlabeled CD45.1$^+$ CD90.2$^+$ cells were cultured together with the CD45.2$^+$ stromal cells in a round-bottomed 96-well plate at a ratio of 1:3 (CD90.2$^+$ cells: stromal cells). In some cases, CD45.2$^+$ eosinophils isolated from IL-5 transgenic (NJ. 1638) mice were also added to the culture at the same number as the CD90.2$^+$ cells isolated from B6.SJL/BoyJ (CD45.1$^+$) mice. Proliferation of the CD90.2$^+$ cells were analyzed flow cytometrically by Ki-67 expression after five days of culture.

In Vivo Antibody-Mediated Cytokine Neutralization.

All neutralization antibodies are of rat origin and purchased from BioXcell, West Lebanon, New Hampshire. For the targeted depletion of eosinophils in allograft recipients, 200 µg of anti-IL5, clone TRFK5 was administered to each mouse on days −2, −1, +1, and +2 post-transplantation. For the neutralization of IFN-γ and TNF-α, 500 µg each of the respectively blocking antibodies, clones XMG1.2 and XT3.11 respectively, were administered together in a cocktail twice every other day pre-transplant and twice every other day post-transplant for a total of four doses. Each control animal for all the antibody mediated cytokine neutralization experiments received an equivalent concentration of rat IgG control, clone HRPN.

In Vitro Antibody-Mediated Cytokine Neutralization.

IFN-γ and TNF-α, were neutralized in vitro using 10 µg/ml and 25 µg/ml respectively of the same blocking antibodies used for in vivo neutralization experiments. The antibodies were added twice on the culture set-up days and on day 3 post set-ups.

Quantitative Polymerase Chain Reaction (qPCR).

RNA was extracted from lung digests, eosinophils isolated from the lung or in vitro polarized eosinophils using the TRIzol based technique according to manufacturer's guidelines (Thermo Fisher). cDNA was reverse-transcribed from RNA samples using the High Capacity cDNA Reverse Transcription Kit in accordance with manufacturer's instruction (Thermo Fisher—Applied Biosystem). qPCR was run on the cDNA samples using Power Syber Green PCR Master Mix (Thermo Fisher—Applied Biosystem) in a CFX-96 Real-Time PCR Detection System (Bio-Rad). Cycling and reaction conditions were as provided by the manufacturer. The sequences of the oligonucleotide primers used are as set forth in the Materials and Methods Employed in EXAMPLES 1-6 (i.e., SEQ ID NOs: 7-34).

Statistics.

as set forth in the Materials and Methods Employed in EXAMPLES 1-6.

Example 7

Figure 15A:
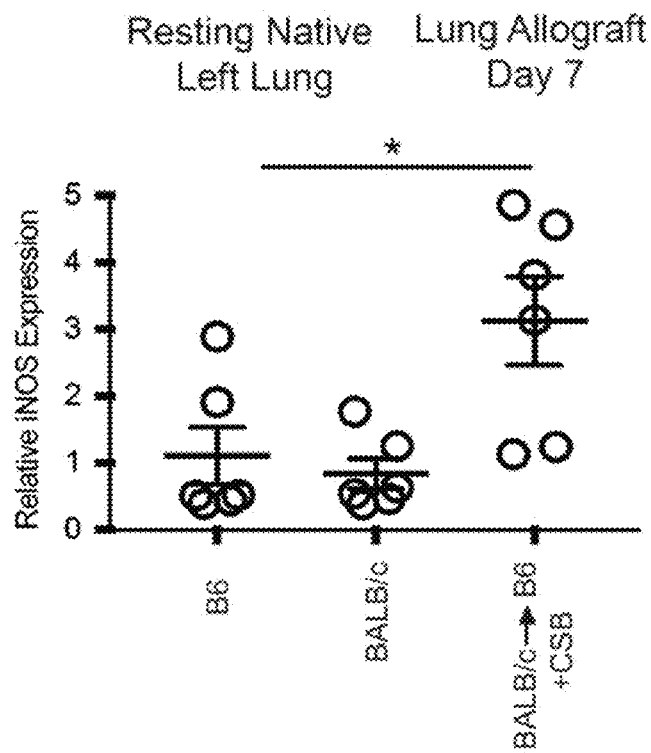
FIGS. 15A-15D: Accepting Lung Allografts are Infiltrated by Recipient-Derived iNOS$^+$ Cells.
Figure 15B:
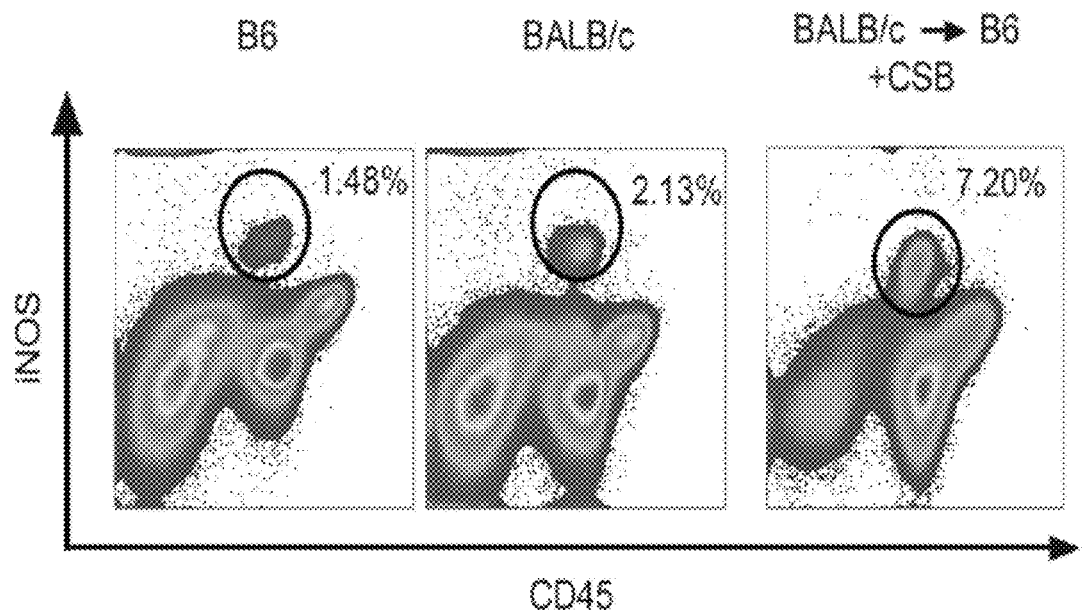
Figure 15C:
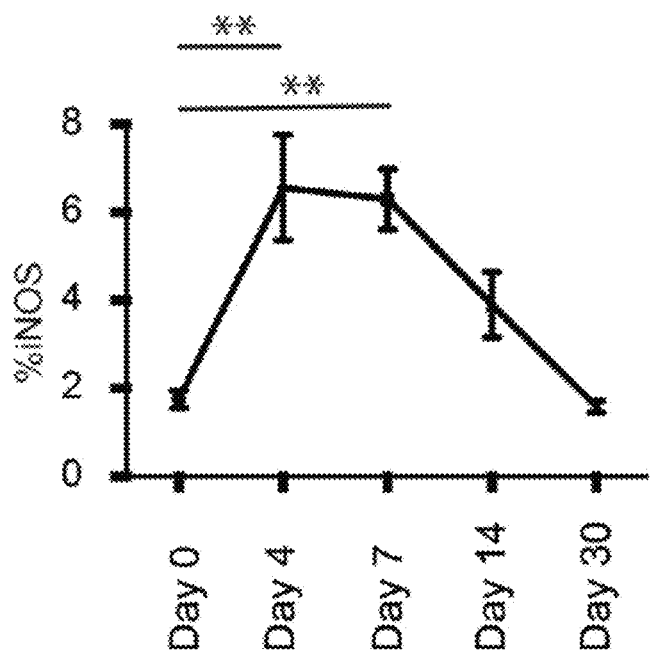
Figure 15D:
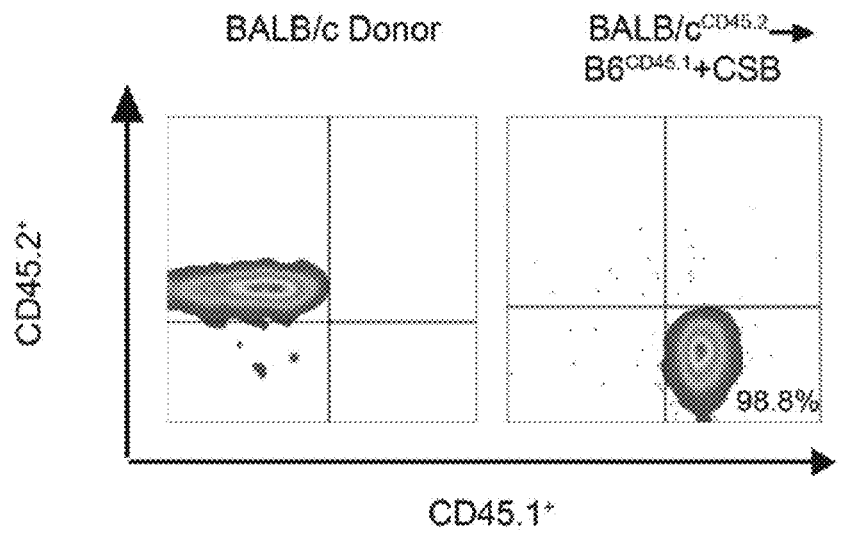

Tolerance is Associated with an Influx of Recipient-Derived iNOS+ Cells into the Lung Allografts Consistent with previous disclosure that recipient iNOS expression is critical for promoting lung allograft acceptance (Krupnick et al., 2014), a relative increase in iNOS transcripts in co-stimulatory blockade (CSB)-treated lung allografts compared to resting lungs was detected (FIG. 15A). Flow cytometric analysis demonstrated a relative increase in iNOS' hematopoietic cells within the graft (FIG. 15B). An early rise in this cell population was observed, peaking on days 4-7 post-transplantation, that returned to baseline by day 30 post-engraftment (FIG. 15C). Transplantation of a $CD45.2^+$ Balb/c lungs into $CD45.1^+$ congenic C57BL/6 recipients ($B6^{CD45.1}$) confirmed that the iNOS+ cells were exclusively of recipient origin (FIG. 15D).

Example 8

Eosinophils are the Dominant iNOS Expressing Cells in the Lung Allograft

Figure 16A:
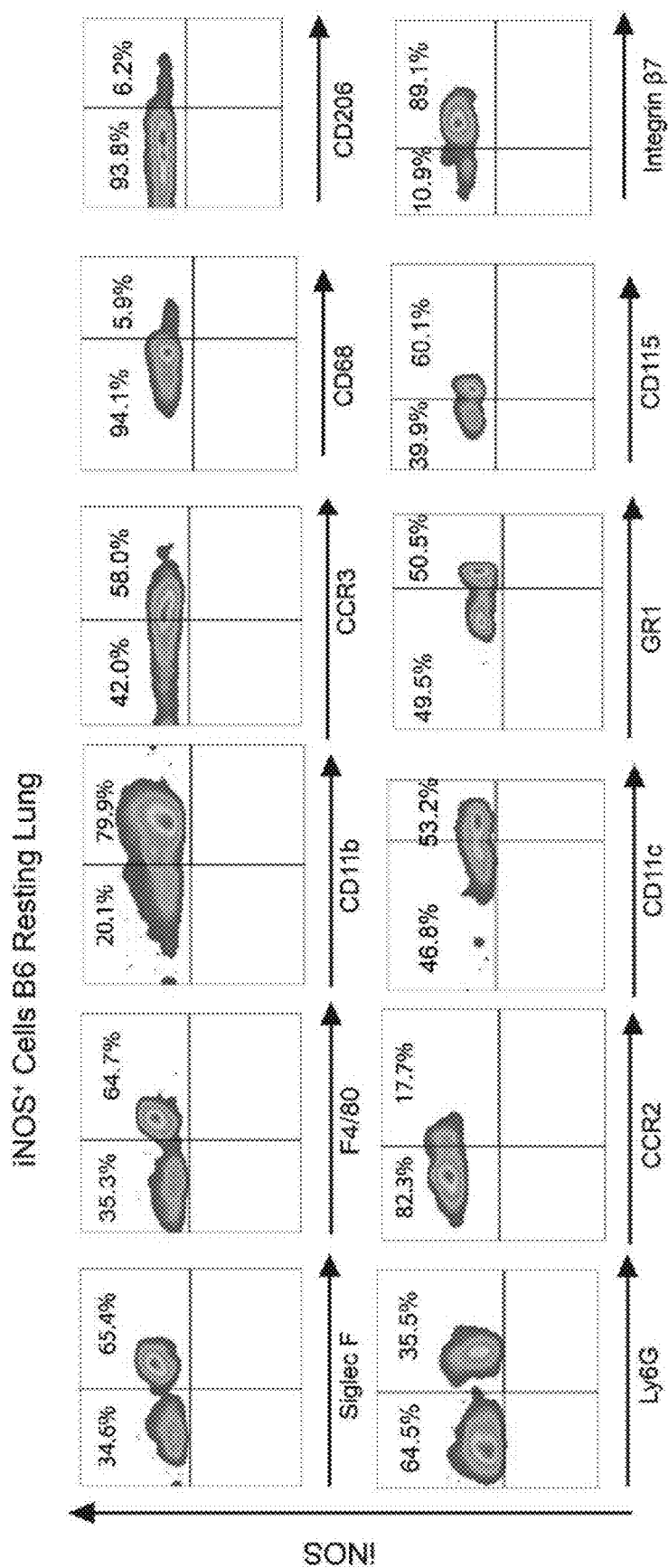
FIGS. 16A-16C: Phenotype of iNOS$^+$ Cells from Resting Lung and Lung Allografts (FIG. 16A) iNOS$^+$ in resting B6 left lung is a heterogeneous population (representative of seven transplants).
Figure 16B:
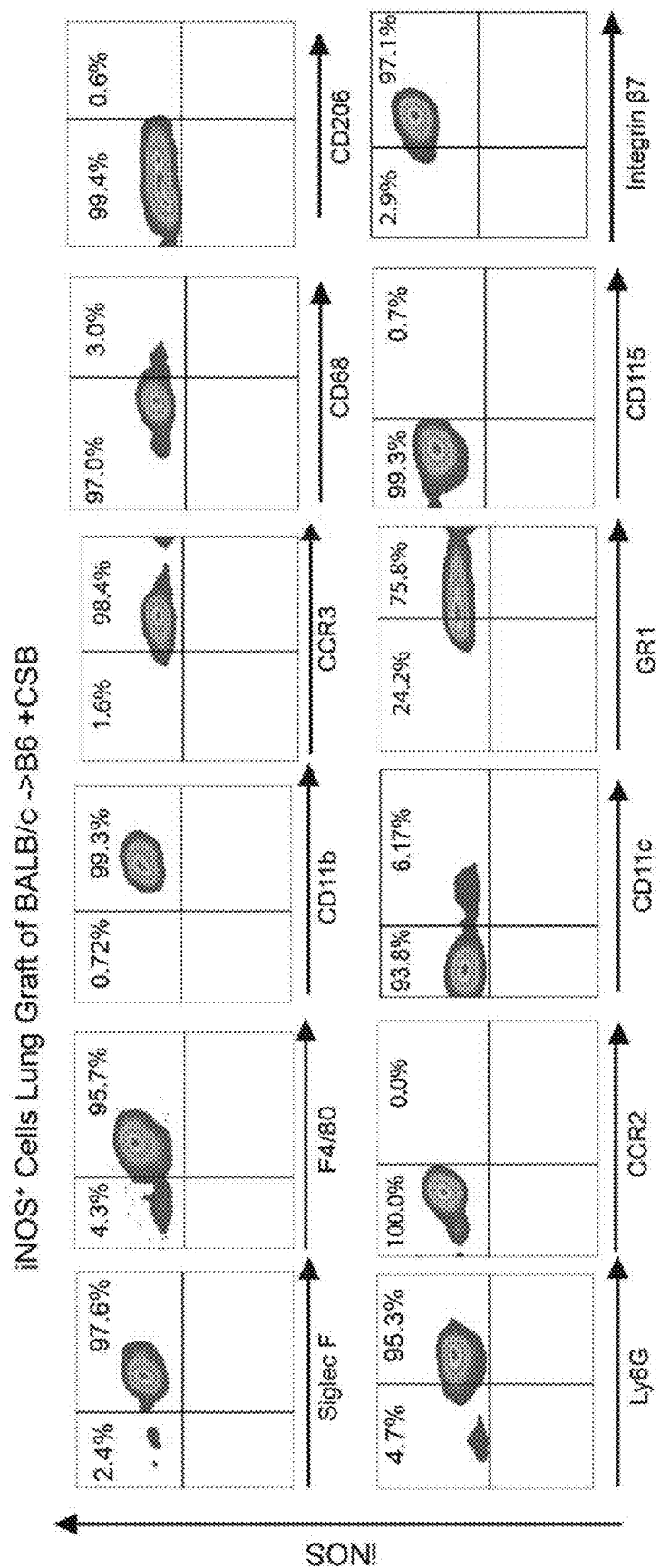
Figure 16C:
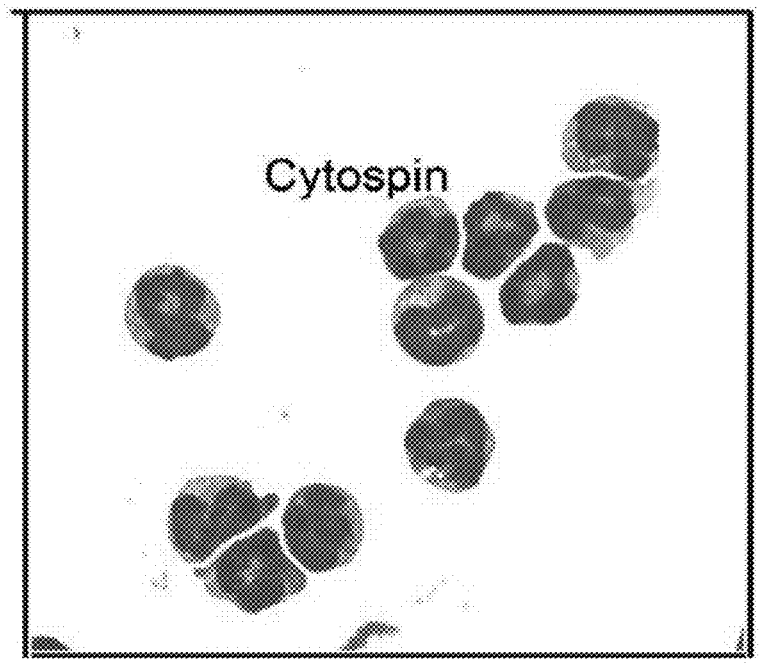
Figure 22A:
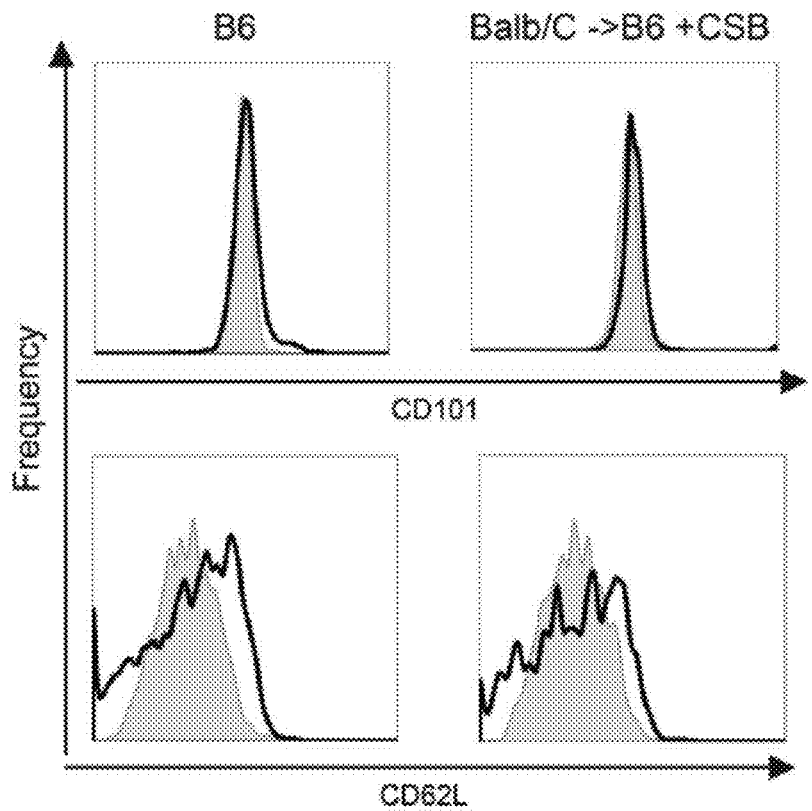
FIG. 22A-22C.
Figure 22B:
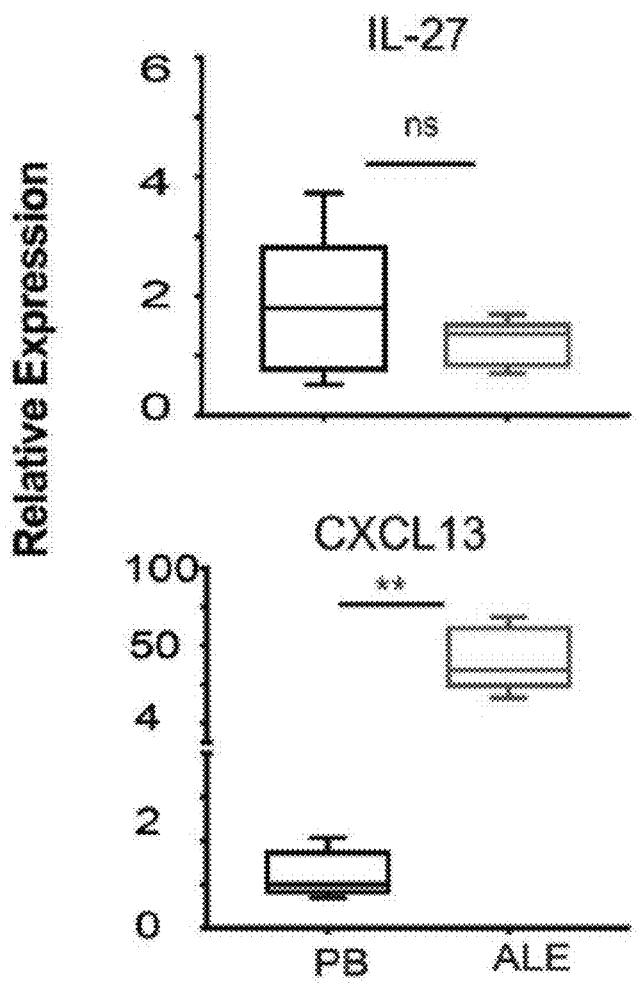

The iNOS+ lung-resident cells after transplantation were investigated. In resting murine lungs, iNOS was detectable in a heterogeneous cell population containing a mixture of myeloid and granulocytic cells (FIG. 16A). Within one week of transplantation, however, iNOS+ cells in the lung were a homogeneous population of $SiglecF^+F4/80^+CD11b^+CD11c^-CCR3^+CCR2^-CD68^-CD115^-GR1^+$, cells consistent with an eosinophil phenotype (FIG. 16B; Lee et al., 2012; Percopo et al., 2016). Romanowsky staining of flow cytometrically sorted cells demonstrated an intense eosinophilic cytoplasmic staining with a characteristic eosinophil-defining ring-shaped nucleus (FIG. 16C). Both the resting and the accepting lung eosinophil expressed very low levels of CD62L, while neither of the two expressed CD101, indicating a possible regulatory capacity of the eosinophil from both models (Mesnil et al., 2016; FIG. 22A). Furthermore, the accepting lung eosinophil express high levels of CXCL13 transcript without any significant expression of IL-27, and therefore, might differ from the $Gr-1^{hi}$ eosinophils that are associated with increased CXCL13+ and IL-27 transcripts (FIG. 22B; Percopo et al., 2016).

Figure 17A:
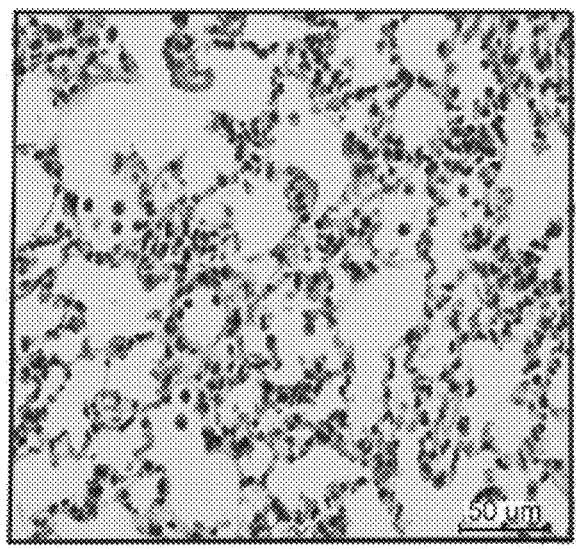
FIGS. 17A and 17B: Tissue Distribution and Quantification of Eosinophils (FIG. 17A) Seven days post-transplantation of a Balb/c to B6 lung allografts with CSB immunosuppression reveals that eosinophils are distributed throughout the periphery of the lung in the alveolar space and septae as indicated by the arrows. Left figure is an H+E stain with right figure a major basic protein-1 immunohistochemistry.
Figure 17A:
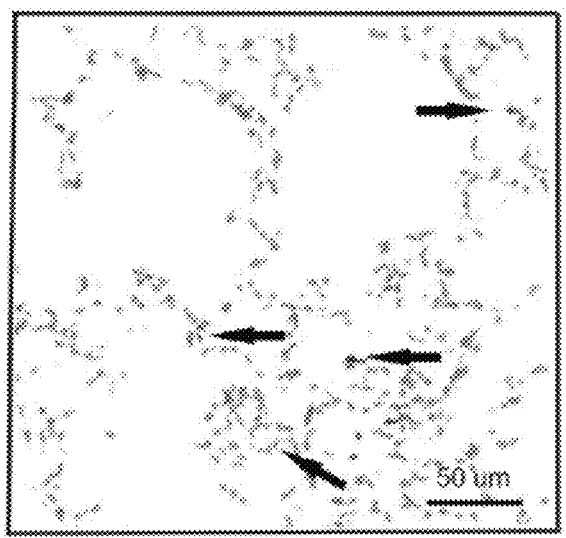
Figure 17B:
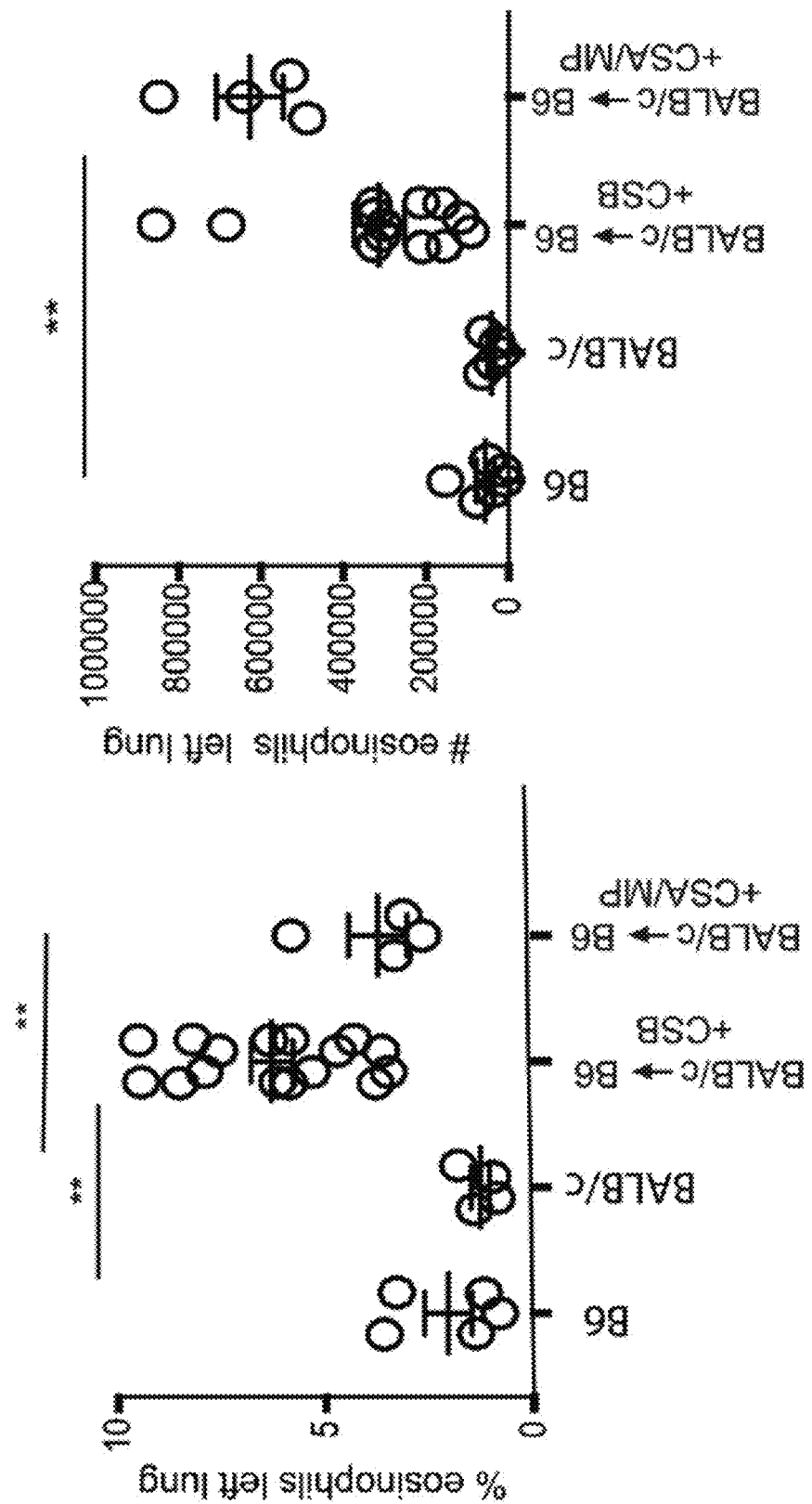

Lung allografts were also examined by both histology and eosinophil major basic protein-1 based immunohistochemistry and determined that eosinophils were located primarily within the alveolar space as well as alveolar septa (FIG. 17A). Quantitative analysis of accepting left lung allograft revealed an increase in both the relative percentage and total number of lung-infiltrating eosinophils over resting lungs (FIG. 17B). Such eosinophil influx was evident with graft acceptance induced by CSB as well as cyclosporine and low dose methylprednisolone (FIG. 17B; Chen et al., 2013). Thus, despite the prevailing notion that eosinophils promote deleterious inflammatory responses in the lung, eosinophils represent the dominant iNOS-producing cells in the lung allograft and pulmonary eosinophilia is associated with allograft acceptance.

Example 9

Figure 18A:
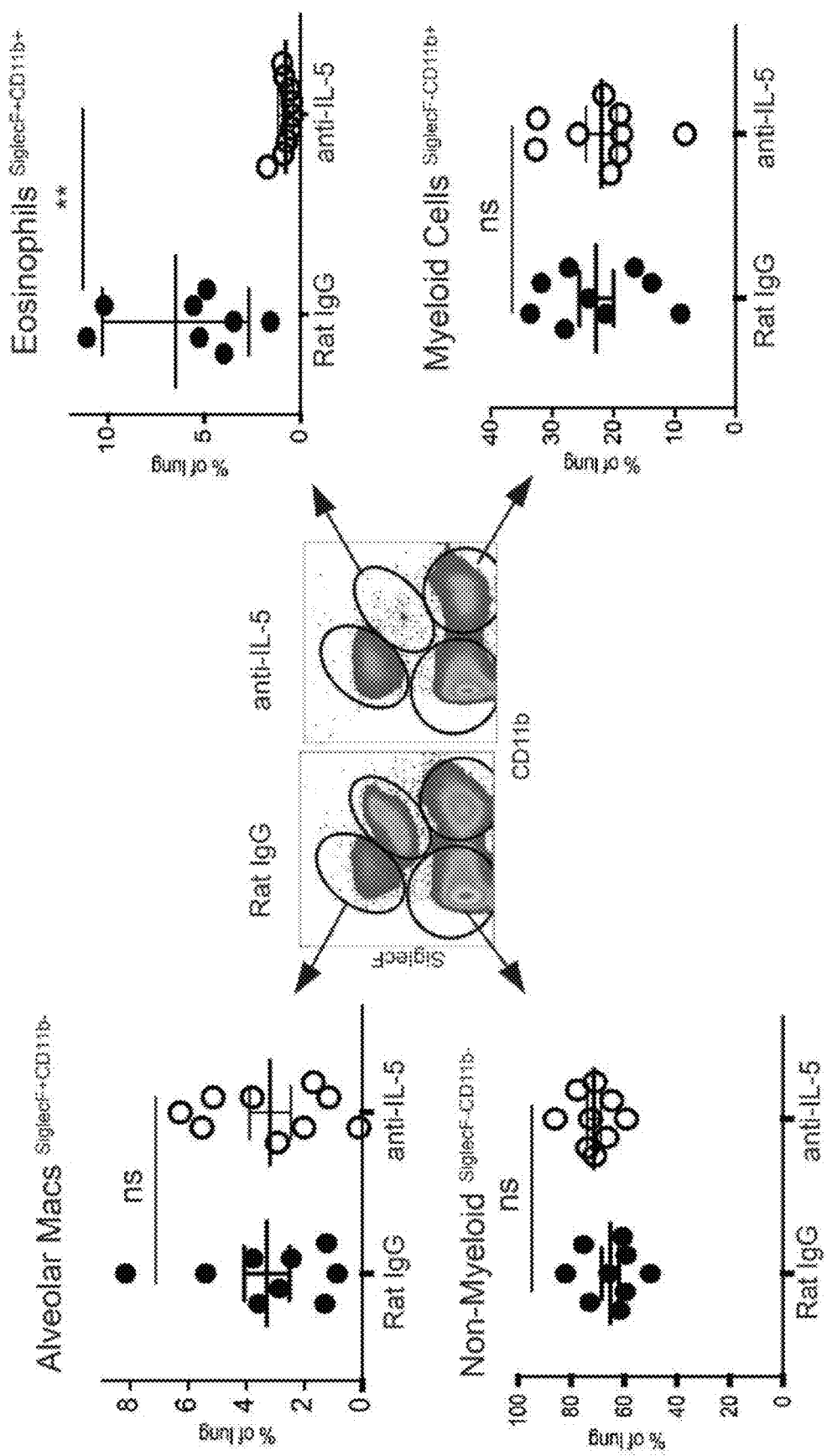
FIGS. 18A-18D: Eosinophil Depletion Eliminates NO Production and Potentiates a CSB-Resistant Form of Lung Allograft Rejection.
Figure 18B:
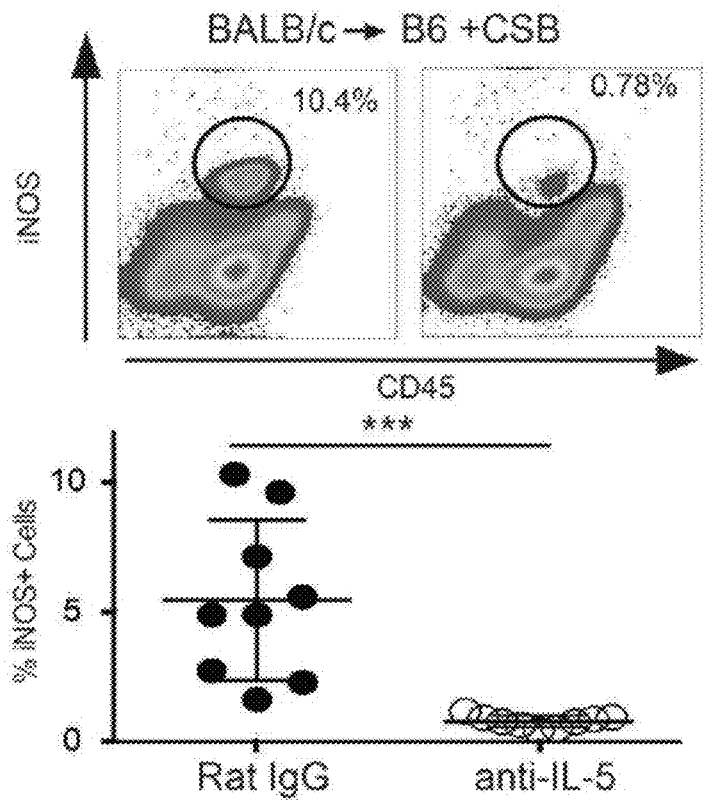
Figure 18C:
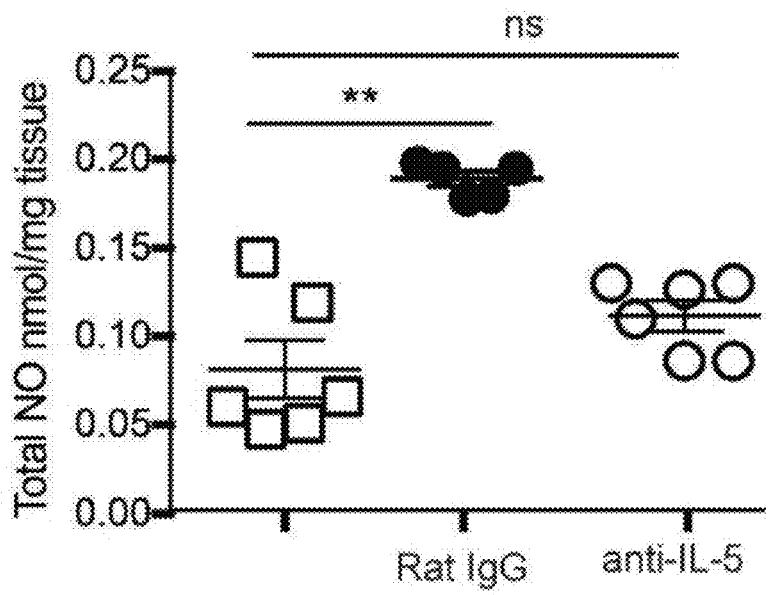
Figure 18D:
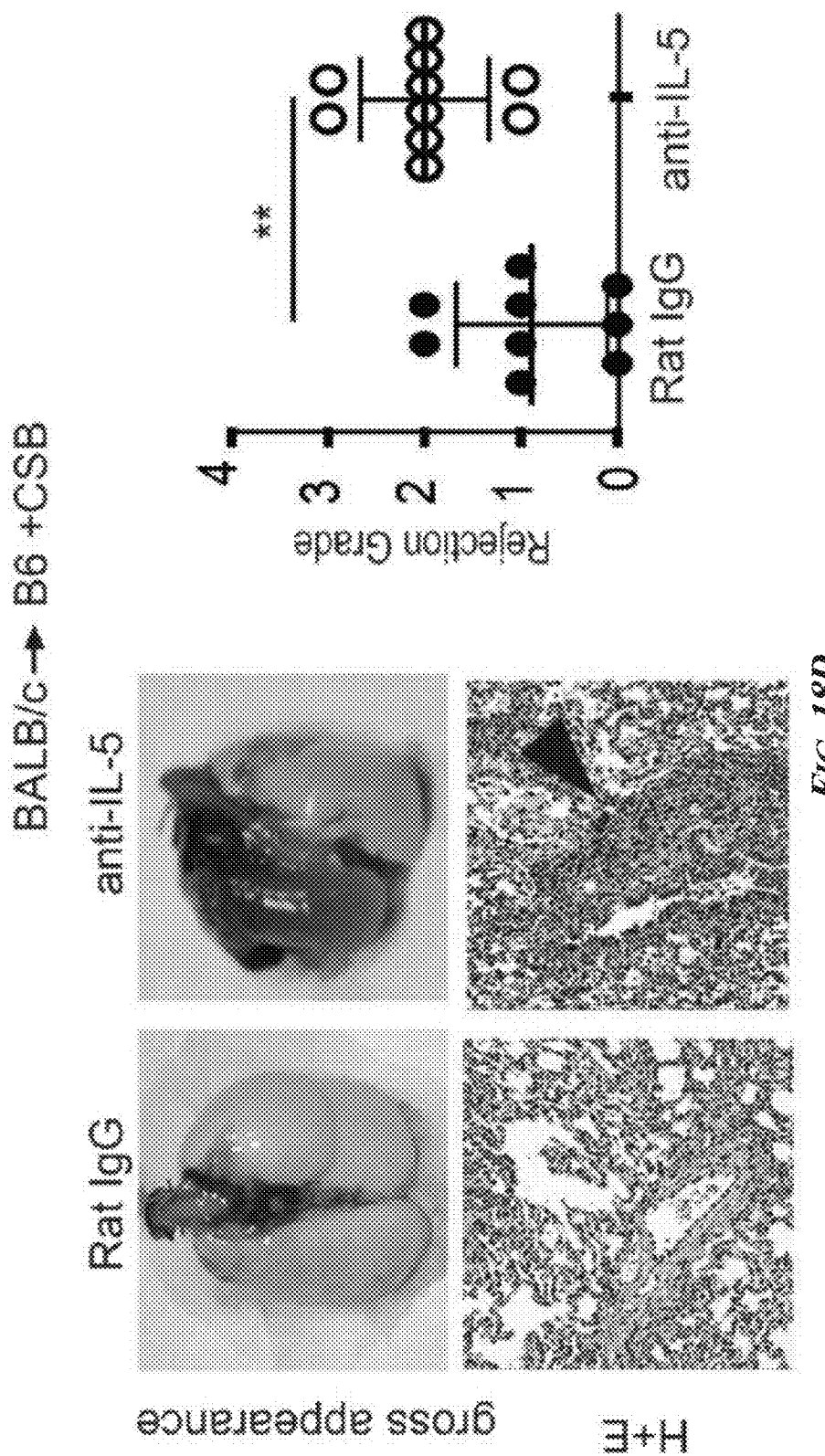

Eosinophils Play a Critical Role in NO Production and Lung Allograft Acceptance Whether eosinophils are necessary for tolerance induction after lung transplantation was tested. Interleukin-5 (IL-5) is the critical factor for eosinophil generation, migration, maintenance and survival (Fulkerson & Rothenberg, 2013). Neutralization of this cytokine is a commonly accepted method for global eosinophil ablation in experimental murine models (Yang et al., 1997, Mesnil et al., 2016) and therapeutic intervention for asthma (Nair et al., 2009) and hyperoesinophilic patients (Roufosse et al., 2013). IL-5 was neutralized in immunosuppressed B6 recipients of Balb/c lung allografts. Such treatment resulted in the near complete elimination of graft-resident $SiglecF^-CD11b^+$ eosinophils but did not alter $SiglecF^+CD11b^-$ alveolar macrophages, $SiglecF^+CD11b^+$ myeloid cells, or $SiglecF^-CD11b^-$ nonmyeloid cells (FIG. 18A). Depletion of eosinophils also led to the near complete elimination of iNOS' cells in the lung allograft (FIG. 18B) and reduced graft NO production to levels comparable to $B6^{iNOS-/-}$ recipients (FIG. 18C). Most importantly, lung allografts were acutely rejected after IL-5 neutralization despite CSB (FIG. 18D). Such data demonstrated that eosinophils were the dominant NO-producing cells in the lung after transplantation and in their absence, other cells were not able to produce sufficient NO to promote tolerance.

Figure 22C:
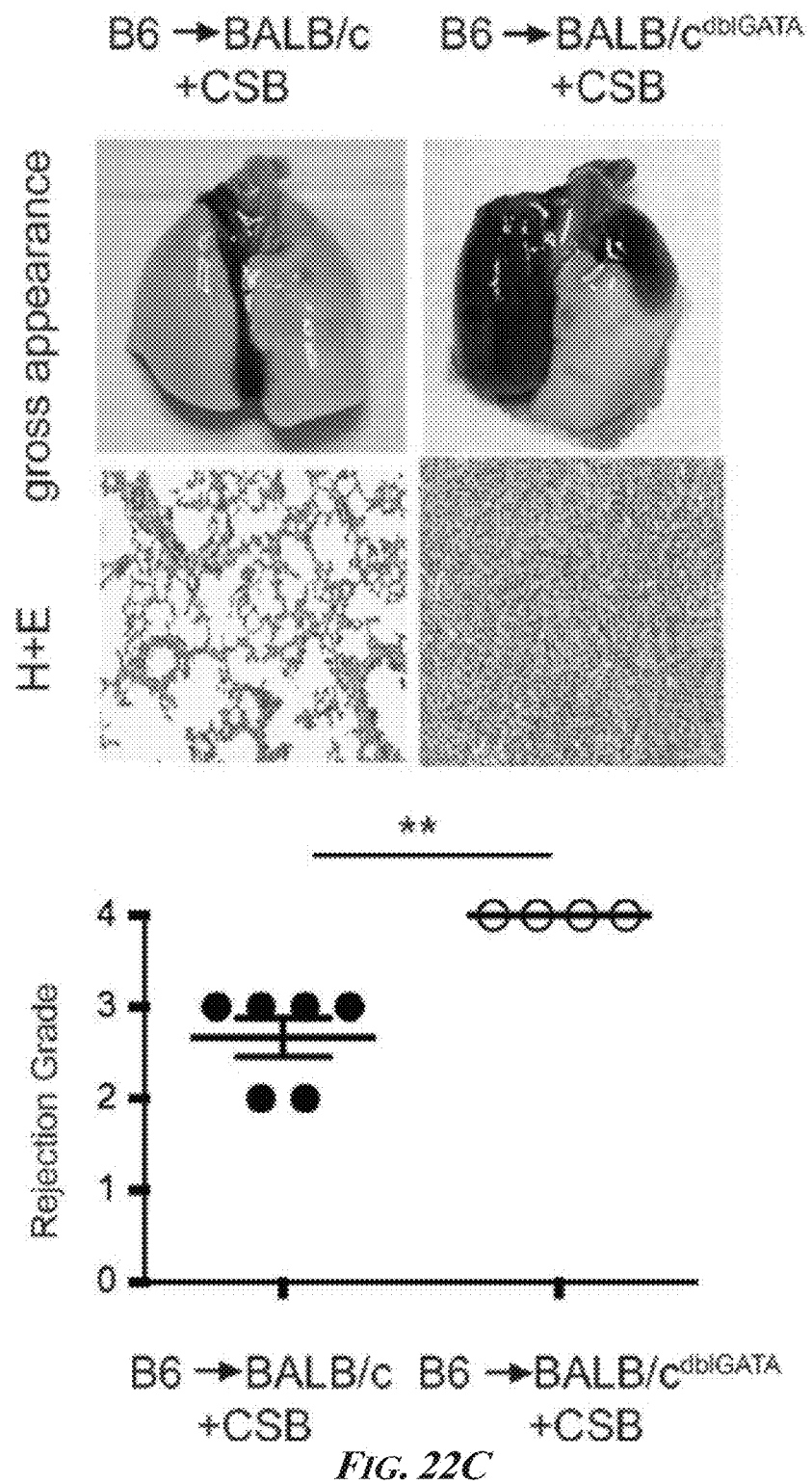

To further evaluate these results in an independent model of eosinophil deficiency, B6 lung allografts were transplanted to either wild-type Balb/c or ΔdblGATA eosinophil mice on a Balb/c background with CSB. A significant increase in graft rejection in ΔdblGATA recipient mice was observed, with near complete graft destruction and severe rejection by day seven post transplantation compared to Balb/c controls (FIG. 22C). Taken together with data described above, it can be concluded that eosinophils played a crucial role in lung allograft acceptance.

Example 10

Accepting Lung Allografts Demonstrate Th1 Polarization

It has been previously observed that environmental polarization can alter the phenotype and function of eosinophils in asthma models, which are Th2 (IL-33, GM-CSF, IL-4) cytokine-producing (Jacobsen et al., 2015). In fact, eosinophils can undergo either Th1 or Th2 induced polarization based on environmental cytokine milieu (Liu et al., 2007). While it has been previously described that IFN-γ and TNF-α, Th1-related cytokines, induce iNOS in several experimental models (Morikawa et al., 2000; Fonseca et al., 2003; Krupnick et al., 2014), very limited data exists on iNOS induction in eosinophils (Drake et al., 2016). In fact some have suggested that Th-2 polarizing cytokines, such as IL-4, may induce iNOS in this cell population (Paoliello-Paschoalato et al., 2005). The possibility that the cytokine milieu in the lung allograft might generate iNOS-expressing eosinophils with regulatory potential after transplantation was thus tested.

Figure 19A:
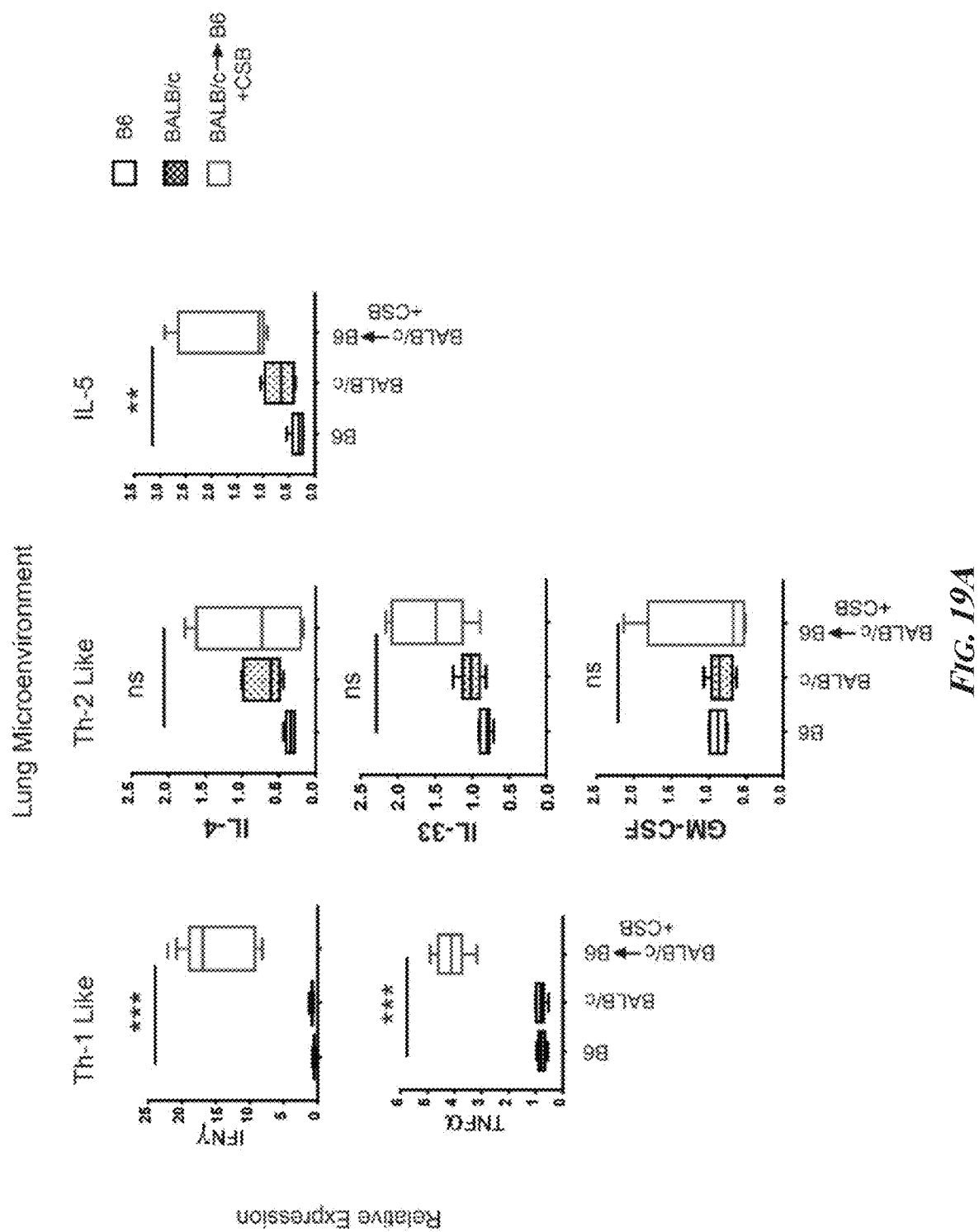
FIGS. 19A and 19B: Lung Allograft Acceptance is Associated with Th1 like Polarization.

The cytokine profiles of lungs from resting Balb/c, B6, as well as CSB-treated Balb/c to B6 lung allografts four days post-engraftment were determined. A significant increase in Th-1 like cytokines such as IFN-γ and TNF-α as well as the eosinophil survival factor IL-5 in accepting lungs was observed. Th2-specific cytokines such as IL-4, IL-33 and GM-CSF did not significantly increase post-transplantation (FIG. 19A).

Figure 19B:
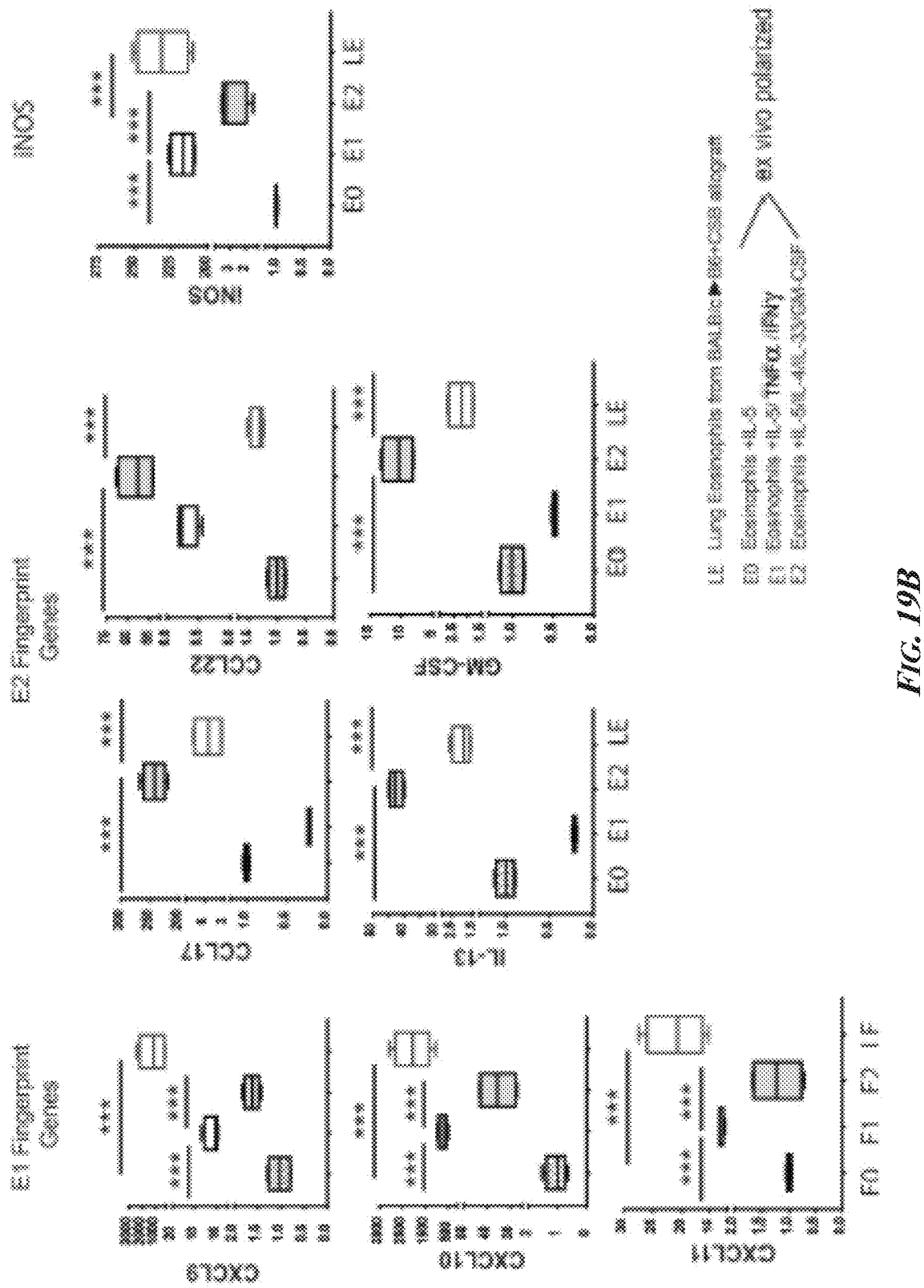

Next, graft-infiltrating eosinophils from CSB-treated Balb/c to B6 lungs were flow cytometrically sorted and their gene expression profiles were compared to peripheral blood-derived eosinophils polarized by overnight exposure to either a Th1 (IFN-γ and TNF-α), Th2 (IL-4, IL-33 and GM-CSF) or IL-5 alone (Th0) cytokine milieu, as described in Liu et al., 2007 and Jacobsen et al., 2015. The gene expression profile of lung graft-infiltrating eosinophils closely resembled the profile of eosinophils that were exposed to IFN-γ and TNF-α (designated as E1) with high levels of CXCL9, CXCL10 and CXCL11, and with lower levels of E2 signature genes such as CCL17, IL13, CCL22 and GM-CSF (FIG. 19B). Similar to eosinophils polarized toward an E1 phenotype ex vivo eosinophils isolated from accepting lung grafts expressed high levels of iNOS mRNA (FIG. 19B) consistent with their role as the dominant NO-producing cell after transplantation (as demonstrated in FIGS. 18B and 18C).

Figure 20:
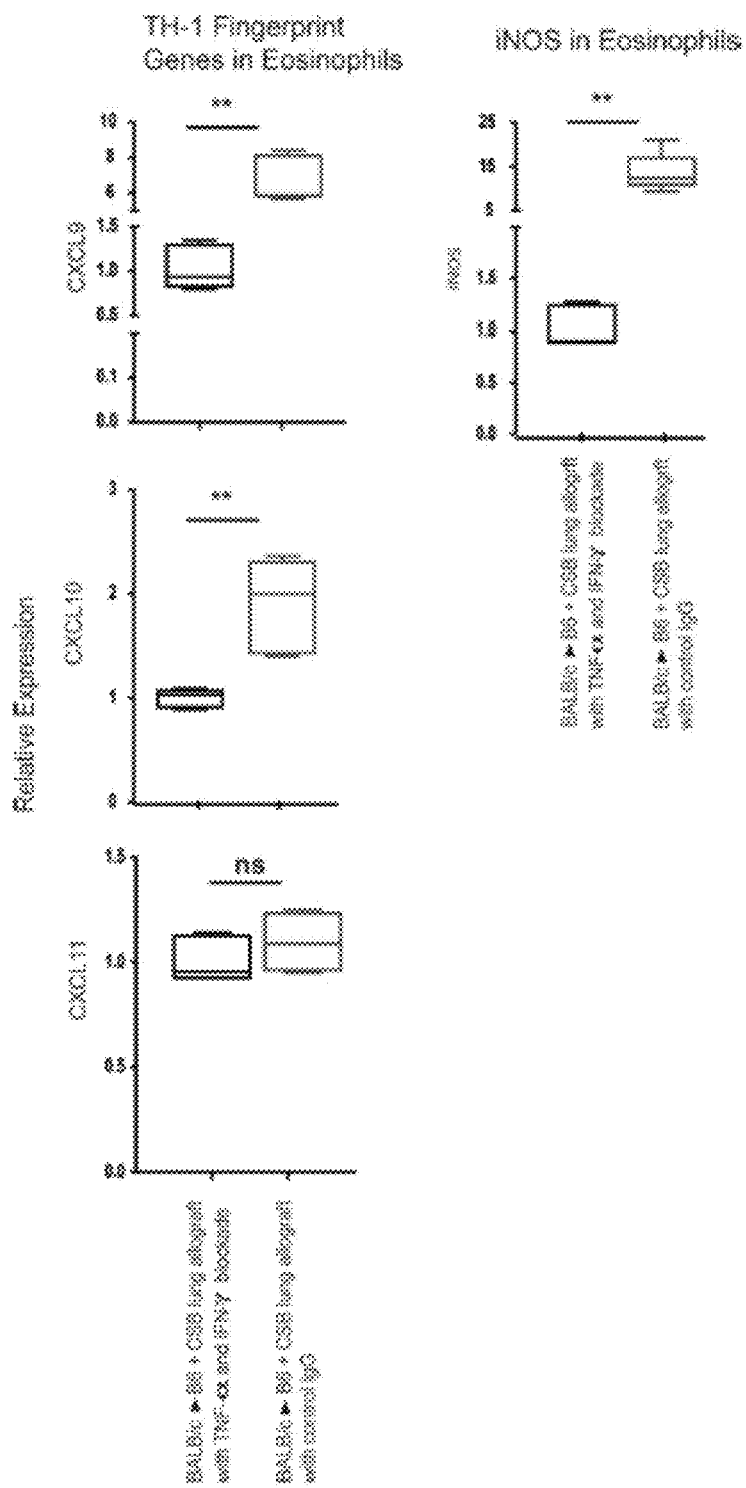
FIG. 20: Modulation of Th1 signature genes Expression in lung graft eosinophils. Expression of Th1 signature genes in lung graft eosinophils after IFN-γ and TNF-α blockade. Blue boxes represent eosinophils isolated from Balb/c to B6 transplanted lung grafts with CSB and black boxes represent eosinophils isolated from Balb/c to B6 transplanted lung grafts with CSB in the presence of IFN-γ and TNF-α neutralization (ns=p>0.05, **=p<0.01). Representative of minimum of four transplants per group.

To further delineate whether Th-1 polarizing cytokines contribute to iNOS production in eosinophils, this cell population from graft recipients where IFN-γ and TNF-α were neutralized by antibody blockade was immunophenotyped. Lung graft resident eosinophils from IFN-γ and TNF-α were neutralized produced less iNOS and expressed lower levels of Th-1 like transcripts compared to IgG-treated control mice (FIG. 20). Furthermore, it has previously been described that such Th1 cytokine neutralization results in graft rejection despite immunosuppression (Krupnick et al., 2014). Thus, these results further strengthened the conclusion that E1-polarization contributes to iNOS upregulation in eosinophils and is thus responsible for downregulating alloreactivity in the lung allograft.

Example 11

Figure 21A:
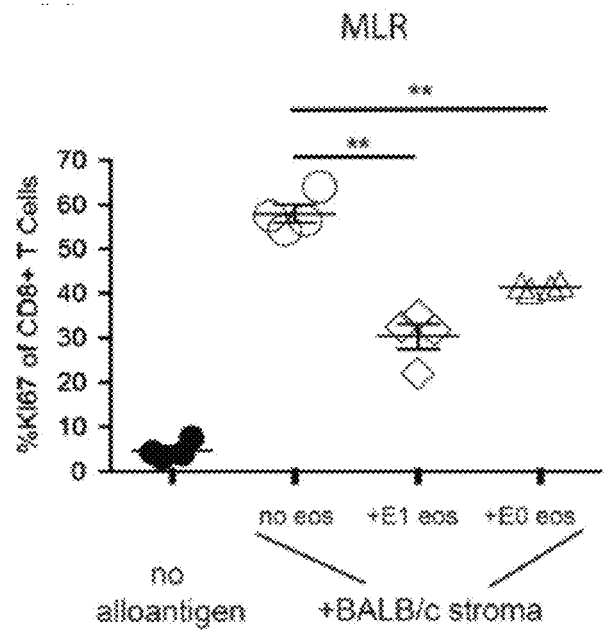
FIGS. 21A-21E: Modulation of CD8$^+$ T Cell Proliferation and Differentiation by E1 Polarized Eosinophil.
Figure 21B:
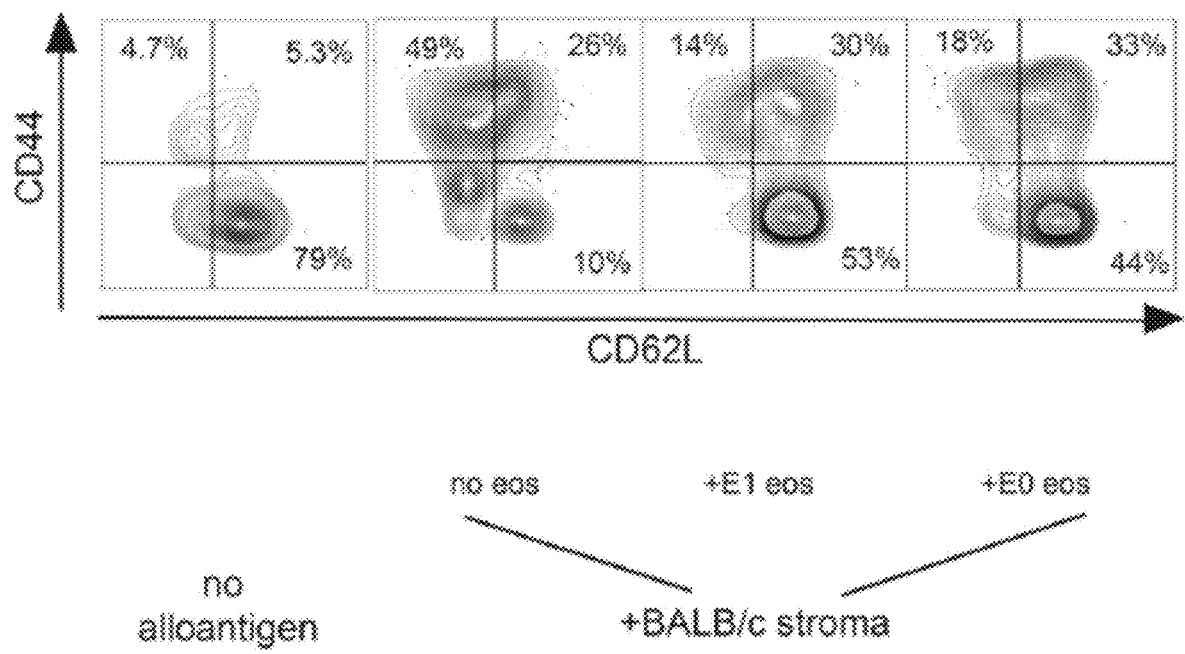

E1 Polarization of Eosinophils Contributes to the Downregulation of Alloreactivity To evaluate this assumption in a more stringent fashion, a reductionist approach, relying on mixed lymphocyte reactions (MLRs) of alloreactive T cell activation, was employed. Eosinophils from peripheral blood of mice were purified, which were of the E0 phenotype (Jacobsen et al., 2015), and polarized them toward an E1 phenotype by overnight exposure to IFN-γ, TNF-α and IL-5 or left them in the resting E0 state by exposure to IL-5 alone. Such eosinophils were then added as regulators to MLRs consisting of Balb/c$^{CD45.2+}$ splenocyte stimulators and B6$^{CD45.1+}$ congenic CD8$^+$ T cell responders. T lymphocyte responder proliferation was measured by Ki67 expression and their activation was evaluated by surface expression of CD44 and CD62L. While resting T cells showed minimal proliferation and maintained mostly a naïve CD62L$^{hi}$CD44$^{low}$ phenotype, exposure to Balb/c allogenic antigen-presenting cells resulted in Ki67 upregulation in the majority of the cells and activation to the CD62L$^{low}$CD44 effector phenotype in a large portion of CD8$^+$ T cells (FIGS. 21A and 21B). Addition of E1 polarized eosinophils as regulators to the MLR significantly inhibited CD8$^+$ T cell proliferation and differentiation.

Figure 21C:
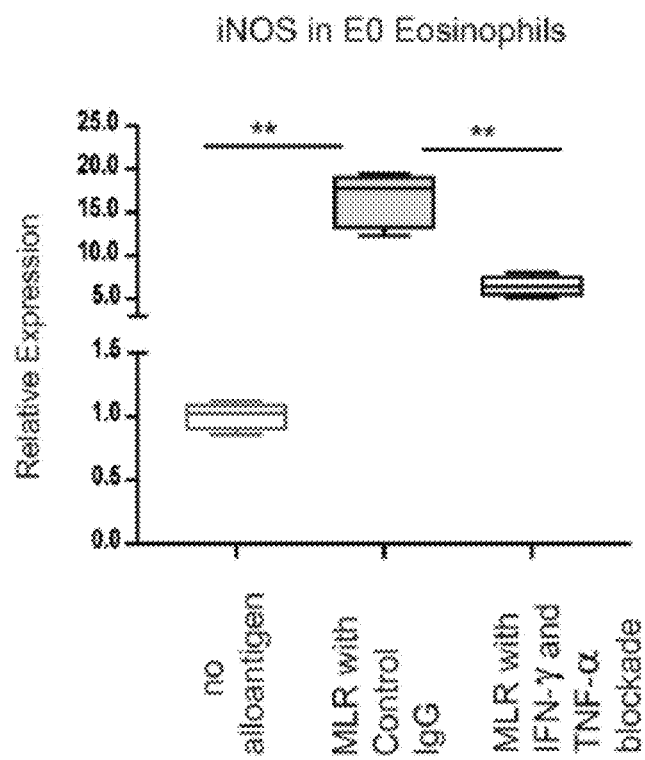
Figure 21D:
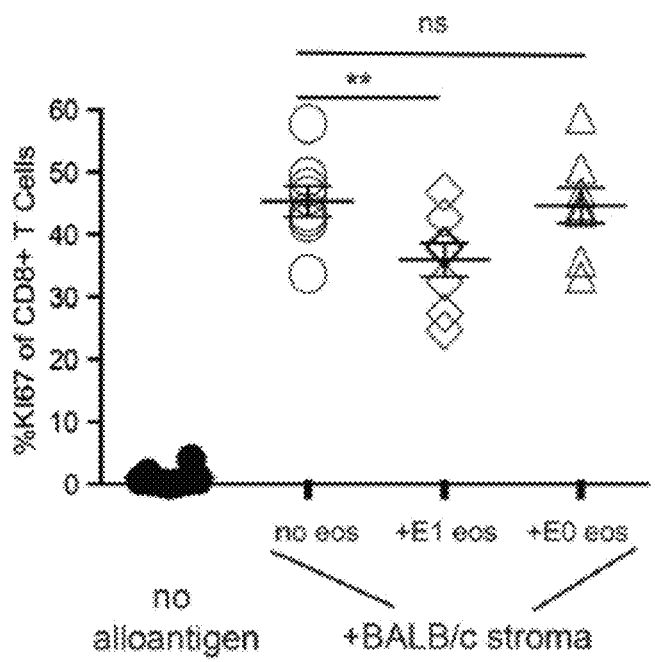
Figure 21E:
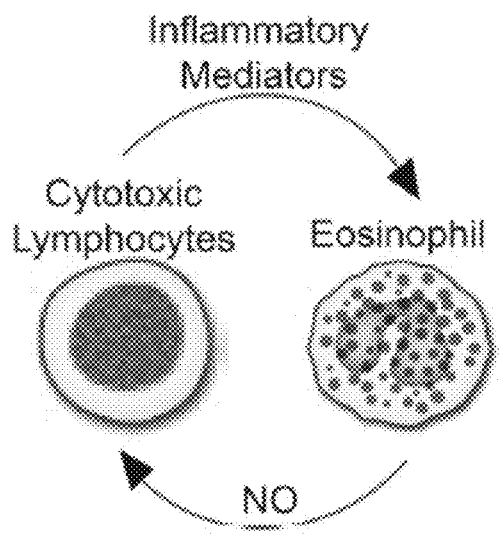

Surprisingly, E0 eosinophils also suppressed the alloimmune response, albeit at a slightly lower rate than E1 (FIG. 21A). This was somewhat perplexing as it has been demonstrated that NO elaboration directly influences downregulation of alloreactivity (Krupnick et al., 2014) and E0 eosinophils express very low levels of iNOS (FIG. 19B). The possibility that Th1 cytokines produced during the mixed lymphocyte reactions might alter the polarization of resting eosinophils and upregulate iNOS was thus tested. To this end, iNOS levels in E0 eosinophils prior to, as well as after, their addition to MLRs were determined. Indeed, eosinophils upregulated iNOS after co-culture with T cells, suggestive of E1 polarization during the MLR. Similar to in vivo studies described above such polarization was inhibited by IFN-γ and TNF-α blockade (FIG. 21C). Consistent with this data, IFN-γ and TNF-α neutralization during the mixed lymphocyte reaction abrogated the suppressive capacity of E0 eosinophils, while eosinophils polarized towards the E1 phenotype prior to the mixed lymphocyte reaction maintained their capacity to suppress CD8$^+$ T cell proliferation (FIG. 21D). Taken together, these data supported the conclusion that a feed-back loop existed between the inflammatory mediators that were produced within the allograft early after implantation, and downregulation of alloreactivity through the tolerogenic polarization of graft-resident eosinophils (FIG. 21E).

Discussion of the Examples

Unlike other solid organ allografts lungs are unique as they are continuously exposed to the external environment as part of their natural function of gas exchange. For these reasons unique pulmonary-specific immunoregulatory pathways have developed to eliminate environmental pathogens while resolving benign non-pathogenic insults. Pathways for rapid downregulation of inflammatory responses have also evolved out of necessity to ameliorate undue damage to bystander pulmonary parenchyma during the course of the immune response.

Eosinophils are bone-marrow derived granulocytes that are known for their ability to combat infection and are found in low levels at baseline in healthy lungs (Mesnil et al., 2016). Both experimental and clinical eosinophil deficiency renders hosts more susceptible to infectious disease, especially by fungal and parasitic organisms (Hagan et al., 1985; Hagan et al., 1985). Consistent with these IL-4 dominated parasitic Th2 responses, eosinophils have also been well-described to contribute to the initiation, propagation, and possibly resolution of allergic environmental asthma (Jacobsen et al., 2014b). While the role of eosinophils in other immunologic processes is still under investigation, disclosed herein is the determination that in the setting of lung transplantation, eosinophils function similarly to that of granulocytic myeloid derived suppressor cells by downregulating T cell immune responses through modification of TCR/CD3 stability and signal transduction (Nagaraj et al., 2007; Nagaraj et al., 2010).

Current clinical status of solid organ transplantation involves the use of global immunodepleting or immunosuppressive drugs. Standard protocols for surveillance have been designed to diagnose inflammatory changes through routinely scheduled biopsies of grafts (Balsara et al., 2018). Any increase in inflammation is treated through upregulation of immunosuppression to combat what is considered early rejection (Balsara et al., 2018). For these reasons eosinophil-related inflammatory changes and organ infiltration have been proposed as both a mediator and diagnostic feature of liver allograft rejection (Nagral et al., 1998). In direct contrast to this notion, disclosed herein is evidence that proinflammatory feedback loops, of which eosinophils are a critical component, play a critical role in tolerance induction in the lung (Onyema et al., 2017). Disruption of such loops, through depletion of either CD8$^+$ T cells or eosinophils, prevents co-stimulatory blockade mediated graft acceptance (Krupnick et al., 2014; Onyema et al., 2017). Those findings are extended herein by showing that eosinophils contribute to the downregulation of lung allograft rejection even in the absence of immunosuppression. The data presented herein thus solidifies the role of eosinophils as an exclusive and previously unrecognized regulatory leukocyte in the lung. Based on these data as well as select human observational studies, it is possible that they might play a similar immunosuppressive role in other organ transplants (Arbon et al., 2015). Furthermore, a recent report demonstrated that eosinophils may interfere with Th-1 mediated clearance of gastrointestinal pathogens (Arnold et al., 2018). It is thus possible that eosinophils might downregulate immune responses across multiple disease processes.

It is also disclosed herein that eosinophils interfere with TCR stability and signal transduction as their mechanism of immunosuppression. In this manner, eosinophil-mediated immunoregulation in the lung allograft mirrors that of malignancy-related immunosuppression, where multiple mechanisms function to downregulate TCR signaling and mediate tumor escape (Nagaraj et al., 2007; Nagaraj et al., 2010). This finding also creates an appealing aspect for tolerance induction as eosinophils can effectively alter the "priming" phase of alloreactivity that occurs immediately after engraftment. Since eosinophils accumulate in the allograft early after engraftment (Onyema et al., 2017), they affect allorecognition at early time points and may alter the frequency of alloreactive T cell clones for the life of the graft. By interfering with the strength of TCR signal transduction eosinophil-mediated downregulation of immune responses might mirror co-stimulatory blockade shaping of the T cell repertoire toward lower affinity clones (Miller et al., 2018). It is thus possible that such early action might indirectly affect long-term immunologic graft survival. That eosinophils might be critical at later time points in the lung remains possible.

Despite the ever-growing appreciation of inhibitory ligand receptor interactions in cancer (Pardoll, 2012), the biologic role of PD-L1 in transplant tolerance is just now being appreciated. The data presented herein support previous reports demonstrating that PD-L1 expression plays a role in tolerance induction of cardiac allografts (Pardoll, 2012). Another recent report showing that PD-1 blockade can break lung allograft tolerance supports this notion as well (Takahashi et al., 2018). Interestingly, disclosed here in evidence that PD-1/PD-L interactions increase the number of T cell-eosinophil contacts (FIG. 5E). This is in direct contrast to the case for CD11c DCs where PD-L1/PD-1 interactions actually decreased T cell dwell time (Takahashi et al., 2018). Taken together, it appears that T cell PD-1 expression might play a dual role in facilitating lung allograft tolerance by both decreasing interaction with pro-rejection APCs such as CD11c$^+$ dendritic cells while at the same time augmenting contact with regulatory cells such as eosinophils.

Since iNOS$^{-/-}$ eosinophils still expressed PD-L1 upon E0 to E1 polarization (FIG. 12A) it appears that, at least in the model disclosed herein, eosinophils expression of PD-L1 contributes to cell-cell interactions and not to direct inhibition of T cell activation through PD-1 engagement. This finding sets PD-L1 dependent allograft tolerance apart from some models of tumor-related immunosuppression, where direct signaling through PD-1 leads to downregulation of the T cell responses (Patsoukis et al., 2012). However, that data disclosed herein support other models where PD-L expression correlates with, but does not directly contribute to the downregulation of T cell function through PD-1 engagement (Goldman et al., 2018). Thus, the data presented herein extends the notion that the role of PD-L1 in immune suppression must be antigen presenting cell and context dependent.

While PD-L1/PD-1 seems to control cell contact, the presently disclosed data further support the dominant and near exclusive role of iNOS in eosinophil-mediated downregulation of immune responses. The observation that both contact and iNOS expression determines eosinophil-specific inhibition of T cell proliferation (FIG. 3B) further strengthens the notion that environmental polarization of eosinophils is critical for their suppressive function. It is important to point out that in the absence of exogenous Th-1 polarizing cytokines, such as IFN-γ and TNF-α, neither PD-L1 or iNOS are expressed in E0 unpolarized resting eosinophils (FIGS. 1A, 1B, and 12A). Only upon polarization to the E1 phenotype do such suppressive mediators become evident (FIG. 12A). IL-4 and IL-33 polarized E2 eosinophils also do not express iNOS (FIGS. 1A and 1B) furthering the notion that the environmental context controls eosinophil-mediated immunoregulation in our system.

Unlike the case for most other organs, where access for local drug delivery can be problematic, intratracheal administration of biologic mediators can readily be utilized to alter the course of pulmonary immune responses (Deuse et al., 2010; Groves et al., 2010). Based on this notion, disclosed herein is evidence showing that local administration of eosinophil-specific chemokines and cytokines can alter lung allograft rejection in an eosinophil-dependent fashion. Such data open the possibility of accentuating naturally occurring tolerogenic feedback loops in order to downregulate lung graft rejection in the absence of global non-specific immunosuppression.

Lungs allografts have worse long-term survival compared to other organ transplants. This is most likely due to their unique immunoregulation that may not respond to traditional immunosuppression. For example, local nitric oxide (NO) generation by inducible nitric oxide synthase (iNOS) is critical for lung allograft acceptance but associates with rejection of other solid organs. The source of NO in accepting lung allografts remains unknown. Here we report that, unlike the case for other pulmonary processes where myeloid cells control NO generation, recipient-derived eosinophils play a critical and non-redundant role in iNOS-mediated lung allograft acceptance. Depletion of eosinophils reduces NO levels to that of recipients with global deletion of iNOS and leads to a co-stimulatory blockade resistant form of rejection. Furthermore, NO production by eosinophils depends on Th1 polarization by inflammatory mediators such as IFN-γ and TNF-α. Neutralization of such mediators abrogates eosinophil suppressive capacity. Our data points to a unique and previously unrecognized role of eosinophil polarization in mediating allograft tolerance and puts into perspective the use of high-dose eosinophil ablating corticosteroids post lung transplantation.

The lung allograft is unique in its immune response after transplantation. For example, while the local production of nitric oxide (NO) correlates with rejection of kidney (Vos et al., 2000) and heart allografts (Szabolcs et al., 2001), it has demonstrated that NO plays a critical role in amelioration of lung allograft pathology (Krupnick et al., 2014). Specifically the expression of recipient-derived type II nitric oxide synthase, or inducible nitric oxide synthase (iNOS), is a critical factor for co-stimulatory blockade (CSB)-mediated lung allograft acceptance (Krupnick et al., 2014). Myeloid cells have the capacity to express iNOS and were thus suspect as contributing to iNOS-mediated lung allograft acceptance (Chong et al., 2011).

Described herein is the surprising observation that acceptance of allogeneic lung allografts depends on the transient presence of recipient-derived iNOS; eosinophils. The generation of iNOS$^+$ eosinophils is facilitated by cytokine patterns that are expressed locally within the lung during tolerance induction. Thus, an unrecognized role for eosinophils as a mechanistic link between inflammation associated with early graft responses and tolerance is described herein. The presently disclosed data further extend the notion that the immunologic environment associated with lung allograft acceptance is unique and challenges current immunosuppressive strategies for lung transplant recipients.

The role of eosinophils in health and disease is often summarized by pervasive consensus opinions that their activity is primarily destructive and cytocidal in nature (Watson et al., 1993). Thus, traditional therapeutic strategies have focused on the destruction of this cell population for modulation of inflammatory disease processes. However, the wealth of recently available studies investigating the role(s) of eosinophils in both health and disease demonstrate that the activities of these granulocytes are far more expansive than previously appreciated (Jacobsen et al., 2007; Wegmann, 2011; Jacobsen et al., 2012; Lee et al., 2012; Fulkerson & Rothenberg, 2013; Rosenberg et al., 2013; Jacobsen et al., 2014b). Masterson and colleagues recently demonstrated a protective role of eosinophils in downregulating colonic inflammation through the production of anti-inflammatory lipid mediators (Masterson et al., 2015) while Mesnil and colleagues identified a distinct regulatory eosinophil subset with key homeostatic function in the lung (Mesnil et al., 2016). It has been suggested that eosinophils are important regulators of local immunity and/or remodeling/repair in both health and disease: i.e., the LIAR Hypothesis (Lee et al., 2010). In this paradigm, eosinophils are neither singularly destructive nor penultimate regulatory. Instead, they mediate activities whose effects are wide in scope. Consistent with this notion, it has been demonstrated herein that eosinophils are previously unrecognized participants in the immune responses leading to allograft tolerance Since the lungs are continuously exposed to the external environment, mechanisms have developed to downregulate aberrant inflammation induced by inflammatory lymphocytes (Galli et al., 2008; Budden et al., 2017). Based on data presented herein and those described in previous experimental models, one can conclude that such negative feedback loops are critical for tolerance induction in lungs. This notion is supported by experimental models demonstrating that depletion of CD8$^+$ T cells, and neutralization of Th1-type cytokines, actually prevents rather than facilitates lung allograft tolerance (Kishimoto et al., 2002; Krupnick et al., 2014). Disclosed herein is the identification of the E1 polarized eosinophil as a critical mediator in the feedback loop downregulating graft-deleterious inflammatory responses.

Unlike the case for T lymphocytes and macrophages, the functional significance of environmental polarization of eosinophils is poorly described. The finding that the Th1 like pulmonary environment and E1 polarization of eosinophils plays a critical role in lung allograft tolerance is further surprising based on the association of Th2 polarization with CSB-induced tolerance in heart and kidney allografts (Takeuchi et al., 1992; Sayegh et al., 1995). Such differences further point to the unique immunologic environment of the lung. Nevertheless, the presently disclosed data help explain the critical role of undifferentiated CD44$^{high}$CCR7$^{high}$CD62L$^{high}$ central memory T cells in lung allograft tolerance (Krupnick et al., 2014). Unlike CD44$^{high}$CCR7$^{low}$CD62L$^{low}$ effector CD8$^+$ T cells, which are able to destroy cellular targets via direct cytotoxicity, central memory CD8$^+$ T cells elaborate pro-inflammatory cytokines but fail to mediate direct cytotoxicity. Thus, this cell population can initiate the tolerogenic eosinophil-iNOS-mediated feedback loop described above but is unable to directly destroy allogeneic grafts.

While limited data exist regarding nitric oxide production by eosinophils, this cell population has been demonstrated to contribute to asthma-related protein nitration (Iijima et al. (2001; MacPherson et al., 2001). Along those lines, the presently disclosed data demonstrate that the unique NO-dependence of the lung allograft for tolerance induction takes advantage of this iNOS-dependent aspect of eosinophil biology. It is important to point out that local NO production may be important during the initial phases of tolerance induction but may not be as critical for long-term maintenance. This is evidenced by the gradual reduction of iNOS-expressing cells in the accepted graft (FIG. 15C) despite the fact that local immunoregulatory circuits facilitate acceptance upon retransplantation into a secondary, non-immunosuppressed host (Li et al., 2012). It is possible that eosinophil-dependent NO production is important in the early peri-operative period while other suppressive cell population, such as regulatory T cells, contribute to maintenance of tolerance. Nevertheless, the presently disclosed data strongly suggest that clinical interventions targeting all alloreactive cytotoxic lymphocytes or eosinophils, such as through the use of high dose corticosteroids, may have unpredictable and hidden deleterious effects for the lung allograft's long-term survival.

Summarily, despite the accepted notion that granulocytes play a universally destructive role in organ and tissue grafts, it has been recently described that eosinophils can facilitate immunosuppression-mediated acceptance of murine lung allografts. The mechanism of eosinophil-mediated tolerance, or their role in regulating alloimmune responses in the absence of immunosuppression, remains unknown. Using lung transplants in a fully MHC-mismatched Balb/c (H2d) to C57BL/6 (H2b) strain combination it is disclosed herein that eosinophils downregulate T cell-mediated immune responses and play a tolerogenic role even in the absence of immunosuppression. It is further shown that such downregulation depends on PD-L1/PD-1-mediated synapse formation between eosinophils and T cells. Additionally, the presently disclosed subject matter demonstrates that eosinophils suppress T lymphocyte responses through the inhibition of TCR/CD3 subunit association and signal transduction in an inducible nitric oxide synthase-dependent manner. Increasing local eosinophil concentration, through administration of intratracheal eotaxin and/or IL-5, can thus ameliorate alloimmune responses in the lung allograft. As such, the data provided herein indicate that eosinophil mobilization can be employed as a method for inducing lung allograft specific immunosuppression.

REFERENCES

All references listed in the instant disclosure, including but not limited to all patents, patent applications and publications thereof, scientific journal articles, and database entries (including but not limited to GENBANK® biosequence database entries and all citation and annotations presented therein) are incorporated herein by reference in their entireties to the extent that they supplement, explain, provide a background for, and/or teach methodology, techniques, and/or compositions employed herein.

Abdala-Valencia et al. (2018) Shaping eosinophil identity in the tissue contexts of development, homeostasis, and disease. J Leukoc Biol. 104(1):95-108.

Altschul et al. (1990a) Basic local alignment search tool. J Mol Biol 215(3):403-10.

Altschul et al. (1990b) Protein database searches for multiple alignments. Proc Natl Acad Sci USA. 87(14):5509-13.

Altschul et al. (1997) Gapped BLAST and PSI-BLAST: a new generation of protein database search programs. Nucleic Acids Res. 25(17):3389-402.

Arbon et al. (2015) Eosinophil count, allergies, and rejection in pediatric heart transplant
recipients. J Heart Lung Transplant. 34(8):1103-11.

Arnold et al. (2018) Eosinophils suppress Th1 responses and restrict bacterially induced gastrointestinal inflammation. J Exp Med. 215(8):2055-72.

Ashouri & Weiss (2017) Endogenous Nur77 Is a Specific Indicator of Antigen Receptor Signaling in Human T and B Cells. J Immunol. 198(2):657-68.

Ausubel et al. (1992) Current Protocols in Molecular Biology, John Wiley & Sons, New York, New York Balsara et al. (2018) A single-center experience of 1500 lung transplant patients. J Thorac Cardiovasc Surg. 156(2): 894-905 e3.

Bolger et al. (2014) Trimmomatic: A flexible trimmer for Illumina Sequence Data.
Bioinformatics 30:2114-2120.

Bradshaw et al. (2017) Reliable CD4 and CD8 T Cell Marker Immunohistochemistry on Formalin-Fixed and Histochoice-Fixed Paraffin Embedded Mouse Spleen. The FASEB Journal. 31(1_supplement):979.5-.5.

Budden et al. (2017) Emerging pathogenic links between microbiota and the gut-lung axis. Nat Rev Microbiol. 15(1):55-63.

Carr et al. (2016) Eosinophilic bioactivities in severe asthma. World Allergy Organ J. 9:21.

Chen et al. (2013) Increased T cell glucose uptake reflects acute rejection in lung grafts. Am J Transplant. 13(10): 2540-9.

Chong et al. (2011). Human CD8(+) T cells drive Th1 responses through the differentiation of TNF/iNOS-producing dendritic cells. European journal of immunology. 41(6): 1639-51.

Conde et al. (2015) DC-SIGN(+) Macrophages Control the Induction of Transplantation Tolerance. Immunity. 42(6): 1143-58.

Deuse et al. (2010) Mechanisms behind local immunosuppression using inhaled tacrolimus in preclinical models of lung transplantation. Am J Respir Cell Mol Biol. 43(4): 403-12.

Devereux et al. (1984) A comprehensive set of sequence analysis programs for the VAX. Nucleic Acids Res 12(1 Pt 1):387-95.

Drake et al. (2016) Human and Mouse Eosinophils Have Antiviral Activity against Parainfluenza Virus. Am J Respir Cell Mol Biol. 55(3):387-94.

Fonseca et al. (2003) TNF-alpha mediates the induction of nitric oxide synthase in macrophages but not in neutrophils in experimental cutaneous leishmaniasis. European journal of immunology. 33(8):2297-306.

Fulkerson & Rothenberg (2013) Targeting eosinophils in allergy, inflammation and beyond. Nat Rev Drug Discov. 12(2): 117-29.

Galli et al. (2008) The development of allergic inflammation. Nature. 454(7203):445-54.

Garcia et al. (2010) Monocytic suppressive cells mediate cardiovascular transplantation tolerance in mice. The Journal of Clinical I. 120(7):2486-96.

Gelman et al. (2008) CD4$^+$ T lymphocytes are not necessary for the acute rejection of vascularized mouse lung transplants. Journal of immunology. 180(7):4754-62.

Gelman et al. (2009) Cutting edge: Acute lung allograft rejection is independent of secondary lymphoid organs. J Immunol. 182(7):3969-73.

Genaro (ed.) (1985) *Remington's Pharmaceutical Sciences*. 17$^{th}$ Edition, Mack Publishing Co., Easton, Pennsylvania Goldman et al. (2001) A role for eosinophils in transplant rejection. Trends Immunol. 22(5):247-51.

Goldman et al. (2018) High macrophage PD-L1 expression not responsible for T cell suppression. Cell Immunol. 324:50-8.

Griseri et al. (2015) Granulocyte Macrophage Colony-Stimulating Factor-Activated Eosinophils Promote Interleukin-23 Driven Chronic Colitis. Immunity. 43(1):187-99.

Groves et al. (2010) Inhaled cyclosporine and pulmonary function in lung transplant recipients. J Aerosol Med Pulm Drug Deliv. 23(1):31-9.

Hagan et al. (1985) Eosinophilia and resistance to *Schistosoma haematobium* in man. Parasite Immunol. 7(6):625-32.

Helft et al. (2015) GM-CSF Mouse Bone Marrow Cultures Comprise a Heterogeneous Population of CD11c(+) MHCII(+) Macrophages and Dendritic Cells. Immunity. 42(6):1197-211.

Henikoff & Henikoff (1992) Amino acid substitution matrices from protein blocks. Proc Natl Acad Sci USA 89:10915-10919.

Iijima et al. (2001) Nitric oxide and protein nitration are eosinophil dependent in allergen-challenged mice. Am J Respir Crit Care Med. 163(5): 1233-40.

Jacobsen et al. (2007) Eosinophils: singularly destructive effector cells or purveyors of immunoregulation? J Allergy Clin Immunol. 119(6):1313-20.

Jacobsen et al. (2008) Allergic pulmonary inflammation in mice is dependent on eosinophil-induced recruitment of effector T cells. J Exp Med. 205(3):699-710.

Jacobsen et al. (2011) Eosinophils regulate dendritic cells and Th2 pulmonary immune responses following allergen provocation. J Immunol. 187(11):6059-68.

Jacobsen et al. (2012) The expanding role(s) of eosinophils in health and disease. Blood. 120(19):3882-90.

Jacobsen et al. (2014a) Eosinophil activities modulate the immune/inflammatory character of allergic respiratory responses in mice. Allergy. 69(3):315-27.

Jacobsen et al. (2014b) Re-defining the unique roles for eosinophils in allergic respiratory inflammation. Clin Exp Allergy. 44(9): 1119-36.

Jacobsen et al. (2015) Differential activation of airway eosinophils induces IL-13-mediated allergic Th2 pulmonary responses in mice. Allergy. 70(9): 1148-59.

Jacobsen et al. (2017) Lung Pathologies in a Chronic Inflammation Mouse Model Are Independent of Eosinophil Degranulation. American journal of respiratory and critical care medicine. 195(10):1321-32.

Karlin & Altschul (1993) Applications and statistics for multiple high-scoring segments in molecular sequences. Proc Natl Acad Sci USA 90:5873-5877.

Kato & Nariuchi (2000) Polarization of naive CD4$^+$ T cells toward the Th1 subset by CTLA-4 costimulation. J Immunol. 164(7):3554-62.

Kishimoto et al. (2002) Th cytokines, programmed cell death, and alloreactive T cell clone size in transplant tolerance. The Journal of clinical investigation. 109(11): 1471-9.

Knoop et al. (2004) Immunosuppressive therapy after human lung transplantation. Eur Respir J. 23(1):159-71.

Kreisel et al. (2011) Emergency granulopoiesis promotes neutrophil-dendritic cell encounters that prevent mouse lung allograft acceptance. Blood. 118(23):6172-82.

Krupnick et al. (2009) Orthotopic mouse lung transplantation as experimental methodology to study transplant and tumor biology. Nat Protoc. 4(1):86-93.

Krupnick et al. (2014) Central memory CD8+ T lymphocytes mediate lung allograft acceptance. J Clin Invest. 124(3): 1130-43.

Kulkarni et al. (2019) Bronchiolitis obliterans syndrome-free survival after lung transplantation: An International Society for Heart and Lung Transplantation Thoracic Transplant Registry analysis. J Heart Lung Transplant. 38(1):5-16.

Larsen et al. (1996) Long-term acceptance of skin and cardiac allografts after blocking CD40 and CD28 pathways. Nature. 381(6581):434-8.

Lee et al. (1997) Expression of IL-5 in thymocytes/T cells leads to the development of a massive eosinophilia, extramedullary eosinophilopoiesis, and unique histopathologies. J Immunol. 158(3):1332-44.

Lee et al. (2010) Eosinophils in health and disease: the LIAR hypothesis. Clin Exp Allergy. 40(4):563-75.

Lee et al. (2012) Human versus mouse eosinophils: "that which we call an eosinophil, by any other name would stain as red". J Allergy Clin Immunol. 130(3):572-84.

Li & Shi (2015) Tolerogenic dendritic cells and their applications in transplantation. Cell Mol Immunol. 12(1):24-30.

Li et al. (2012) Lung transplant acceptance is facilitated by early events in the graft and is associated with lymphoid neogenesis. Mucosal Immunol. 5(5):544-54.

Lilly et al. (2014) Eosinophil deficiency compromises lung defense against *Aspergillus fumigatus*. Infect Immun. 82(3):1315-25.

Liu et al. (2007) Generation of Th1 and Th2 chemokines by human eosinophils: evidence for a critical role of TNF-alpha. Journal of Immunology. 179(7):4840-8.

Lotfi & Lotze (2008) Eosinophils induce DC maturation, regulating immunity. J Leukoc Biol. 83(3):456-60.

MacPherson et al. (2001) Eosinophils are a major source of nitric oxide-derived oxidants in severe asthma: characterization of pathways available to eosinophils for generating reactive nitrogen species. Journal of Immunology. 166(9):5763-72.

Markey et al. (2014) Cross-dressing by donor dendritic cells after allogeneic bone marrow transplantation contributes to formation of the immunological synapse and maximizes responses to indirectly presented antigen. J Immunol. 192(11):5426-33.

Martinez et al. (1993) Evidence for a nonclassical pathway of graft rejection involving interleukin 5 and eosinophils. Transplantation. 55(4):909-18.

Masterson et al. (2015) Eosinophil-mediated signalling attenuates inflammatory responses in experimental colitis. Gut. 64(8):1236-47.

Mesnil et al. (2016) Lung-resident eosinophils represent a distinct regulatory eosinophil subset. J Clin Invest. 126 (9):3279-95.

Miller et al. (2018) Distinct Graft-Specific TCR Avidity Profiles during Acute Rejection and Tolerance. Cell Rep. 24(8):2112-26.

Moran et al. (2011) T cell receptor signal strength in Treg and iNKT cell development demonstrated by a novel fluorescent reporter mouse. J Exp Med. 208(6): 1279-89.

Morikawa et al. (2000) Augmentation of nitric oxide production by gamma interferon in a mouse vascular endothelial cell line and its modulation by tumor necrosis factor alpha and lipopolysaccharide. Infect Immun. 68(11):6209-14.

Murphy (1999) Nitric oxide and cell death. Biochim Biophys Acta. 1411(2-3):401-14.

Nagral et al. (1998) Eosinophils in acute cellular rejection in liver allografts. Liver Transpl Surg. 1998; 4(5):355-62.

Nair et al. (2009) Mepolizumab for prednisone-dependent asthma with sputum eosinophilia. The New England Journal of Medicine. 360(10):985-93.

Nagaraj et al. (2007) Altered recognition of antigen is a mechanism of CD8+ T cell tolerance in cancer. Nat Med. 13(7):828-35.

Nagaraj et al. (2010) Mechanism of T cell tolerance induced by myeloid-derived suppressor cells. J Immunol. 184(6): 3106-16.

Nagral et al. (1998) Eosinophils in acute cellular rejection in liver allografts. Liver Transpl Surg. 4(5):355-62.

Needleman & Wunsch (1970) A general method applicable to the search for similarities in the amino acid sequence of two proteins. J Mol Biol 48:443-453.

Okazaki et al. (2007) A mouse model of orthotopic vascularized aerated lung transplantation. Am J Transplant. 7(6):1672-9.

Onyema et al. (2017) Eosinophils promote inducible NOS-mediated lung allograft acceptance. JCI Insight. 2(24).

Paoliello-Paschoalato et al. (2005) Interleukin 4 induces the expression of inducible nitric oxide synthase in eosinophils. Cytokine. 30(3):116-24.

Pardoll (2012) The blockade of immune checkpoints in cancer immunotherapy. Nat Rev Cancer. 12(4):252-64.

Patsoukis et al. (2012) Selective effects of PD-1 on Akt and Ras pathways regulate molecular components of the cell cycle and inhibit T cell proliferation. Sci Signal. 5(230): ra46.

Pearson & Lipman (1988) Improved tools for biological sequence comparison. Proc Natl Acad Sci USA 85(8): 2444-2448.

Percopo et al. (2017) SiglecF+Gr1$^{hi}$ eosinophils are a distinct subpopulation within the lungs of allergen-challenged mice. J Leukoc Biol. 101:321-328.

Pillay et al. (2012) A subset of neutrophils in human systemic inflammation inhibits T cell responses through Mac-1. J Clin Invest. 122(1):327-36.

Rankin et al. (2000) Eotaxin and eosinophil recruitment: implications for human disease. Mol Med Today. 6(1): 20-7.

Rosenberg et al. (2013) Eosinophils: changing perspectives in health and disease. Nat Rev Immunol. 13(1):9-22.

Roufosse et al. (2013) Long-term safety of mepolizumab for the treatment of hypereosinophilic syndromes. J Allergy Clin Immunol. 131(2):461-7 e1-5.

Sayegh et al. (1995) CD28-B7 blockade after alloantigenic challenge in vivo inhibits Th1 cytokines but spares Th2. The Journal of Experimental Medicine. 181(5): 1869-74.

Schenk et al. (2008) Donor-reactive CD8 memory T cells infiltrate cardiac allografts within 24-h posttransplant in naive recipients. Am J Transplant. 8(8): 1652-61.

Schouppe et al. (2013) Modulation of CD8(+) T-cell activation events by monocytic and granulocytic myeloid-derived suppressor cells. Immunobiology. 218(11): 1385-91.

Schrum et al. (2007) High-sensitivity detection and quantitative analysis of native protein-protein interactions and multiprotein complexes by flow cytometry. Sci STKE. 2007(389):pl2.

Sharpe (2009) Mechanisms of costimulation. Immunol Rev. 229(1):5-11.

Shen & Malter (2015) Determinants of eosinophil survival and apoptotic cell death. Apoptosis. 20(2):224-34.

Smith & Waterman (1981) Comparative biosequence metrics. J Mol Evol 18(1):38-46.

Szabolcs et al. (2001) Acute cardiac allograft rejection in nitric oxide synthase-2(−/−) and nitric oxide synthase-2 (+/+) mice: effects of cellular chimeras on myocardial inflammation and cardiomyocyte damage and apoptosis. Circulation. 103(20):2514-20.

Takahashi et al. (2018) PD-1 expression on CD8(+) T cells regulates their differentiation within lung allografts and is critical for tolerance induction. Am J Transplant. 18(1): 216-25.

Takeuchi et al. (1992) Heart allografts in murine systems. The differential activation of Th2-like effector cells in peripheral tolerance. Transplantation. 53(6):1281-94.

Tanaka et al. (2007) PDL 1 is required for peripheral transplantation tolerance and protection from chronic allograft rejection. J Immunol. 179(8):5204-10.

U.S. Patent Application Publication No. 2017/0114411.

U.S. Pat. Nos. 8,247,175; 8,637,232; 10,000,809.

Veres et al. (2017) Allergen-Induced CD4+ T Cell Cytokine Production within Airway Mucosal Dendritic Cell-T Cell Clusters Drives the Local Recruitment of Myeloid Effector Cells. J Immunol. 198(2):895-907.

Vos et al. (2000) Inhibition of inducible nitric oxide synthase improves graft function and reduces tubulointerstitial injury in renal allograft rejection. Eur J Pharmacol. 391 (1-2):31-8.

Wabnitz et al. (2011) L-plastin phosphorylation: a novel target for the immunosuppressive drug dexamethasone in primary human T cells. Eur J Immunol. 41(11):3157-69.

Watson et al. (1993) Cytokines contribute to airway dysfunction in antigen-challenged guinea pigs: inhibition of airway hyperreactivity, pulmonary eosinophil accumulation, and tumor necrosis factor generation by pretreatment with an interleukin-1 receptor antagonist. Am J Respir Cell Mol Biol. (4):365-9.

Wegmann (2011) Targeting eosinophil biology in asthma therapy. Am J Respir Cell Mol Biol. 45(4):667-74.

Witt et al. (2014) Lung transplant immunosuppression— time for a new approach? Expert Rev Clin Immunol. 10(11):1419-21.

Yang et al. (1997) Depletion of eosinophil infiltration by anti-IL-5 monoclonal antibody (TRFK-5) accelerates open skin wound epithelial closure. Am J Pathol. 151(3): 813-9.

Yousem et al. (1996) Revision of the 1990 working formulation for the classification of pulmonary allograft rejection: Lung Rejection Study Group. J Heart Lung Transplant. 15(1 Pt 1):1-15.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for enhancing immunosuppression in the lung of a subject, the method comprising administering to the subject a composition comprising at least one eosinophil recruiting agent, wherein the administering is in an amount and via a route of administration sufficient to induce recruitment of eosinophils to the lung of the subject to thereby enhance immunosuppression in the lung of the subject, and further wherein the lung is a transplanted lung in the subject, the subject is an otherwise non-immunosuppressed subject, and the immunosuppression is sufficient to reduce rejection of the transplanted lung in the subject.

2. The method of claim 1, wherein the transplanted lung is allogeneic to the subject.

3. The method of claim 1, wherein the composition is formulated for administration by any one of intratracheal installation, insufflation, nebulization, dry powder inhalation, aerosol inhalation, and combinations thereof.

4. The method of claim 1, wherein the eosinophil recruiting agent is selected from the group consisting of an interleukin-5 (IL-5), an eotaxin, a platelet activating factor, an eicosanoid, or any combination thereof.

5. The method of claim 4, wherein the eosinophil recruiting agent comprises eotaxin-1 and/or eotaxin-2, and optionally further comprises IL-5.

6. A method for enhancing tolerance to a lung transplant in a subject, the method comprising administering to the subject a composition comprising at least one eosinophil recruiting agent, wherein the administering is in an amount and via a route of administration sufficient to induce recruitment of eosinophils to the lung of the subject to thereby enhance tolerance to the lung transplant in the subject, wherein the subject is an otherwise non-immunosuppressed subject.

7. The method of claim 6, wherein the at least one eosinophil recruiting agent is administered to the subject in one or more doses concurrently with and/or subsequent to the lung transplant being introduced into the subject.

8. The method of claim 6, wherein the lung transplant is allogenic to the subject.

9. A method for enhancing recruitment of eosinophils to a lung of a subject, the method comprising administering to the subject a composition comprising at least one eosinophil recruiting agent, wherein the administering enhances recruitment of eosinophils to the lung of the subject, and further wherein the lung is a transplanted lung and where the subject is an otherwise non-immunosuppressed subject.

10. A method for modulating a T cell-mediated immune response in a lung of a subject, the method comprising administering to the subject a composition comprising at least one eosinophil recruiting agent, wherein the administering enhances recruitment of eosinophils to the lung of the subject to thereby modulate the T cell-mediated immune response in the lung of the subject, and further wherein the lung is a transplanted lung and where the subject is an otherwise non-immunosuppressed subject.

11. A method for reducing T cell antigen receptor (TCR) signal transduction in a lung of a subject, the method comprising administering to the subject a composition comprising at least one eosinophil recruiting agent, wherein the administering enhances recruitment of eosinophils to the lung of the subject to thereby reduce TCR signal transduction in the lung of the subject, and further wherein the lung is a transplanted lung and where the subject is an otherwise non-immunosuppressed subject.

12. The method of claim 11, wherein the administering inhibits proliferation of CD8+ T cells in the lung of the subject.

13. The method of claim 12, wherein the administering enhances expression of an inducible nitric oxide synthase (iNOS) gene product in the lung of the subject to thereby reduce TCR signal transduction in the lung of the subject.

14. The method of claim 13, wherein the expression of the iNOS gene product is enhanced in an eosinophil present in the lung of the subject, optionally a Th1-polarized eosinophil present in the lung of the subject.

15. The method of claim 1, wherein the subject is a human.

* * * * *

SEQUENCE LISTING

```
<160> NUMBER OF SEQ ID NOS: 36

<210> SEQ ID NO 1
<211> LENGTH: 815
<212> TYPE: DNA
<213> ORGANISM: Homo sapiens
<220> FEATURE:
<221> NAME/KEY: CDS
<222> LOCATION: (45)..(449)

<400> SEQUENCE: 1
atgcactttc tttgccaaag gcaaacgcag aacgtttcag agcc atg agg atg ctt        56
                                              Met Arg Met Leu
                                                1 ctg cat ttg agt ttg cta gct ctt gga gct gcc tac gtg tat gcc atc       104
Leu His Leu Ser Leu Leu Ala Leu Gly Ala Ala Tyr Val Tyr Ala Ile
  5              10                  15                  20 ccc aca gaa att ccc aca agt gca ttg gtg aaa gag acc ttg gca ctg       152
Pro Thr Glu Ile Pro Thr Ser Ala Leu Val Lys Glu Thr Leu Ala Leu
              25                  30                  35 ctt tct act cat cga act ctg ctg ata gcc aat gag act ctg agg att       200
Leu Ser Thr His Arg Thr Leu Leu Ile Ala Asn Glu Thr Leu Arg Ile
          40                  45                  50 cct gtt cct gta cat aaa aat cac caa ctg tgc act gaa gaa atc ttt       248
Pro Val Pro Val His Lys Asn His Gln Leu Cys Thr Glu Glu Ile Phe
      55                  60                  65 cag gga ata ggc aca ctg gag agt caa act gtg caa ggg ggt act gtg       296
Gln Gly Ile Gly Thr Leu Glu Ser Gln Thr Val Gln Gly Gly Thr Val
  70                  75                  80 gaa aga cta ttc aaa aac ttg tcc tta ata aag aaa tac att gac ggc       344
Glu Arg Leu Phe Lys Asn Leu Ser Leu Ile Lys Lys Tyr Ile Asp Gly
```

```
                   85                  90                  95                 100
caa aaa aaa aag tgt gga gaa gaa aga cgg aga gta aac caa ttc cta              392
Gln Lys Lys Lys Cys Gly Glu Glu Arg Arg Arg Val Asn Gln Phe Leu
                   105                 110                 115 gac tac ctg caa gag ttt ctt ggt gta atg aac acc gag tgg ata ata              440
Asp Tyr Leu Gln Glu Phe Leu Gly Val Met Asn Thr Glu Trp Ile Ile
            120                 125                 130 gaa agt tga gactaaactg gtttgttgca gccaaagatt ttggaggaga                      489
Glu Ser aggacatttt actgcagtga gaatgagggc aagaaagag tcaggcctta attttcagta             549
taatttaact tcagagggaa agtaaatatt tcaggcatac tgacactttg ccagaaagca            609
taaaattctt aaaatatatt tcagatatca gaatcattga agtattttcc tccaggcaaa            669
attgatatac ttttttctta tttaacttaa cattctgtaa aatgtctgtt aacttaatag            729
tatttatgaa atggttaaga atttggtaaa ttagtattta tttaatgtta tgttgtgttc            789
taataaaaca aaaatagaca actgtt                                                 815

<210> SEQ ID NO 2
<211> LENGTH: 134
<212> TYPE: PRT
<213> ORGANISM: Homo sapiens

<400> SEQUENCE: 2

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 3
<211> LENGTH: 1005
<212> TYPE: DNA
<213> ORGANISM: Homo sapiens
<220> FEATURE:
<221> NAME/KEY: CDS
<222> LOCATION: (68)..(361)

<400> SEQUENCE: 3
agagaggctg agaccaaccc agaaaccacc acctctcacg ccaaagctca caccttcagc             60 ctccaac atg aag gtc tcc gca gca ctt ctg tgg ctg ctg ctc ata gca            109
        Met Lys Val Ser Ala Ala Leu Leu Trp Leu Leu Leu Ile Ala
        1               5                   10 gct gcc ttc agc ccc cag ggg ctc gct ggg cca gct tct gtc cca acc            157
Ala Ala Phe Ser Pro Gln Gly Leu Ala Gly Pro Ala Ser Val Pro Thr
```

```
                  15                  20                  25                  30
acc tgc tgc ttt aac ctg gcc aat agg aag ata ccc ctt cag cga cta        205
Thr Cys Cys Phe Asn Leu Ala Asn Arg Lys Ile Pro Leu Gln Arg Leu
                    35                  40                  45 gag agc tac agg aga atc acc agt ggc aaa tgt ccc cag aaa gct gtg        253
Glu Ser Tyr Arg Arg Ile Thr Ser Gly Lys Cys Pro Gln Lys Ala Val
            50                  55                  60 atc ttc aag acc aaa ctg gcc aag gat atc tgt gcc gac ccc aag aag        301
Ile Phe Lys Thr Lys Leu Ala Lys Asp Ile Cys Ala Asp Pro Lys Lys
                65                  70                  75 aag tgg gtg cag gat tcc atg aag tat ctg gac caa aaa tct cca act        349
Lys Trp Val Gln Asp Ser Met Lys Tyr Leu Asp Gln Lys Ser Pro Thr
        80                  85                  90 cca aag cca taa ataatcacca tttttgaaac caaaccagag cctgagtgtt            401
Pro Lys Pro
95 gcctaatttg ttttcccttc ttacaatgca ttctgaggta acctcattat cagtccaaag      461 ggcatgggtt ttattatata tatatatttt ttttttttaa aaaaaaacgt attgcattta      521 atttattgag gctttaaaac ttatcctcca tgaatatcag ttattttttaa actgtaaagc     581 tttgtgcaga ttctttaccc cctgggagcc ccaattcgat cccctgtcac gtgtgggcaa      641 tgttccccct ctcctctctt cctccctgga atcttgtaaa ggtcctggca aagatgatca     701 gtatgaaaat gtcattgttc ttgtgaaccc aaagtgtgac tcattaaatg gaagtaaatg     761 ttgttttagg aatacataaa gtatgtgcat attttattat agtcactagt tgtaatttt      821 ttgtgggaaa tccacactga gctgagggg acaaagatgg ctgtggccaa gaggggcttg      881 gttaagggg tgggaactat gtccctggga aatgagtttt tggcttagct ggtcttcatt     941 gaaatgcagg gtgaaactga caaacccatt ccagccctct attcccattt tcaacagtat    1001 ttcc                                                                  1005

<210> SEQ ID NO 4
<211> LENGTH: 97
<212> TYPE: PRT
<213> ORGANISM: Homo sapiens

<400> SEQUENCE: 4

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
                    35                  40                  45

Tyr Arg Arg Ile Thr Ser Gly Lys Cys Pro Gln Lys Ala Val Ile Phe
            50                  55                  60

Lys Thr Lys Leu Ala Lys Asp Ile Cys Ala Asp Pro Lys Lys Trp
65                  70                  75                  80

Val Gln Asp Ser Met Lys Tyr Leu Asp Gln Lys Ser Pro Thr Pro Lys
                85                  90                  95

Pro

<210> SEQ ID NO 5
<211> LENGTH: 1422
<212> TYPE: DNA
<213> ORGANISM: Homo sapiens
<220> FEATURE:
<221> NAME/KEY: CDS
```

<222> LOCATION: (92)..(451)

<400> SEQUENCE: 5

```
actctgcaag gacccgagct atttatccct aggtcctttc ctcctgcacg tcagctttga    60
gccccgagct ggtgcttctg ctctctgaga c atg gca ggc ctg atg acc ata      112
                                   Met Ala Gly Leu Met Thr Ile
                                   1               5 gta acc agc ctt ctg ttc ctt ggt gtc tgt gcc cac cac atc atc cct    160
Val Thr Ser Leu Leu Phe Leu Gly Val Cys Ala His His Ile Ile Pro
         10                  15                  20 acg ggc tct gtg gtc atc ccc tct ccc tgc tgc atg ttc ttt gtt tcc    208
Thr Gly Ser Val Val Ile Pro Ser Pro Cys Cys Met Phe Phe Val Ser
 25                  30                  35 aag aga att cct gag aac cga gtc gtc agc tac cag ctg tcc agc agg    256
Lys Arg Ile Pro Glu Asn Arg Val Val Ser Tyr Gln Leu Ser Ser Arg
40                  45                  50                  55 agc aca tgc ctc aag gca gga gtg atc ttc acc acc aag aag ggc cag    304
Ser Thr Cys Leu Lys Ala Gly Val Ile Phe Thr Thr Lys Lys Gly Gln
                 60                  65                  70 cag ttc tgt ggc gac ccc aag cag gag tgg gtc cag agg tac atg aag    352
Gln Phe Cys Gly Asp Pro Lys Gln Glu Trp Val Gln Arg Tyr Met Lys
             75                  80                  85 aac ctg gac gcc aag cag aag aag gct tcc cct agg gcc agg gca gtg    400
Asn Leu Asp Ala Lys Gln Lys Lys Ala Ser Pro Arg Ala Arg Ala Val
         90                  95                 100 gct gtc aag ggc cct gtc cag aga tat cct ggc aac caa acc acc tgc    448
Ala Val Lys Gly Pro Val Gln Arg Tyr Pro Gly Asn Gln Thr Thr Cys
     105                 110                 115 taa tccccgccca gcctccagc cctgagtttg ggcctgagct gcttggcggg           501
ctactcgggg cctggagaag ccacagtgat gggggggaaga gctaattttc ctgtttctta  561
gcaacactct ccagggatgt gtctcttcta tgaaaaaccc gagggagcag gtgatgtggt   621
tcccgggggc tgagcaatgg ctccaagcat ccaaggcccc ttgcctttct ggagctgggt   681
gagaagatcc cagaaggaga gcagtggcaa ctctttgcct tctcctcctg acctggttct   741
gatgcttttt cttttttttt ttttttctgag acggagtctc gctctgtcac ccaggctgga  801
gtgcagtggc acaatctcgg ttcactgcaa cctccgcctc ctgggttcaa gtgattctcg   861
tgcctcagcc tcccgagtac ctgggactac aggtgtgtac caccacaccc aactaacttt   921 tgtatttta gtagagatga ggtttcacca tgttggccag gctggtctca aactcctggc    981
ctcaagtgat ctacctgcct cggcctccca aagtgctggg attacaggca tgagccacca  1041
cacccagcct actcaaactt ttatgttgaa aaaaaaaat cataattttt ttttttttaa   1101
aggaaatgaa cgtggaggac tggggtgaag ggccagcctg ggtagtttaa tcttttttggg 1161 aagacatgac tttaaggaga ttccctgctt tgtgacaggt tgctccatgc tgtcttgggg  1221
acaagggcct gtactgcctt caaatctggg ctcaccccac attttggtga ggggaagata  1281
gggtgggggg attaggggga gaaaagactc tagcttttt tttctatgca tgatatactg   1341
tgtgggttta tcaagagtgt agacacagtt gctgttctca aataataggc caaataaaat  1401
gcgattcttt ttttctttga a                                            1422
```

<210> SEQ ID NO 6
<211> LENGTH: 119
<212> TYPE: PRT
<213> ORGANISM: Homo sapiens

<400> SEQUENCE: 6

```
Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
            20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
            115
```

<210> SEQ ID NO 7
<211> LENGTH: 21
<212> TYPE: DNA
<213> ORGANISM: Mus musculus

<400> SEQUENCE: 7
atgaacgcta cacactgcat c                                           21

<210> SEQ ID NO 8
<211> LENGTH: 21
<212> TYPE: DNA
<213> ORGANISM: Mus musculus

<400> SEQUENCE: 8
ccatcctttt gccagttcct c                                           21

<210> SEQ ID NO 9
<211> LENGTH: 23
<212> TYPE: DNA
<213> ORGANISM: Mus musculus

<400> SEQUENCE: 9
ccctcacact cagatcatct tct                                         23

<210> SEQ ID NO 10
<211> LENGTH: 19
<212> TYPE: DNA
<213> ORGANISM: Mus musculus

<400> SEQUENCE: 10
gctacgacgt gggctacag                                              19

<210> SEQ ID NO 11
<211> LENGTH: 23
<212> TYPE: DNA
<213> ORGANISM: Mus musculus

<400> SEQUENCE: 11
ctctgttgac aagcaatgag acg                                         23

<210> SEQ ID NO 12
<211> LENGTH: 22
<212> TYPE: DNA

```
<213> ORGANISM: Mus musculus

<400> SEQUENCE: 12
tcttcagtat gtctagcccc tg                                               22

<210> SEQ ID NO 13
<211> LENGTH: 21
<212> TYPE: DNA
<213> ORGANISM: Mus musculus

<400> SEQUENCE: 13
tccaactcca agatttcccc g                                                21

<210> SEQ ID NO 14
<211> LENGTH: 21
<212> TYPE: DNA
<213> ORGANISM: Mus musculus

<400> SEQUENCE: 14
catgcagtag acatggcaga a                                                21

<210> SEQ ID NO 15
<211> LENGTH: 20
<212> TYPE: DNA
<213> ORGANISM: Mus musculus

<400> SEQUENCE: 15
ggtctcaacc cccagctagt                                                  20

<210> SEQ ID NO 16
<211> LENGTH: 23
<212> TYPE: DNA
<213> ORGANISM: Mus musculus

<400> SEQUENCE: 16
gccgatgatc tctctcaagt gat                                              23

<210> SEQ ID NO 17
<211> LENGTH: 21
<212> TYPE: DNA
<213> ORGANISM: Mus musculus

<400> SEQUENCE: 17
ggccttggaa gcatgtagag g                                                21

<210> SEQ ID NO 18
<211> LENGTH: 23
<212> TYPE: DNA
<213> ORGANISM: Mus musculus

<400> SEQUENCE: 18
ggagaactcg ttagagacga ctt                                              23

<210> SEQ ID NO 19
<211> LENGTH: 23
<212> TYPE: DNA
<213> ORGANISM: Mus musculus

<400> SEQUENCE: 19
gttctcagcc caacaataca aga                                              23

<210> SEQ ID NO 20
<211> LENGTH: 19
```

```
<212> TYPE: DNA
<213> ORGANISM: Mus musculus

<400> SEQUENCE: 20
gtggacgggt cgatgtcac                                                19

<210> SEQ ID NO 21
<211> LENGTH: 19
<212> TYPE: DNA
<213> ORGANISM: Mus musculus

<400> SEQUENCE: 21
cgtgcgtgac atcaaagag                                                19

<210> SEQ ID NO 22
<211> LENGTH: 18
<212> TYPE: DNA
<213> ORGANISM: Mus musculus

<400> SEQUENCE: 22
tgccacagga ttccatac                                                 18

<210> SEQ ID NO 23
<211> LENGTH: 23
<212> TYPE: DNA
<213> ORGANISM: Mus musculus

<400> SEQUENCE: 23
taccatgagg tcacttcaga tgc                                           23

<210> SEQ ID NO 24
<211> LENGTH: 20
<212> TYPE: DNA
<213> ORGANISM: Mus musculus

<400> SEQUENCE: 24
gcactctcgg cctacattgg                                               20

<210> SEQ ID NO 25
<211> LENGTH: 19
<212> TYPE: DNA
<213> ORGANISM: Mus musculus

<400> SEQUENCE: 25
cctggctctt gcttgcctt                                                19

<210> SEQ ID NO 26
<211> LENGTH: 21
<212> TYPE: DNA
<213> ORGANISM: Mus musculus

<400> SEQUENCE: 26
ggtcttgtgt gatgttgctc a                                             21

<210> SEQ ID NO 27
<211> LENGTH: 21
<212> TYPE: DNA
<213> ORGANISM: Mus musculus

<400> SEQUENCE: 27
ggagttcgag gaaccctagt g                                             21

<210> SEQ ID NO 28
```

```
<211> LENGTH: 21
<212> TYPE: DNA
<213> ORGANISM: Mus musculus

<400> SEQUENCE: 28
gggatttgta gtggatcgtg c                                              21

<210> SEQ ID NO 29
<211> LENGTH: 21
<212> TYPE: DNA
<213> ORGANISM: Mus musculus

<400> SEQUENCE: 29
ccaagtgctg ccgtcatttt c                                              21

<210> SEQ ID NO 30
<211> LENGTH: 21
<212> TYPE: DNA
<213> ORGANISM: Mus musculus

<400> SEQUENCE: 30
ggctcgcagg gatgatttca a                                              21

<210> SEQ ID NO 31
<211> LENGTH: 23
<212> TYPE: DNA
<213> ORGANISM: Mus musculus

<400> SEQUENCE: 31
ggcttcctta tgttcaaaca ggg                                            23

<210> SEQ ID NO 32
<211> LENGTH: 22
<212> TYPE: DNA
<213> ORGANISM: Mus musculus

<400> SEQUENCE: 32
gccgttactc gggtaaatta ca                                             22

<210> SEQ ID NO 33
<211> LENGTH: 21
<212> TYPE: DNA
<213> ORGANISM: Mus musculus

<400> SEQUENCE: 33
aggtccctat ggtgccaatg t                                              21

<210> SEQ ID NO 34
<211> LENGTH: 20
<212> TYPE: DNA
<213> ORGANISM: Mus musculus

<400> SEQUENCE: 34
cggcaggatt ttgaggtcca                                                20

<210> SEQ ID NO 35
<211> LENGTH: 4206
<212> TYPE: DNA
<213> ORGANISM: Homo sapiens
<220> FEATURE:
<221> NAME/KEY: CDS
<222> LOCATION: (265)..(3726)

<400> SEQUENCE: 35
```

-continued

```
ataactttgt agcgagtcga aaactgaggc tccggccgca gagaactcag cctcattcct    60
gctttaaaat ctctcggcca cctttgatga ggggactggg cagttctaga cagtcccgaa   120
gttctcaagg cacaggtctc ttcctggttt gactgtcctt accccgggga ggcagtgcag   180
ccagctgcaa gccccacagt gaagaacatc tgagctcaaa tccagataag tgacataagt   240
gacctgcttt gtaaagccat agag atg gcc tgt cct tgg aaa ttt ctg ttc      291
                             Met Ala Cys Pro Trp Lys Phe Leu Phe
                              1               5 aag acc aaa ttc cac cag tat gca atg aat ggg gaa aaa gac atc aac    339
Lys Thr Lys Phe His Gln Tyr Ala Met Asn Gly Glu Lys Asp Ile Asn
 10              15                  20                  25 aac aat gtg gag aaa gcc ccc tgt gcc acc tcc agt cca gtg aca cag    387
Asn Asn Val Glu Lys Ala Pro Cys Ala Thr Ser Ser Pro Val Thr Gln
                 30                  35                  40 gat gac ctt cag tat cac aac ctc agc aag cag cag aat gag tcc ccg    435
Asp Asp Leu Gln Tyr His Asn Leu Ser Lys Gln Gln Asn Glu Ser Pro
             45                  50                  55 cag ccc ctc gtg gag acg gga aag aag tct cca gaa tct ctg gtc aag    483
Gln Pro Leu Val Glu Thr Gly Lys Lys Ser Pro Glu Ser Leu Val Lys
         60                  65                  70 ctg gat gca acc cca ttg tcc tcc cca cgg cat gtg agg atc aaa aac    531
Leu Asp Ala Thr Pro Leu Ser Ser Pro Arg His Val Arg Ile Lys Asn
 75                  80                  85 tgg ggc agc ggg atg act ttc caa gac aca ctt cac cat aag gcc aaa    579
Trp Gly Ser Gly Met Thr Phe Gln Asp Thr Leu His His Lys Ala Lys
 90                  95                 100                 105 ggg att tta act tgc agg tcc aaa tct tgc ctg ggg tcc att atg act    627
Gly Ile Leu Thr Cys Arg Ser Lys Ser Cys Leu Gly Ser Ile Met Thr
                110                 115                 120 ccc aaa agt ttg acc aga gga ccc agg gac aag cct acc cct cca gat    675
Pro Lys Ser Leu Thr Arg Gly Pro Arg Asp Lys Pro Thr Pro Pro Asp
            125                 130                 135 gag ctt cta cct caa gct atc gaa ttt gtc aac caa tat tac ggc tcc    723
Glu Leu Leu Pro Gln Ala Ile Glu Phe Val Asn Gln Tyr Tyr Gly Ser
        140                 145                 150 ttc aaa gag gca aaa ata gag gaa cat ctg gcc agg gtg gaa gcg gta    771
Phe Lys Glu Ala Lys Ile Glu Glu His Leu Ala Arg Val Glu Ala Val
155                 160                 165 aca aag gag ata gaa aca aca gga acc tac caa ctg acg gga gat gag    819
Thr Lys Glu Ile Glu Thr Thr Gly Thr Tyr Gln Leu Thr Gly Asp Glu
170                 175                 180                 185 ctc atc ttc gcc acc aag cag gcc tgg cgc aat gcc cca cgc tgc att    867
Leu Ile Phe Ala Thr Lys Gln Ala Trp Arg Asn Ala Pro Arg Cys Ile
                190                 195                 200 ggg agg atc cag tgg tcc aac ctg cag gtc ttc gat gcc cgc agc tgt    915
Gly Arg Ile Gln Trp Ser Asn Leu Gln Val Phe Asp Ala Arg Ser Cys
            205                 210                 215 tcc act gcc cgg gaa atg ttt gaa cac atc tgc aga cac gtg cgt tac    963
Ser Thr Ala Arg Glu Met Phe Glu His Ile Cys Arg His Val Arg Tyr
        220                 225                 230 tcc acc aac aat ggc aac atc agg tcg gcc atc acc gtg ttc ccc cag   1011
Ser Thr Asn Asn Gly Asn Ile Arg Ser Ala Ile Thr Val Phe Pro Gln
235                 240                 245 cgg agt gat ggc aag cac gac ttc cgg gtg tgg aat gct cag ctc atc   1059
Arg Ser Asp Gly Lys His Asp Phe Arg Val Trp Asn Ala Gln Leu Ile
250                 255                 260                 265 cgc tat gct ggc tac cag atg cca gat ggc agc atc aga ggg gac cct   1107
Arg Tyr Ala Gly Tyr Gln Met Pro Asp Gly Ser Ile Arg Gly Asp Pro
                270                 275                 280
```

```
gcc aac gtg gaa ttc act cag ctg tgc atc gac ctg ggc tgg aag ccc      1155
Ala Asn Val Glu Phe Thr Gln Leu Cys Ile Asp Leu Gly Trp Lys Pro
            285                 290                 295 aag tac ggc cgc ttc gat gtg gtc ccc ctg gtc ctg cag gcc aat ggc      1203
Lys Tyr Gly Arg Phe Asp Val Val Pro Leu Val Leu Gln Ala Asn Gly
            300                 305                 310 cgt gac cct gag ctc ttc gaa atc cca cct gac ctt gtg ctt gag gtg      1251
Arg Asp Pro Glu Leu Phe Glu Ile Pro Pro Asp Leu Val Leu Glu Val
            315                 320                 325 gcc atg gaa cat ccc aaa tac gag tgg ttt cgg gaa ctg gag cta aag      1299
Ala Met Glu His Pro Lys Tyr Glu Trp Phe Arg Glu Leu Glu Leu Lys
330                 335                 340                 345 tgg tac gcc ctg cct gca gtg gcc aac atg ctg ctt gag gtg ggc ggc      1347
Trp Tyr Ala Leu Pro Ala Val Ala Asn Met Leu Leu Glu Val Gly Gly
                350                 355                 360 ctg gag ttc cca ggg tgc ccc ttc aat ggc tgg tac atg ggc aca gag      1395
Leu Glu Phe Pro Gly Cys Pro Phe Asn Gly Trp Tyr Met Gly Thr Glu
            365                 370                 375 atc gga gtc cgg gac ttc tgt gac gtc cag cgc tac aac atc ctg gag      1443
Ile Gly Val Arg Asp Phe Cys Asp Val Gln Arg Tyr Asn Ile Leu Glu
            380                 385                 390 gaa gtg ggc agg aga atg ggc ctg gaa acg cac aag ctg gcc tcg ctc      1491
Glu Val Gly Arg Arg Met Gly Leu Glu Thr His Lys Leu Ala Ser Leu
            395                 400                 405 tgg aaa gac cag gct gtc gtt gag atc aac att gct gtg ctc cat agt      1539
Trp Lys Asp Gln Ala Val Val Glu Ile Asn Ile Ala Val Leu His Ser
410                 415                 420                 425 ttc cag aag cag aat gtg acc atc atg gac cac cac tcg gct gca gaa      1587
Phe Gln Lys Gln Asn Val Thr Ile Met Asp His His Ser Ala Ala Glu
                430                 435                 440 tcc ttc atg aag tac atg cag aat gaa tac cgg tcc cgt ggg ggc tgc      1635
Ser Phe Met Lys Tyr Met Gln Asn Glu Tyr Arg Ser Arg Gly Gly Cys
            445                 450                 455 ccg gca gac tgg att tgg ctg gtc cct ccc atg tct ggg agc atc acc      1683
Pro Ala Asp Trp Ile Trp Leu Val Pro Pro Met Ser Gly Ser Ile Thr
            460                 465                 470 ccc gtg ttt cac cag gag atg ctg aac tac gtc ctg tcc cct ttc tac      1731
Pro Val Phe His Gln Glu Met Leu Asn Tyr Val Leu Ser Pro Phe Tyr
475                 480                 485 tac tat cag gta gag gcc tgg aaa acc cat gtc tgg cag gac gag aag      1779
Tyr Tyr Gln Val Glu Ala Trp Lys Thr His Val Trp Gln Asp Glu Lys
490                 495                 500                 505 cgg aga ccc aag aga aga gag att cca ttg aaa gtc ttg gtc aaa gct      1827
Arg Arg Pro Lys Arg Arg Glu Ile Pro Leu Lys Val Leu Val Lys Ala
            510                 515                 520 gtg ctc ttt gcc tgt atg ctg atg cgc aag aca atg gcg tcc cga gtc      1875
Val Leu Phe Ala Cys Met Leu Met Arg Lys Thr Met Ala Ser Arg Val
            525                 530                 535 aga gtc acc atc ctc ttt gcg aca gag aca gga aaa tca gag gcg ctg      1923
Arg Val Thr Ile Leu Phe Ala Thr Glu Thr Gly Lys Ser Glu Ala Leu
            540                 545                 550 gcc tgg gac ctg ggg gcc tta ttc agc tgt gcc ttc aac ccc aag gtt      1971
Ala Trp Asp Leu Gly Ala Leu Phe Ser Cys Ala Phe Asn Pro Lys Val
555                 560                 565 gtc tgc atg gat aag tac agg ctg agc tgc ctg gag gag gaa cgg ctg      2019
Val Cys Met Asp Lys Tyr Arg Leu Ser Cys Leu Glu Glu Glu Arg Leu
570                 575                 580                 585 ctg ttg gtg gtg acc agt acg ttt ggc aat gga gac tgc cct ggc aat      2067
Leu Leu Val Val Thr Ser Thr Phe Gly Asn Gly Asp Cys Pro Gly Asn
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 590 |     |     |     |     | 595 |     |     |     |     | 600 |     |     |      |
| gga | gag | aaa | ctg | aag | aaa | tcg | ctc | ttc | atg | ctg | aaa | gag | ctc | aac | aac | 2115 |
| Gly | Glu | Lys | Leu | Lys | Lys | Ser | Leu | Phe | Met | Leu | Lys | Glu | Leu | Asn | Asn |      |
|     |     |     | 605 |     |     |     |     | 610 |     |     |     |     | 615 |     |     |      |
| aaa | ttc | agg | tac | gct | gtg | ttt | ggc | ctc | ggc | tcc | agc | atg | tac | cct | cgg | 2163 |
| Lys | Phe | Arg | Tyr | Ala | Val | Phe | Gly | Leu | Gly | Ser | Ser | Met | Tyr | Pro | Arg |      |
|     |     | 620 |     |     |     |     | 625 |     |     |     |     | 630 |     |     |     |      |
| ttc | tgc | gcc | ttt | gct | cat | gac | att | gat | cag | aag | ctg | tcc | cac | ctg | ggg | 2211 |
| Phe | Cys | Ala | Phe | Ala | His | Asp | Ile | Asp | Gln | Lys | Leu | Ser | His | Leu | Gly |      |
|     | 635 |     |     |     |     | 640 |     |     |     |     | 645 |     |     |     |     |      |
| gcc | tct | cag | ctc | acc | ccg | atg | gga | gaa | ggg | gat | gag | ctc | agt | ggg | cag | 2259 |
| Ala | Ser | Gln | Leu | Thr | Pro | Met | Gly | Glu | Gly | Asp | Glu | Leu | Ser | Gly | Gln |      |
| 650 |     |     |     |     | 655 |     |     |     |     | 660 |     |     |     |     | 665 |      |
| gag | gac | gcc | ttc | cgc | agc | tgg | gcc | gtg | caa | acc | ttc | aag | gca | gcc | tgt | 2307 |
| Glu | Asp | Ala | Phe | Arg | Ser | Trp | Ala | Val | Gln | Thr | Phe | Lys | Ala | Ala | Cys |      |
|     |     |     |     | 670 |     |     |     |     | 675 |     |     |     |     | 680 |     |      |
| gag | acg | ttt | gat | gtc | cga | ggc | aaa | cag | cac | att | cag | atc | ccc | aag | ctc | 2355 |
| Glu | Thr | Phe | Asp | Val | Arg | Gly | Lys | Gln | His | Ile | Gln | Ile | Pro | Lys | Leu |      |
|     |     |     | 685 |     |     |     |     | 690 |     |     |     |     | 695 |     |     |      |
| tac | acc | tcc | aat | gtg | acc | tgg | gac | ccg | cac | cac | tac | agg | ctc | gtg | cag | 2403 |
| Tyr | Thr | Ser | Asn | Val | Thr | Trp | Asp | Pro | His | His | Tyr | Arg | Leu | Val | Gln |      |
|     |     | 700 |     |     |     |     | 705 |     |     |     |     | 710 |     |     |     |      |
| gac | tca | cag | cct | ttg | gac | ctc | agc | aaa | gcc | ctc | agc | agc | atg | cat | gcc | 2451 |
| Asp | Ser | Gln | Pro | Leu | Asp | Leu | Ser | Lys | Ala | Leu | Ser | Ser | Met | His | Ala |      |
|     | 715 |     |     |     |     | 720 |     |     |     |     | 725 |     |     |     |     |      |
| aag | aac | gtg | ttc | acc | atg | agg | ctc | aaa | tct | cgg | cag | aat | cta | caa | agt | 2499 |
| Lys | Asn | Val | Phe | Thr | Met | Arg | Leu | Lys | Ser | Arg | Gln | Asn | Leu | Gln | Ser |      |
| 730 |     |     |     |     | 735 |     |     |     |     | 740 |     |     |     |     | 745 |      |
| ccg | aca | tcc | agc | cgt | gcc | acc | atc | ctg | gtg | gaa | ctc | tcc | tgt | gag | gat | 2547 |
| Pro | Thr | Ser | Ser | Arg | Ala | Thr | Ile | Leu | Val | Glu | Leu | Ser | Cys | Glu | Asp |      |
|     |     |     |     | 750 |     |     |     |     | 755 |     |     |     |     | 760 |     |      |
| ggc | caa | ggc | ctg | aac | tac | ctg | ccg | ggg | gag | cac | ctt | ggg | gtt | tgc | cca | 2595 |
| Gly | Gln | Gly | Leu | Asn | Tyr | Leu | Pro | Gly | Glu | His | Leu | Gly | Val | Cys | Pro |      |
|     |     |     | 765 |     |     |     |     | 770 |     |     |     |     | 775 |     |     |      |
| ggc | aac | cag | ccg | gcc | ctg | gtc | caa | ggt | atc | ctg | gag | cga | gtg | gtg | gat | 2643 |
| Gly | Asn | Gln | Pro | Ala | Leu | Val | Gln | Gly | Ile | Leu | Glu | Arg | Val | Val | Asp |      |
|     |     | 780 |     |     |     |     | 785 |     |     |     |     | 790 |     |     |     |      |
| ggc | ccc | aca | ccc | cac | cag | aca | gtg | cgc | ctg | gag | gcc | ctg | gat | gag | agt | 2691 |
| Gly | Pro | Thr | Pro | His | Gln | Thr | Val | Arg | Leu | Glu | Ala | Leu | Asp | Glu | Ser |      |
|     | 795 |     |     |     |     | 800 |     |     |     |     | 805 |     |     |     |     |      |
| ggc | agc | tac | tgg | gtc | agt | gac | aag | agg | ctg | ccc | ccc | tgc | tca | ctc | agc | 2739 |
| Gly | Ser | Tyr | Trp | Val | Ser | Asp | Lys | Arg | Leu | Pro | Pro | Cys | Ser | Leu | Ser |      |
| 810 |     |     |     |     | 815 |     |     |     |     | 820 |     |     |     |     | 825 |      |
| cag | gcc | ctc | acc | tac | ttc | ctg | gac | atc | acc | aca | ccc | cca | acc | cag | ctg | 2787 |
| Gln | Ala | Leu | Thr | Tyr | Phe | Leu | Asp | Ile | Thr | Thr | Pro | Pro | Thr | Gln | Leu |      |
|     |     |     |     | 830 |     |     |     |     | 835 |     |     |     |     | 840 |     |      |
| ctc | ctc | caa | aag | ctg | gcc | cag | gtg | gcc | aca | gaa | gag | cct | gag | aga | cag | 2835 |
| Leu | Leu | Gln | Lys | Leu | Ala | Gln | Val | Ala | Thr | Glu | Glu | Pro | Glu | Arg | Gln |      |
|     |     |     | 845 |     |     |     |     | 850 |     |     |     |     | 855 |     |     |      |
| agg | ctg | gag | gcc | ctg | tgc | cag | ccc | tca | gag | tac | agc | aag | tgg | aag | ttc | 2883 |
| Arg | Leu | Glu | Ala | Leu | Cys | Gln | Pro | Ser | Glu | Tyr | Ser | Lys | Trp | Lys | Phe |      |
|     |     | 860 |     |     |     |     | 865 |     |     |     |     | 870 |     |     |     |      |
| acc | aac | agc | ccc | aca | ttc | ctg | gag | gtg | cta | gag | gag | ttc | cgg | tcc | ctg | 2931 |
| Thr | Asn | Ser | Pro | Thr | Phe | Leu | Glu | Val | Leu | Glu | Glu | Phe | Pro | Ser | Leu |      |
|     | 875 |     |     |     |     | 880 |     |     |     |     | 885 |     |     |     |     |      |
| cgg | gtg | tct | gct | ggc | ttc | ctg | ctt | tcc | cag | ctc | ccc | att | ctg | aag | ccc | 2979 |
| Arg | Val | Ser | Ala | Gly | Phe | Leu | Leu | Ser | Gln | Leu | Pro | Ile | Leu | Lys | Pro |      |
| 890 |     |     |     |     | 895 |     |     |     |     | 900 |     |     |     |     | 905 |      |
| agg | ttc | tac | tcc | atc | agc | tcc | tcc | cgg | gat | cac | acg | ccc | aca | gag | atc | 3027 |

```
                    Arg Phe Tyr Ser Ile Ser Ser Ser Arg Asp His Thr Pro Thr Glu Ile
                                        910                 915                 920 cac ctg act gtg gcc gtg gtc acc tac cac acc cga gat ggc cag ggt                      3075
His Leu Thr Val Ala Val Val Thr Tyr His Thr Arg Asp Gly Gln Gly
                925                 930                 935 ccc ctg cac cac ggc gtc tgc agc aca tgg ctc aac agc ctg aag ccc                      3123
Pro Leu His His Gly Val Cys Ser Thr Trp Leu Asn Ser Leu Lys Pro
                940                 945                 950 caa gac cca gtg ccc tgc ttt gtg cgg aat gcc agc ggc ttc cac ctc                      3171
Gln Asp Pro Val Pro Cys Phe Val Arg Asn Ala Ser Gly Phe His Leu
                955                 960                 965 ccc gag gat ccc tcc cat cct tgc atc ctc atc ggg cct ggc aca ggc                      3219
Pro Glu Asp Pro Ser His Pro Cys Ile Leu Ile Gly Pro Gly Thr Gly
970                 975                 980                 985 atc gcg ccc ttc cgc agt ttc tgg cag caa cgg ctc cat gac tcc cag                      3267
Ile Ala Pro Phe Arg Ser Phe Trp Gln Gln Arg Leu His Asp Ser Gln
                990                 995                 1000 cac aag gga gtg cgg gga ggc cgc atg  acc ttg gtg ttt ggg  tgc                        3312
His Lys Gly Val Arg Gly Gly Arg Met  Thr Leu Val Phe Gly  Cys
                1005                 1010                 1015 cgc cgc cca gat gag gac cac atc tac cag gag gag atg ctg gag                          3357
Arg Arg Pro Asp Glu Asp His Ile Tyr Gln Glu Glu Met Leu Glu
                1020                 1025                 1030 atg gcc cag aag ggg gtg ctg cat gcg gtg cac aca gcc tat tcc                          3402
Met Ala Gln Lys Gly Val Leu His Ala Val His Thr Ala Tyr Ser
                1035                 1040                 1045 cgc ctg cct ggc  aag ccc aag gtc tat gtt cag gac atc ctg cgg                         3447
Arg Leu Pro Gly Lys Pro Lys Val Tyr Val Gln Asp Ile Leu Arg
                1050                 1055                 1060 cag cag ctg gcc agc gag gtg ctc cgt gtg ctc cac aag gag cca                          3492
Gln Gln Leu Ala Ser Glu Val Leu Arg Val Leu His Lys Glu Pro
                1065                 1070                 1075 ggc cac ctc tat gtt tgc ggg gat gtg cgc atg gcc cgg gac gtg                          3537
Gly His Leu Tyr Val Cys Gly Asp Val Arg Met Ala Arg Asp Val
                1080                 1085                 1090 gcc cac acc ctg aag cag ctg gtg gct gcc aag ctg aaa ttg aat                          3582
Ala His Thr Leu Lys Gln Leu Val Ala Ala Lys Leu Lys Leu Asn
                1095                 1100                 1105 gag gag cag gtc gag gac tat ttc ttt cag ctc aag agc cag aag                          3627
Glu Glu Gln Val Glu Asp Tyr Phe Phe Gln Leu Lys Ser Gln Lys
                1110                 1115                 1120 cgc tat cac gaa gat atc ttt ggt gct gta ttt cct tac gag gcg                          3672
Arg Tyr His Glu Asp Ile Phe Gly Ala Val Phe Pro Tyr Glu Ala
                1125                 1130                 1135 aag aag gac agg gtg gcg gtg cag ccc agc agc ctg gag atg tca                          3717
Lys Lys Asp Arg Val Ala Val Gln Pro Ser Ser Leu Glu Met Ser
                1140                 1145                 1150 gcg ctc tga gggcctacag gaggggttaa agctgccggc acagaactta                              3766
Ala Leu aggatggagc cagctctgca ttatctgagg tcacagggcc tggggagatg gaggaaagtg                    3826
atatccccca gcctcaagtc ttatttcctc aacgttgctc cccatcaagc cctttacttg                    3886
acctcctaac aagtagcacc ctggattgat cggagcctcc tctctcaaac tggggcctcc                    3946
ctggtcccTT ggagacaaaa tcttaaatgc caggcctggc aagtgggtga agatggaac                     4006 ttgctgctga gtgcaccact tcaagtgacc accaggaggt gctatcgcac cactgtgtat                    4066
ttaactgcct tgtgtacagt tatttatgcc tctgtattta aaaaactaac acccagtctg                    4126
ttccccatgg ccacttgggt cttccctgta tgattccttg atggagatat ttacatgaat                    4186
```
tgcattttac tttaatcaca                                                    4206

<210> SEQ ID NO 36
<211> LENGTH: 1153
<212> TYPE: PRT
<213> ORGANISM: Homo sapiens

<400> SEQUENCE: 36

Met Ala Cys Pro Trp Lys Phe Leu Phe Lys Thr Lys Phe His Gln Tyr
1               5                   10                  15

Ala Met Asn Gly Glu Lys Asp Ile Asn Asn Val Glu Lys Ala Pro
            20                  25                  30

Cys Ala Thr Ser Ser Pro Val Thr Gln Asp Asp Leu Gln Tyr His Asn
                35                  40                  45

Leu Ser Lys Gln Gln Asn Glu Ser Pro Gln Pro Leu Val Glu Thr Gly
    50                  55                  60

Lys Lys Ser Pro Glu Ser Leu Val Lys Leu Asp Ala Thr Pro Leu Ser
65                  70                  75                  80

Ser Pro Arg His Val Arg Ile Lys Asn Trp Gly Ser Gly Met Thr Phe
                85                  90                  95

Gln Asp Thr Leu His His Lys Ala Lys Gly Ile Leu Thr Cys Arg Ser
            100                 105                 110

Lys Ser Cys Leu Gly Ser Ile Met Thr Pro Lys Ser Leu Thr Arg Gly
        115                 120                 125

Pro Arg Asp Lys Pro Thr Pro Pro Asp Glu Leu Leu Pro Gln Ala Ile
    130                 135                 140

Glu Phe Val Asn Gln Tyr Tyr Gly Ser Phe Lys Glu Ala Lys Ile Glu
145                 150                 155                 160

Glu His Leu Ala Arg Val Glu Ala Val Thr Lys Glu Ile Glu Thr Thr
                165                 170                 175

Gly Thr Tyr Gln Leu Thr Gly Asp Glu Leu Ile Phe Ala Thr Lys Gln
            180                 185                 190

Ala Trp Arg Asn Ala Pro Arg Cys Ile Gly Arg Ile Gln Trp Ser Asn
        195                 200                 205

Leu Gln Val Phe Asp Ala Arg Ser Cys Ser Thr Ala Arg Glu Met Phe
    210                 215                 220

Glu His Ile Cys Arg His Val Arg Tyr Ser Thr Asn Asn Gly Asn Ile
225                 230                 235                 240

Arg Ser Ala Ile Thr Val Phe Pro Gln Arg Ser Asp Gly Lys His Asp
                245                 250                 255

Phe Arg Val Trp Asn Ala Gln Leu Ile Arg Tyr Ala Gly Tyr Gln Met
            260                 265                 270

Pro Asp Gly Ser Ile Arg Gly Asp Pro Ala Asn Val Glu Phe Thr Gln
        275                 280                 285

Leu Cys Ile Asp Leu Gly Trp Lys Pro Lys Tyr Gly Arg Phe Asp Val
    290                 295                 300

Val Pro Leu Val Leu Gln Ala Asn Gly Arg Asp Pro Glu Leu Phe Glu
305                 310                 315                 320

Ile Pro Pro Asp Leu Val Leu Glu Val Ala Met Glu His Pro Lys Tyr
                325                 330                 335

Glu Trp Phe Arg Glu Leu Glu Leu Lys Trp Tyr Ala Leu Pro Ala Val
            340                 345                 350

Ala Asn Met Leu Leu Glu Val Gly Gly Leu Glu Phe Pro Gly Cys Pro
        355                 360                 365

-continued

Phe Asn Gly Trp Tyr Met Gly Thr Glu Ile Gly Val Arg Asp Phe Cys
    370                 375                 380

Asp Val Gln Arg Tyr Asn Ile Leu Glu Glu Val Gly Arg Arg Met Gly
385                 390                 395                 400

Leu Glu Thr His Lys Leu Ala Ser Leu Trp Lys Asp Gln Ala Val Val
                405                 410                 415

Glu Ile Asn Ile Ala Val Leu His Ser Phe Gln Lys Gln Asn Val Thr
            420                 425                 430

Ile Met Asp His His Ser Ala Ala Glu Ser Phe Met Lys Tyr Met Gln
        435                 440                 445

Asn Glu Tyr Arg Ser Arg Gly Gly Cys Pro Ala Asp Trp Ile Trp Leu
    450                 455                 460

Val Pro Pro Met Ser Gly Ser Ile Thr Pro Val Phe His Gln Glu Met
465                 470                 475                 480

Leu Asn Tyr Val Leu Ser Pro Phe Tyr Tyr Gln Val Glu Ala Trp
                485                 490                 495

Lys Thr His Val Trp Gln Asp Glu Lys Arg Arg Pro Lys Arg Arg Glu
                500                 505                 510

Ile Pro Leu Lys Val Leu Val Lys Ala Val Leu Phe Ala Cys Met Leu
            515                 520                 525

Met Arg Lys Thr Met Ala Ser Arg Val Arg Val Thr Ile Leu Phe Ala
        530                 535                 540

Thr Glu Thr Gly Lys Ser Glu Ala Leu Ala Trp Asp Leu Gly Ala Leu
545                 550                 555                 560

Phe Ser Cys Ala Phe Asn Pro Lys Val Val Cys Met Asp Lys Tyr Arg
                565                 570                 575

Leu Ser Cys Leu Glu Glu Glu Arg Leu Leu Leu Val Val Thr Ser Thr
            580                 585                 590

Phe Gly Asn Gly Asp Cys Pro Gly Asn Gly Glu Lys Leu Lys Lys Ser
        595                 600                 605

Leu Phe Met Leu Lys Glu Leu Asn Asn Lys Phe Arg Tyr Ala Val Phe
    610                 615                 620

Gly Leu Gly Ser Ser Met Tyr Pro Arg Phe Cys Ala Phe Ala His Asp
625                 630                 635                 640

Ile Asp Gln Lys Leu Ser His Leu Gly Ala Ser Gln Leu Thr Pro Met
                645                 650                 655

Gly Glu Gly Asp Glu Leu Ser Gly Gln Glu Asp Ala Phe Arg Ser Trp
            660                 665                 670

Ala Val Gln Thr Phe Lys Ala Ala Cys Glu Thr Phe Asp Val Arg Gly
        675                 680                 685

Lys Gln His Ile Gln Ile Pro Lys Leu Tyr Thr Ser Asn Val Thr Trp
    690                 695                 700

Asp Pro His His Tyr Arg Leu Val Gln Asp Ser Gln Pro Leu Asp Leu
705                 710                 715                 720

Ser Lys Ala Leu Ser Ser Met His Ala Lys Asn Val Phe Thr Met Arg
                725                 730                 735

Leu Lys Ser Arg Gln Asn Leu Gln Ser Pro Thr Ser Ser Arg Ala Thr
            740                 745                 750

Ile Leu Val Glu Leu Ser Cys Glu Asp Gly Gln Gly Leu Asn Tyr Leu
        755                 760                 765

Pro Gly Glu His Leu Gly Val Cys Pro Gly Asn Gln Pro Ala Leu Val
    770                 775                 780

-continued

```
Gln Gly Ile Leu Glu Arg Val Val Asp Gly Pro Thr Pro His Gln Thr
785                 790                 795                 800

Val Arg Leu Glu Ala Leu Asp Glu Ser Gly Ser Tyr Trp Val Ser Asp
            805                 810                 815

Lys Arg Leu Pro Pro Cys Ser Leu Ser Gln Ala Leu Thr Tyr Phe Leu
            820                 825                 830

Asp Ile Thr Thr Pro Pro Thr Gln Leu Leu Leu Gln Lys Leu Ala Gln
            835                 840                 845

Val Ala Thr Glu Glu Pro Glu Arg Gln Arg Leu Glu Ala Leu Cys Gln
850                 855                 860

Pro Ser Glu Tyr Ser Lys Trp Lys Phe Thr Asn Ser Pro Thr Phe Leu
865                 870                 875                 880

Glu Val Leu Glu Glu Phe Pro Ser Leu Arg Val Ser Ala Gly Phe Leu
                885                 890                 895

Leu Ser Gln Leu Pro Ile Leu Lys Pro Arg Phe Tyr Ser Ile Ser Ser
            900                 905                 910

Ser Arg Asp His Thr Pro Thr Glu Ile His Leu Thr Val Ala Val Val
            915                 920                 925

Thr Tyr His Thr Arg Asp Gly Gln Gly Pro Leu His His Gly Val Cys
930                 935                 940

Ser Thr Trp Leu Asn Ser Leu Lys Pro Gln Asp Pro Val Pro Cys Phe
945                 950                 955                 960

Val Arg Asn Ala Ser Gly Phe His Leu Pro Glu Asp Pro Ser His Pro
                965                 970                 975

Cys Ile Leu Ile Gly Pro Gly Thr Gly Ile Ala Pro Phe Arg Ser Phe
            980                 985                 990

Trp Gln Gln Arg Leu His Asp Ser  Gln His Lys Gly Val  Arg Gly Gly
            995                 1000                1005

Arg Met  Thr Leu Val Phe Gly  Cys Arg Arg Pro Asp  Glu Asp His
    1010                1015                1020

Ile Tyr  Gln Glu Glu Met Leu  Glu Met Ala Gln Lys  Gly Val Leu
    1025                1030                1035

His Ala  Val His Thr Ala Tyr  Ser Arg Leu Pro Gly  Lys Pro Lys
    1040                1045                1050

Val Tyr  Val Gln Asp Ile Leu  Arg Gln Gln Leu Ala  Ser Glu Val
    1055                1060                1065

Leu Arg  Val Leu His Lys Glu  Pro Gly His Leu Tyr  Val Cys Gly
    1070                1075                1080

Asp Val  Arg Met Ala Arg Asp  Val Ala His Thr Leu  Lys Gln Leu
    1085                1090                1095

Val Ala  Ala Lys Leu Lys Leu  Asn Glu Glu Gln Val  Glu Asp Tyr
    1100                1105                1110

Phe Phe  Gln Leu Lys Ser Gln  Lys Arg Tyr His Glu  Asp Ile Phe
    1115                1120                1125

Gly Ala  Val Phe Pro Tyr Glu  Ala Lys Lys Asp Arg  Val Ala Val
    1130                1135                1140

Gln Pro  Ser Ser Leu Glu Met  Ser Ala Leu
    1145                1150
```